(12) United States Patent
Ori

(10) Patent No.: US 10,987,019 B2
(45) Date of Patent: Apr. 27, 2021

(54) SYSTEMS AND METHODS FOR HIGH FREQUENCY IMPEDANCE SPECTROSCOPY DETECTION OF DAILY CHANGES OF DIELECTRIC PROPERTIES OF THE HUMAN BODY TO MEASURE BODY COMPOSITION AND HYDRATION STATUS

(71) Applicant: Ori Diagnostic Instruments, LLC, Durham, NC (US)

(72) Inventor: Zsolt Peter Ori, Durham, NC (US)

( * ) Notice: Subject to any disclaimer, the term of this patent is extended or adjusted under 35 U.S.C. 154(b) by 0 days.

(21) Appl. No.: 16/784,341

(22) Filed: Feb. 7, 2020

(65) Prior Publication Data

US 2020/0253505 A1    Aug. 13, 2020

Related U.S. Application Data

(60) Division of application No. 15/673,092, filed on Aug. 9, 2017, now Pat. No. 10,653,333, and a
(Continued)

(51) Int. Cl.
*A61B 5/053*    (2021.01)
*A61B 5/00*    (2006.01)
(Continued)

(52) U.S. Cl.
CPC .......... *A61B 5/0537* (2013.01); *A61B 5/4866* (2013.01); *A61B 5/6829* (2013.01);
(Continued)

(58) Field of Classification Search
CPC ... A61B 5/0537; A61B 5/4866; A61B 5/4872; A61B 5/7225; A61B 5/7278;
(Continued)

(56) References Cited

U.S. PATENT DOCUMENTS 5,280,429 A    1/1994 Withers
6,506,152 B1    1/2003 Lackey et al.
(Continued)

OTHER PUBLICATIONS

Analiza M Silva et al. Extracellular water across the adult lifespan: reference values for adults. 2007 Physiol. Meas. 28 489. https://doi.org/10.1088/0967-3334/28/5/004.
(Continued)

*Primary Examiner* — Patrick Fernandes
*Assistant Examiner* — Benjamin S Melhus
(74) *Attorney, Agent, or Firm* — Olive Law Group, PLLC

(57) ABSTRACT

Systems and methods for high frequency impedance spectroscopy detection of daily changes of dielectric properties of the human body to measure body composition and hydration status. According to an aspect, a method at a computing device to determine a set of indirect dynamic human metabolism parameters includes using a sensor on an individual to acquire a set of electrical measurements. The method also includes combining a ratio technique with a canonical model form technique. The also includes performing a series of mathematical calculations on the acquired set of electrical measurements to determine the set of indirect dynamic human metabolism parameters for the individual based on the combined ratio technique and the canonical model form technique. The method further includes generating a trend regarding the set of indirect dynamic human metabolism parameters in response to performing the series of mathematical calculations on the acquired set of electrical measurements to determine the set of indirect dynamic human metabolism parameters for the individual.

5 Claims, 37 Drawing Sheets

Related U.S. Application Data continuation-in-part of application No. 14/541,033, filed on Nov. 13, 2014, now Pat. No. 9,949,663.

(60) Provisional application No. 62/372,363, filed on Aug. 9, 2016.

(51) Int. Cl.
  *A61B 5/0537* (2021.01)
  *G16H 50/30* (2018.01)
  *G16H 50/50* (2018.01)

(52) U.S. Cl.
  CPC .......... *A61B 5/7278* (2013.01); *A61B 5/4869* (2013.01); *A61B 5/4872* (2013.01); *A61B 5/7225* (2013.01); *A61B 5/7275* (2013.01); *G16H 50/30* (2018.01); *G16H 50/50* (2018.01)

(58) Field of Classification Search
  CPC ... A61B 5/4869; A61B 5/6829; A61B 5/7275; A61B 5/4875; A61B 5/7203; A61B 5/7221; G16H 50/30; G16H 50/50; G16B 40/00
  See application file for complete search history.

(56) References Cited

U.S. PATENT DOCUMENTS

| | | | |
|---|---|---|---|
| 6,620,106 | B2 | 9/2003 | Mault |
| 6,631,292 | B1 | 10/2003 | Liedtke |
| 8,280,484 | B2* | 10/2012 | Boyden .............. A61M 5/14276 600/407 |
| 9,591,987 | B1 | 3/2017 | Liedtke |
| 9,672,471 | B2* | 6/2017 | Boyden .................. A61B 5/021 |
| 2005/0107719 | A1* | 5/2005 | Arad (Abbound) .......................... A61B 5/7289 600/547 |
| 2012/0165622 | A1 | 6/2012 | Rodriguez et al. |
| 2014/0031713 | A1 | 1/2014 | Gaw et al. |
| 2015/0201861 | A1 | 7/2015 | Ko et al. |
| 2017/0007151 | A1 | 1/2017 | Rutkove et al. |
| 2017/0340239 | A1 | 11/2017 | Ori |

OTHER PUBLICATIONS

Andrea C. Buchholz, PhD, RD, et al. The Validity of Bioelectrical Impedance Models in Clinical Populations. Nutrition in Clinical Practice. Jan. 6, 2017. vol. 19, Issue 5, pp. 433-446.

Asselin MC, Kriemler S, Chettle DR, Webber CE, Bar-Or O, et al. (1998) Hydration status assessed by multi-frequency bioimpedance analysis. Appl Radiat Isot 49: 495-497.

B H Cornish et al. Improved prediction of extracellular and total body water using impedance loci generated by multiple frequency bioelectrical impedance analysis. Center for Med. & Health Phys., Queensland Univ. of Technol., Brisbane, Qld., Australia. 1993 Phys. Med. Biol. 38 337. DOI: 10.1088/0031-9155/38/3/001.

Bertemes-Filho, Pedro, et al. High Accurate Howland Current Source: Output Constraints Analysis. Circuits and Systems, 2013, 4, 451-458 Published Online Nov. 2013 (http://www.scirp.org/journal/cs) http://dx.doi.org/10.4236/cs.2013.47059.

C Lelliott and A J Vidal-Puig. Lipotoxicity, an imbalance between lipogenesis de novo and fatty acid oxidation. International Journal of Obesity (2004) 28, S22-S28. doi:10.1038/sj.ijo.0802854.

Ellis KJ, Wong WW (1998) Human hydrometry: comparison of multifrequency bioelectrical impedance with 2H2O and bromine dilution. J Appl Physiol 85(3): 1056-1062.

Food and Nutrition Board, Institute of Medicine. Dietary Reference Intakes for Energy, Carbohydrate, Fiber, Fat, Fatty Acids, Cholesterol, Protein, and Amino Acids (Macronutrients): A Report of the Panel on Macronutrients, Subcommittees on Upper Reference Levels of Nutrients and Interpretation and Uses of Dietary Reference Intakes, and the Standing Committee on the Scientific Evaluation of Dietary Reference Intakes. http://www.nap.edu/books/0309085373/html/.

Gerritsen, Willard et al. Simulation studies of statistical distributions of cell membrane capacities and an ellipse model to assess the frequency behaviour of biological tissues.DOI:10.1088/1742-6596/434/1/012005.

Grewal M.S. and A.P. Andrews. Kalman Filtering: Theory and Practice Using Matlab. John Wiley & Sons, New Jersey. Third Ed.; Sep. 2011, 136 pp.

Grewal M.S. and A.P. Andrews. Kalman Filtering: Theory and Practice Using MATLAB. John Wiley & Sons, New Jersey. Third Ed.; Sep. 2011, pp. 140.

Grewal M.S. and A.P. Andrews. Kalman Filtering: Theory and Practice Using Matlab. John Wiley & Sons, New Jersey. Third Ed.; Sep. 2011, pp. 183.

H Scharfetter et al. Hardware for quasi-single-shot multifrequency magnetic induction tomography (MIT): the Graz Mk2 system. 2008 Physiol. Meas. 29 S431. https://doi.org/10.1088/0967-3334/29/6/S36.

Hebert, James & B Ebbeling, Cara & E Matthews, Charles & Hurley, Thomas & MA, Yunsheng & Druker, Susan & Clemow, Lynn. (2002). Systematic errors in middle-aged women's estimates of energy intake: Comparing three self-report measures to total energy expenditure from doubly labeled water. Annals of epidemiology. 12. 577-86. 10.1016/S1047-2797(01)00297-6.

IEEE Trial-Use Standard for Digitizing Waveform Records, p. 13-14.

Indirect calorimetry: methodological and interpretative problems, American Journal of Physiology—Endocrinology and Metabolism. Mar. 1990; 258(3):E399-E412.

Jaffrin MY, Morel H. Body fluid volumes measurements by impedance: A review of bioimpedance spectroscopy (BIS) and bioimpedance analysis (BIA) methods. Med Eng Phys. Dec. 2008;30(10):1257-69. doi: 10.1016/j.medengphy.2008.06.009. Epub Aug. 3, 2008.

Jazwinski, A.W. Stochastic Processes and Filtering Theory. 1970; Academic Press, Inc. New York, pp. 376.

Kevin D. Hall, Computational model of in vivo human energy metabolism during semistarvation and refeeding. American Journal of Physiology—Endocrinology and Metabolism. Jul. 2006; 291(1):E23-E37. DOI: 10.1152/ajpendo.00523.

Kevin D. Hall, Predicting metabolic adaptation, body weight change, and energy intake in humans. American Journal of Physiology—Endocrinology and Metabolism. Mar. 2010; 298(3):E449-E466. DOI: 10.1152/ajpendo.00559.2009.

Lean, et al. Predicting body composition vector by densitometry from simple anthropometric measurements. American Journal of Clinical Nutrition, Jan. 1996; 63(1) : 4-14.

Livesey, G. and M. Elia. Estimation of energy expenditure, net carbohydrate utilization, and net fat oxidation and synthesis by indirect calorimetry: evaluation of errors with special reference to the detailed composition of fuels. American Journal of Clinical Nutrition. Apr. 1988; 47(4):608-628.

Ljung, L. and T. Söderström. Theory and Practice of Recursive Identification. 1983; MIT Press, Cambridge, Massachusetts, pp. 125.

M. Bertocco and C. Narduzzi, "Sine-fit versus discrete Fourier transform-based algorithms in SNR testing of waveform digitizers," in IEEE Transactions on Instrumentation and Measurement, vol. 46, No. 2, pp. 445-448, Apr. 1997. doi: 10.1109/19.571881.

Mason, C., Foster-Schubert, K. E., Imayama, I., Kong, A., Xiao, L., Bain, C., . . . McTieman, A. (2011). Dietary weight loss and exercise effects on insulin resistance in postmenopausal women. American Journal of Preventive Medicine, 41(4), 366-375. DOI: 10.1016/j.amepre.2011.06.042.

Restriction Requirement (dated Dec. 9, 2016) received in parent application (U.S. Appl. No. 14/541,033).

Ulrich M. Moissl, Body fluid volume determination via body composition spectroscopy in health and disease. Physiological Measurement. Sep. 2006; 27(9):921-933. DOI: 10.1088/0967-3334/27/9/012.

Venkataraman, P. Applied Optimization with MATLAB Programming. Mar. 2009; John Wiley & Sons, pp. 490.

(56) References Cited

OTHER PUBLICATIONS

Walter, E. and L. Pronzato. Identification of Parametric Models from Experimental Data. 1997; Springer Verlag Berlin, Paris, New York. pp. 114.

Wang Z, Shen W, Kotler DP, Heshka S, Wielopolski L, Aloia JF, Nelson ME, Pierson RN Jr, Heymsfield SB. Total body protein: a new cellular level mass and distribution prediction model. The American Journal of Clinical Nutrition 78: 979-984, 2003.

D. C. Simonson, R. A. DeFronzo. Indirect calorimetry: methodological and interpretative problems. American Journal of Physiology—Endocrinology and Metabolism Published Mar. 1, 1990 vol. 258 No. 3, E399-E412.

U.S. Final Office Action for U.S. Appl. No. 14/541,033 dated Oct. 20, 2017.

Notice of Allowance issued in ccounterpart U.S. Appl. No. 14/541,033 dated Feb. 28, 2018.

Notice of Allowance from USPTO for counterpart U.S. Appl. No. 15/905,973 dated May 28, 2020. (8 pages).

Office Action from USPTO for counterpart U.S. Appl. No. 15/905,973 dated Apr. 29, 2020. (9 pages).

Amendment filed in response to Office Action from USPTO for counterpart U.S. Appl. No. 15/905,973 dated Apr. 29, 2020, filed May 3, 2020. (11 pages)

* cited by examiner

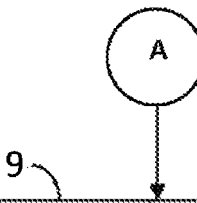

$$DP_k := \hat{D}_P \cdot \left(\frac{P_k}{P_0}\right); \quad Eq.\ 4.$$

$$DG_k := \hat{D}_G \cdot \left(\frac{G_k}{G_0}\right); \quad Eq.\ 5.$$

$$DFF_k := \frac{2}{3} \cdot \hat{D}_F \cdot \frac{F_k^{-1/3}}{F_0^{2/3}}; \quad Eq.\ 6.$$

$$DFCI_0 := \hat{D}_F \cdot (-k_L/CI_0); \quad Eq.\ 7.$$

$$DF0_k := -DFF_k \cdot F_{k-1} - DFCI_0 \cdot CI_k + \hat{D}_F \cdot \left(k_L - k_L \cdot \frac{CI_k}{CI_0} + \left(\frac{F_k}{F_0}\right)^{2/3}\right); \quad Eq.\ 8.$$

$$DF_k := DFF_k \cdot F_k + DFCI_0 \cdot CI_k + DF0; \quad Eq.\ 9.$$
$$DNLCI_0 := DFCI_0; \quad Eq.\ 10.$$
$$DNLG_k := \frac{DFF_k \cdot F_k}{G_k}; \quad Eq.\ 11.$$
$$DNL0_k := DF0_k; \quad Eq.\ 12.$$
$$DNL_k := DNLCI_0 \cdot CI_k + DNLG_0 \cdot G_k + DNL0_k; \quad Eq.\ 13.$$

$$GNGF_k := r_{GF} \cdot FI_k + r_G \cdot DF_k; \quad Eq.\ 14.$$
$$GNGPP_0 := G\hat{N}G_P \cdot \frac{\hat{D}_P}{P_0}; \quad Eq.\ 15.$$
$$GNGPCI_0 := -G\hat{N}G_P \cdot \frac{\Gamma_C}{CI_0}; \quad Eq.\ 16.$$
$$GNGPPI_0 := G\hat{N}G_P \cdot \frac{\Gamma_P}{PI_0}; \quad Eq.\ 17.$$
$$GNGP0 := G\hat{N}G_P \cdot (\Gamma_C - \Gamma_P); \quad Eq.\ 18.$$
$$GNGP_k := GNGPP_0 \cdot P_k + GNGPCI_0 \cdot CI_k + GNGPPI_0 \cdot PI_k + GNGP0; \quad Eq.\ 19.$$
$$G3P_k := r_G \cdot DF_k + r_G \cdot \Delta F_k; \quad Eq.\ 20.$$
$$RMR_k := Ec_k^* + \gamma_B \cdot M_B + \gamma_{BCM} \cdot (ICW_k + P_k + G_k - M_B) + \gamma_F \cdot F_k + (1 - \varepsilon_d) \cdot DNL_k$$
$$\qquad + (1 - \varepsilon_g) \cdot (GNGP_k + GNGF_k) + (\eta_P - \varepsilon_P) \cdot DP_k + \eta_F \cdot DF_k + \eta_G \cdot DG_k$$
$$\qquad + \eta_P \cdot \Delta P_k + \eta_F \cdot \Delta F_k + \eta_G \cdot \Delta G_k; \quad Eq.\ 21.$$
$$TEE_k^* := PAE_k' + RMR_k; \quad Eq.\ 22.$$
$$Nexcr_k := (6.25 \cdot \rho_P)^{-1} \cdot (PI_k - \rho_P \cdot \Delta P_k); \quad Eq.\ 23.$$

FIG. 5B $$DP_k := \widehat{D}_P \cdot \left(\frac{P_k}{P_0}\right); \quad Eq. 24.$$

$$DG_k := \widehat{D}_G \cdot \left(\frac{G_k}{G_0}\right); \quad Eq. 25.$$

$$DFF_k := \frac{2}{3} \cdot \widehat{D}_F \cdot \frac{F_k^{-1/3}}{F_0^{2/3}}; \quad Eq. 26.$$

$$DFCI_0 := \widehat{D}_F \cdot (-k_L/CI_0); \quad Eq. 27.$$

$$DF0_k := -DFF_k \cdot F_k - DFCI_0 \cdot CI_{k-1} + \widehat{D}_F \cdot \left(k_L - k_L \cdot \frac{CI_{k-1}}{CI_0} + \left(\frac{F_k}{F_0}\right)^{2/3}\right); \quad Eq. 28.$$

$$DF_k := DFF_k \cdot F_k + DFCI_0 \cdot CI_{k-1} + DF0_k; \quad Eq. 29.$$

$$DNLCI_0 := DFCI_0; \quad Eq. 30.$$

$$DNLG_k := \frac{DFF_k \cdot F_k}{G_k}; \quad Eq. 31.$$

$$DNL0_k := DF0_k; \quad Eq. 32.$$

$$DNL_k := DNLCI_0 \cdot CI_{k-1} + DNLG_k \cdot G_k + DNL0_k; \quad Eq. 33.$$

$$GNGF_k := r_{GF} \cdot FI_{k-1} + r_G \cdot DF_k; \quad Eq. 34.$$

$$GNGPP_0 := G\widehat{N}G_P \cdot \frac{\widehat{D}_P}{P_0}; \quad Eq. 35.$$

$$GNGPCI_0 := -G\widehat{N}G_P \cdot \frac{\Gamma_C}{CI_0}; \quad Eq. 36.$$

$$GNGPPI_0 := G\widehat{N}G_P \cdot \frac{\Gamma_P}{PI_0}; \quad Eq. 37.$$

$$GNGP0 := G\widehat{N}G_P \cdot (\Gamma_C - \Gamma_P); \quad Eq. 38.$$

$$GNGP_k := GNGPP_0 \cdot P_k + GNGPCI_0 \cdot CI_{k-1} + GNGPPI_0 \cdot PI_{k-1} + GNGP0; \quad Eq. 39.$$

$$RR_k := \gamma_B \cdot M_B + \gamma_{BCM} \cdot (ICW_k + P_k + G_k - M_B) + \gamma_F \cdot F_k - (1 - \varepsilon_d) \cdot DNL_k + (1 - \varepsilon_g)$$
$$\cdot (GNGP_k + GNGF_k) + (\eta_P - \varepsilon_P) \cdot DP_k + \eta_F \cdot DF_k + \eta_G \cdot DG_k; \quad Eq. 40.$$

$$SRMR_k := Ec_k^* + RR_k + \eta_G \cdot \Delta G_{k+1}^* + \eta_F \cdot \Delta F_{k+1}^* + \eta_P \cdot \Delta P_{k+1}^*; \quad Eq. 41.$$

$$r1_k := DNLCI_0 \cdot (1 - \varepsilon_d) + (r_G \cdot DFCI_0 + GNGPCI_0) \cdot (1 - \varepsilon_g) + \eta_F \cdot DFCI_0; \quad Eq. 42.$$

$$r2_k := r_{GF} \cdot (1 - \varepsilon_g); \quad Eq. 43.$$

$$r3_k := GNGPPI_0 \cdot (1 - \varepsilon_g); \quad Eq. 44.$$

FIG. 5C

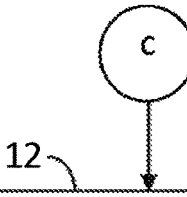

$$DP_{k-1} := \widehat{D}_P \cdot \left(\frac{P_{k-1}}{P_0}\right); \quad Eq.\ 52.$$

$$DG_{k-1} := \widehat{D}_G \cdot \left(\frac{G_{k-1}}{G_0}\right); \quad Eq.\ 53.$$

$$DFF_{k-1} := \frac{2}{3} \cdot \widehat{D}_F \cdot \frac{F_{k-1}^{-1/3}}{F_0^{2/3}}; \quad Eq.\ 54.$$

$$DFCI_0 := \widehat{D}_F \cdot (-k_L/CI_0); \quad Eq.\ 55.$$

$$DFO_{k-1} := -DFF_{k-1} \cdot F_{k-1} - DFCI_0 \cdot CI_{k-2} + \widehat{D}_F \cdot \left(k_L - k_L \cdot \frac{CI_{k-2}}{CI_0} + \left(\frac{F_{k-1}}{F_0}\right)^{2/3}\right); \quad Eq.\ 56.$$

$$DF_{k-1} := DFF_{k-1} \cdot F_{k-1} + DFCI_0 \cdot CI_{k-2} + DFO_{k-1}; \quad Eq.\ 57.$$

$$DNLCI_0 := DFCI_0; \quad Eq.\ 58.$$

$$DNLG_{k-1} := \frac{DFF_{k-1} \cdot F_{k-1}}{G_{k-1}}; \quad Eq.\ 59.$$

$$DNLO_{k-1} := DFO_{k-1}; \quad Eq.\ 60.$$

$$DNL_{k-1} := DNLCI_0 \cdot CI_{k-2} + DNLG_{k-1} \cdot G_{k-1} + DNLO_{k-1}; \quad Eq.\ 61.$$

$$GNGF_{k-1} := r_{GF} \cdot FI_{k-2} + r_G \cdot DF_{k-1}; \quad Eq.\ 62.$$

$$GNGPP_0 := \widehat{GNG}_P \cdot \frac{\widehat{D}_P}{P_0}; \quad Eq.\ 63.$$

$$GNGPCI_0 := -\widehat{GNG}_P \cdot \frac{\Gamma_C}{CI_0}; \quad Eq.\ 64.$$

$$GNGPPI_0 := \widehat{GNG}_P \cdot \frac{\Gamma_P}{PI_0}; \quad Eq.\ 65.$$

$$GNGPO := \widehat{GNG}_P \cdot (\Gamma_C - \Gamma_P); \quad Eq.\ 66.$$

$$GNGP_{k-1} := GNGPP_0 \cdot P_{k-1} + GNGPCI_0 \cdot CI_{k-2} + GNGPPI_0 \cdot PI_{k-2} + GNGPO; \quad Eq.\ 67.$$

$$RR_{k-1} := \gamma_B \cdot M_B + \gamma_{BCM} \cdot (ICW_{k-1} + P_{k-1} + G_{k-1} + ICS - M_B) + \gamma_F \cdot F_{k-1}$$
$$+ (1 - \varepsilon_d) \cdot DNL_{k-1} + (1 - \varepsilon_g) \cdot (GNGP_{k-1} + GNGF_{k-1})$$
$$+ (\eta_P - \varepsilon_P) \cdot DP_{k-1} + \eta_F \cdot DF_{k-1} + \eta_G \cdot DG_{k-1}; \quad Eq.\ 68.$$

$$SRMR_{k-1} := Ec_{k-1}^* + RR_{k-1} + \eta_G \cdot \Delta G_k^* + \eta_F \cdot \Delta F_k^* + \eta_P \cdot \Delta P_k^*; \quad Eq.\ 69.$$

$$r1_{k-1} := DNLCI_0 \cdot (1 - \varepsilon_d) + (r_G \cdot DFCI_0 + GNGPCI_0) \cdot (1 - \varepsilon_g) + \eta_F \cdot DFCI_0; \quad Eq.\ 70.$$

$$r2_{k-1} := r_{GF} \cdot (1 - \varepsilon_g); \quad Eq.\ 71.$$

$$r3_{k-1} := GNGPPI_0 \cdot (1 - \varepsilon_g); \quad Eq.\ 72.$$

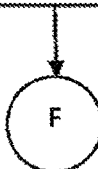

FIG. 5E

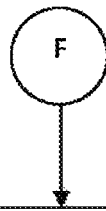

$$DP_k := \hat{D}_P \cdot \left(\frac{P_k}{P_0}\right); \quad Eq.\ 73.$$

$$DG_k := \hat{D}_G \cdot \left(\frac{G_k}{G_0}\right); \quad Eq.\ 74.$$

$$DFF_k := \frac{2}{3} \cdot \hat{D}_F \cdot \frac{F_k^{-1/3}}{F_0^{2/3}}; \quad Eq.\ 75.$$

$$DFCI_0 := \hat{D}_F \cdot (-k_L/CI_0); \quad Eq.\ 76.$$

$$DFO_k := -DFF_k \cdot F_k - DFCI_0 \cdot CI_{k-1} + \hat{D}_F \cdot \left(k_L - k_L \cdot \frac{CI_{k-1}}{CI_0} + \left(\frac{F_k}{F_0}\right)^{2/3}\right); \quad Eq.\ 77.$$

$$DF_k := DFF_k \cdot F_k + DFCI_0 \cdot CI_{k-1} + DFO_k; \quad Eq.\ 78.$$
$$DNLCI_0 := DFCI_0; \quad Eq.\ 79.$$
$$DNLG_k := \frac{DFF_k \cdot F_k}{G_k}; \quad Eq.\ 80.$$
$$DNLO_k := DFO_k; \quad Eq.\ 81.$$
$$DNL_k := DNLCI_0 \cdot CI_{k-1} + DNLG_k \cdot G_k + DNLO_k; \quad Eq.\ 82.$$
$$GNGF_k := r_{GF} \cdot FI_{k-1} + r_G \cdot DF_k; \quad Eq.\ 83.$$
$$GNGPP_0 := G\hat{N}G_P \cdot \frac{\hat{D}_P}{P_0}; \quad Eq.\ 84.$$
$$GNGPCI_0 := -G\hat{N}G_P \cdot \frac{\Gamma_C}{CI_0}; \quad Eq.\ 85.$$
$$GNGPPI_0 := G\hat{N}G_P \cdot \frac{\Gamma_P}{PI_0}; \quad Eq.\ 86.$$
$$GNGP0 := G\hat{N}G_P \cdot (\Gamma_C - \Gamma_P); \quad Eq.\ 87.$$
$$GNGP_k := GNGPP_0 \cdot P_k + GNGPCI_0 \cdot CI_{k-1} + GNGPPI_0 \cdot PI_{k-1} + GNGP0; \quad Eq.\ 88.$$
$$RR_k := \gamma_B \cdot M_B + \gamma_{BCM} \cdot (ICW_k + P_k + G_k - M_B) + \gamma_F \cdot F_k - (1 - \varepsilon_d) \cdot DNL_k$$
$$\quad + (1 - \varepsilon_g) \cdot (GNGP_k + GNGF_k) + (\eta_P - \varepsilon_P) \cdot DP_k + \eta_F \cdot DF_k$$
$$\quad + \eta_G \cdot DG_k; \quad Eq.\ 89.$$
$$SRMR_k := Ec_k^* + RR_k + \eta_G \cdot \Delta G_{k+1}^* + \eta_F \cdot \Delta F_{k+1}^* + \eta_P \cdot \Delta P_{k+1}^*; \quad Eq.\ 90.$$
$$r1_k := DNLCI_0 \cdot (1 - \varepsilon_d) + (r_G \cdot DFCI_0 + GNGPCI_0) \cdot (1 - \varepsilon_g) + \eta_F \cdot DFCI_0; \quad Eq.\ 91.$$
$$r2_k := r_{GF} \cdot (1 - \varepsilon_g); \quad Eq.\ 92.$$
$$r3_k := GNGPPI_0 \cdot (1 - \varepsilon_g); \quad Eq.\ 93.$$

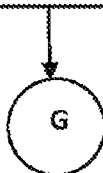

FIG. 5F

14 ─

$$\text{MMB}_{k-1} := \begin{pmatrix} 1 & 1 & 1 \\ r1_{k-1} & r2_{k-1} & r3_{k-1} \\ 0 & 0 & 1 \end{pmatrix}; \quad Eq.\ 94.$$

$$\text{MMA}^*_{k-1} := \begin{pmatrix} -TEE^*_{k-1} \\ SRMR_{k-1} - Ec^*_{k-1} - RR_{k-1} \\ -6.25 \cdot \rho_P \cdot Nexcr_{k-1} \end{pmatrix}; \quad Eq.\ 95.$$

$$\text{MMB}_k := \begin{pmatrix} 1 & 1 & 1 \\ r1_k & r2_k & r3_k \\ 0 & 0 & 1 \end{pmatrix}; \quad Eq.\ 96.$$

$$\text{MMA}^*_k := \begin{pmatrix} -TEE^*_k \\ SRMR_k - Ec^*_k - RR_k \\ -6.25 \cdot \rho_P \cdot Nexcr_k \end{pmatrix}; \quad Eq.\ 97.$$

$\text{UEI}_{k-1} := \text{MMB}_k^{-1} \cdot \text{MMB}_{k-1}; \quad Eq.\ 98.$ $\text{UBC}_{k-1} := \text{MMB}_k^{-1} \cdot \text{Mc}; \quad Eq.\ 99.$ $\text{UC}_{k-1} := \text{MMB}_k^{-1} \cdot (\text{MMA}^*_{k-1} - \text{MMA}^*_k - \text{Mc} \cdot \Delta BC^*_k); \quad Eq.\ 100.$ <u>Linear Model of the Utilized Energy Intake (LM-UEI):</u>
$EI_k = \text{UEI}_{k-1} \cdot EI_{k-1} + \text{UBC}_{k-1} \cdot \Delta BC^*_{k+1} + \text{UC}_{k-1}; \quad Eq.\ 101.$ <u>Measurement Model of the Utilized Energy Intake (M-UEI):</u>
$EI_k^{RRE*} = \text{MMB}_k^{-1} \cdot \text{Mc} \cdot \Delta BC^*_{k+1} - \text{MMB}_k^{-1} \cdot \text{MMA}^*_k; \quad Eq.\ 102.$

15 ─

STOCHASTIC IDENTIFICATION WITH INNOVATIONS REPRESENTATION
<u>Self Correcting Model of the Utilized Energy Intake (S-EI):</u>

If M-UEI is used:
$\delta \widehat{EI}^*_k := \text{MMB}_k^{-1} \cdot \text{Mc} \cdot \Delta BC^*_{k+1} - \text{MMB}_k^{-1} \cdot \text{MMA}^*_k - \widehat{EI}^*_{k-1}; \quad Eq.\ 103$ If trajectory is used:
$\delta \widehat{EI}^*_k := \text{MMB}_k^{-1} \cdot \text{Mc} \cdot \Delta BC^{TR*}_{k+1} - \text{MMB}_k^{-1} \cdot \text{MMA}^*_k - \widehat{EI}^*_{k-1}; \quad Eq.\ 104.$ $\widehat{EI}^*_k := \text{UEI}_{k-1} \cdot \widehat{EI}^*_{k-1} + \text{UBC}_{k-1} \cdot \Delta BC^*_{k+1} + \text{UC}_{k-1} + \text{KU}_k \cdot \delta \widehat{EI}^*_k; \quad Eq.\ 105.$ $EI_k := \widehat{EI}^*_k; \quad Eq.\ 106.$

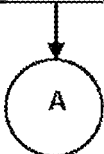

$$He := \begin{pmatrix} \frac{1}{Hc \cdot co} & \frac{1}{Hf \cdot fo} & \frac{1}{Hp \cdot po} \\ \varrho_C & \varrho_F & \varrho_P \\ 0 & 0 & \frac{Hp \cdot po}{\varrho_P} \end{pmatrix}; \quad Eq.\ 107.$$

$$HEE_k^* := \begin{pmatrix} TEE_k^* - \hat{\varphi}_k \\ TEE_k^* - \hat{\varphi}_k \\ 6.25 \cdot \rho_P \cdot Nexcr_k - GNGP_k \end{pmatrix}; \quad Eq.\ 108.$$

Measurement Model of the Macronutrient Oxidation Rates (M-Ox):

$$Ox_k^* := He^{-1} \cdot HEE_k^*; \quad Eq.\ 109.$$

$$\begin{pmatrix} CarbOx_k^* \\ FatOx_k^* \\ ProtOx_k^* \end{pmatrix} := Ox_k^*; \quad Eq.\ 110.$$

17

PROCESS MODEL
Linear Extended Model of the Human Energy Metabolism (LEM-HEM):

$$\rho_C \cdot \Delta G_{k+1} := CI_k + \hat{v}_k \cdot GNGP_k + GNGF_k - \hat{\mu}_k \cdot DNL_k - G3P_k - EFs_k - CarbOx_k^* - \hat{\varphi}_k; \quad Eq.\ 111.$$

$$\rho_F \cdot \Delta F_{k+1} := r_{FFA} \cdot FI_k + \hat{\mu}_k \cdot DNL_k + r_G \cdot \Delta F_{k+1} - FatOx_k^*; \quad Eq.\ 112.$$

$$\rho_P \cdot \Delta P_{k+1} := PI_k - \hat{v}_k \cdot GNGP_k - ProtOx_k^*; \quad Eq.\ 113.$$

$$\Delta BC_{k+1} := A_k \cdot BC_k + B_k \cdot EI_k + C_k; \quad Eq.\ 114.$$

M-FLP  18  Choice between M-FLP or M-FLR  M-LFR

H  I (AC4)

606

Individualized estimation of $\hat{\varrho}_{L_k}$ and $\hat{\varrho}_{F_k}$ is as follows:

$$\mathbf{DL}'_k \approx \mathbf{DIO}'_k \cdot \hat{A}_k; \quad Eq.\,215$$
$$\mathbf{DF}'_k \approx \mathbf{DIO}'_k \cdot \hat{B}_k; \quad Eq.\,216$$

where $$\mathbf{DIO}'_k = \begin{pmatrix} MEI'_0 - TEE'_0 \\ \vdots \\ MEI'_k - TEE'_k \end{pmatrix}; Eq.\,217, \quad \mathbf{DL}'_k = \begin{pmatrix} \Delta L'_1 \\ \vdots \\ \Delta L'_{k+1} \end{pmatrix}; Eq.\,218, \quad \mathbf{DF}'_k = \begin{pmatrix} \Delta F'_1 \\ \vdots \\ \Delta F'_{k+1} \end{pmatrix} Eq.\,219;$$

The least square estimator of $\hat{A}_k$ and $\hat{B}_k$ is:

$$\hat{A}_k = \left(\mathbf{DIO}'^T_k \cdot \mathbf{DIO}'_k\right)^{-1} \cdot \mathbf{DIO}'^T_k \cdot \mathbf{DL}'_k; \quad Eq.\,220a$$
$$\hat{B}_k = \left(\mathbf{DIO}'^T_k \cdot \mathbf{DIO}'_k\right)^{-1} \cdot \mathbf{DIO}'^T_k \cdot \mathbf{DF}'_k; \quad Eq.\,220b$$

I prefer using the data-recursive least square as the parameters $\hat{A}_k$ and $\hat{B}_k$ are slowly drifting.

$$\hat{A}_k = \hat{A}_{k-1} + KA_k \cdot \left(\hat{A}_{k-1} - \hat{A}^*_k\right); \quad Eq.\,221$$
$$\hat{B}_k = \hat{B}_{k-1} + KB_k \cdot \left(\hat{B}_{k-1} - \hat{B}^*_k\right); \quad Eq.\,222$$

where $\hat{A}^*_k = \dfrac{\Delta L'_{k+1}}{MEI'_k - TEE'_k}$; $Eq.\,223$, and $\hat{B}^*_k = \dfrac{\Delta L'_{k+1}}{MEI'_k - TEE'_k}$; $Eq.\,224$.

$$\varrho^*_{F_k} = \begin{cases} \varrho_F + 0.178 \dfrac{Kcal}{gram} & \text{if } \Delta \hat{F}_k > 0; \quad Eq.\,225a \\ \varrho_F & \text{if } \Delta \hat{F}_k \leq 0; \quad Eq.\,225b \end{cases}$$

$$\varrho^*_{L_k} = \dfrac{1 - \varrho^*_{F_k} \cdot \hat{A}_k}{\hat{B}_k}; \quad Eq.\,226$$

I prefer using the data-recursive least square as the parameters $\hat{\varrho}_{F_k}$ and $\hat{\varrho}_{L_k}$ are slowly drifting.

$$\hat{\varrho}_{F_k} = \hat{\varrho}_{F_{k-1}} + K\varrho_{F_k} \cdot \left(\hat{\varrho}_{F_{k-1}} - \varrho^*_{F_k}\right); \quad Eq.\,227$$
$$\hat{\varrho}_{L_k} = \hat{\varrho}_{L_{k-1}} + K\varrho_{L_k} \cdot \left(\hat{\varrho}_{L_{k-1}} - \varrho^*_{L_k}\right); \quad Eq.\,228$$

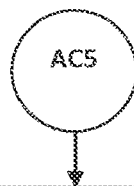

607

Gluconeogenesis from protein is calculated here as:

$GNGPP_0 := G\widehat{N}G_P \cdot \frac{\widehat{D}_P}{P_0}$;  Eq. 229

$GNGPCl_0 := -G\widehat{N}G_P \cdot \frac{\Gamma_C}{Cl_0}$;  Eq. 230

$GNGPPl_0 := G\widehat{N}G_P \cdot \frac{\Gamma_P}{Pl_0}$;  Eq. 231

$GNGP0 := G\widehat{N}G_P \cdot (\Gamma_C - \Gamma_P)$;  Eq. 232

$GNGP_k := GNGPP_0 \cdot P_k + GNGPCl_0 \cdot Cl_{k-1} + GNGPPl_0 \cdot Pl_{k-1} + GNGP0$;  Eq. 233.

608

Calculation of macronutrient oxidation rates is as follows:

$ProtOx_k^* = Pl_k - GNGP_k - \varrho_P \cdot \Delta P_{k+1}^{*\prime}$; Eq. 234 where $\Delta P_{k+1}^{*\prime} = 0.25 \cdot (\Delta L_{k+1}^\prime - \Delta ECW_{k+1}^\prime)$; Eq. 235

$FatOx_k^* = \frac{\widehat{\varrho}_{F_k}}{\widehat{\varrho}_{L_k} \cdot \widehat{R}_k + \widehat{\varrho}_{F_k}} \cdot TEE_k^\prime$; Eq. 236

$CarbOx_k^* = TEE_k^\prime - FatOx_k^* - ProtOx_k^*$; Eq. 237

609

The estimation of parameter for energy flux from carbohydrate pool to fat pool $\hat{\sigma}_k$ is as follows:

$\hat{\sigma}_k = \hat{\sigma}_{k-1} + K\sigma_k \cdot (\sigma_k - \sigma_k^*)$; Eq. 238 where $\sigma_k^* = \frac{TEE_k}{TEE_{k-1}} \cdot FatOx_{k-1} - r_{FFA} \cdot Fl_k - \widehat{\varrho}_{F_k} \cdot \Delta \widehat{F}_k$; Eq. 239

613 —
The Canonical Model Form of the Human Energy Metabolism (C-HEM) is as follows:

$$L_{k+1} = L_k + \frac{R_k}{\varrho_{L_k} \cdot R_k + \varrho_{F_k}} \cdot (CI_k + FI_k + PI_k - TEE_k); \quad Eq.\ 252$$

$$F_{k+1} = F_k + \frac{1}{\varrho_{L_k} \cdot R_k + \varrho_{F_k}} \cdot (CI_k + FI_k + PI_k - TEE_k); \quad Eq.\ 253$$

$$P_{k+1} = P_k + \frac{1}{\varrho_P} \cdot (PI_k - GNGP_k - ProtOx_k^*); \quad Eq.\ 254.$$

614 —
The estimator equation of the canonical model form of the human energy metabolism is as follows:

$$\hat{L}_{k+1} = \hat{L}_k + \frac{1}{\hat{\varrho}_{L_k}} \cdot (CI_k + r_{GF} \cdot FI_k + PI_k - \hat{\sigma}_k + \hat{\omega}_k - CarbOx_k^* - ProtOx_k^* + K_{L_k} \cdot \delta L_k); \quad Eq.\ 255$$

$$\hat{F}_{k+1} = \hat{F}_k + \frac{1}{\hat{\varrho}_{F_k}} \cdot (r_{FFA} \cdot FI_k + \hat{\sigma}_k - FatOx_k^* + K_{F_k} \cdot \delta P_k); \quad Eq.\ 256$$

$$\hat{P}_{k+1} = \hat{P}_k + \frac{1}{\varrho_P} \cdot (PI_k - GNGP_k - ProtOx_k^* + K_{P_k} \cdot \delta P_k); \quad Eq.\ 257$$

The inverse calculation of food intake using trajectory values of the body composition changes $\Delta L_{k+1}^{*TR}$, $\Delta F_{k+1}^{*TR}$, and $\Delta P_{k+1}^{*TR}$ using matrix notation is as follows:

$$\begin{pmatrix} \widehat{CI}_k \\ \widehat{FI}_k \\ \widehat{PI}_k \end{pmatrix} = \begin{pmatrix} 1 & r_{GF} & 1 \\ 0 & r_{FPA} & 0 \\ 0 & 0 & 1 \end{pmatrix}^{-1} \cdot \left[ \begin{pmatrix} \widehat{\varrho}_{L_k} \cdot \Delta L_{k+1}^{*TR} \\ \widehat{\varrho}_{F_k} \cdot \Delta F_{k+1}^{*TR} \\ \varrho_P \cdot \Delta P_{k+1}^{*TR} \end{pmatrix} + \begin{pmatrix} \dfrac{\widehat{\varrho}_{L_k} \cdot \widehat{R}_k}{\widehat{\varrho}_{L_k} \cdot \widehat{R}_k + \widehat{\varrho}_{F_k}} \cdot TEE_k' \\ \dfrac{\widehat{\varrho}_{F_k}}{\widehat{\varrho}_{L_k} \cdot \widehat{R}_k + \widehat{\varrho}_{F_k}} \cdot TEE_k' \\ 6.25 \cdot \varrho_P \cdot Nexcr_k^{*'} \end{pmatrix} \right]; \; Eq.\,258$$

where $6.25 \cdot \varrho_P \cdot Nexcr_k^{*'} = PI_k' - \varrho_P \cdot \Delta P_{k+1}^{*'}$; $Eq.\,259$

44 —

( Proceed to next day )

Part three: Stage 3:

$$SBC = \sum_{i=1}^{N} w_i \cdot |Z_i^* - Z_i^M|^2 + \lambda_2 \cdot h_2 \quad Eq.\,351$$

$$\gamma LT = L_j/TBW_j^* = 1.366 \quad Eq.\,352$$
$$\gamma LI = LCM_j/ICW_j^* = 1.4286 \quad Eq.\,353$$
$$\gamma PL = P_j/LCM_j = 0.25 \quad Eq.\,354$$
$$\gamma BM = W_j/BM_j = 0.04 \quad Eq.\,355$$
$$\gamma ECP = (ECP_j - 0.732 \cdot BM_j)/ECW_j^* = 0.01087 \quad Eq.\,356$$
$$\Delta L_k = \gamma LT \cdot TBW_k^* - L_j = \quad Eq.\,357$$

$$\Delta P_k = P_k - P_j = \gamma PL \cdot \gamma LI \cdot ICW_k^* - P_j \quad Eq.\,358$$

$$\Delta G_k = \frac{\varrho_L}{\varrho_G} \cdot \Delta L_k - \frac{\varrho_P}{\varrho_G} \cdot \Delta P_k = \frac{\varrho_L}{\varrho_G} \cdot \gamma LT \cdot TBW_k^* - \gamma PL \cdot \gamma LI \cdot \frac{\varrho_P}{\varrho_G} \cdot ICW_k^* - \frac{\varrho_L}{\varrho_G} \cdot L_j + \frac{\varrho_P}{\varrho_G} \cdot P_j$$

$$Eq.\,359$$

$$G_k = \Delta G_k + G_j \quad Eq.\,360$$

$$ICS = (\gamma LI - \gamma PL \cdot \gamma LI - 1) \cdot ICW_j^* - G_j \quad Eq.\,361$$

$$BM = \gamma BM \cdot W_j^* \quad Eq.\,362$$

$$ECP_k = 0.732 * BM + \gamma ECP \cdot ECW_j^* \quad Eq.\,363$$

$$P_k = \gamma PL \cdot \gamma LI \cdot ICW_k^* \quad Eq.\,364$$

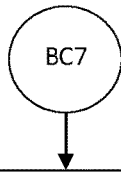

715

$$L_k = ECW_k^* + ICW_k^* + ECP_k + P_k + G_k + ICS + BM \quad Eq. 365$$

$$L_k = \gamma LT \cdot ECW_k^* + \gamma LT \cdot ICW_k^* \quad Eq. 366$$

$$h_2 := ECW_k^* + ICW_k^* + ECP_k + P_k + G_k + ICS + BM - \gamma LT \cdot ECW_k^* - \gamma LT \cdot ICW_k^* = 0$$

$$Eq. 367$$

$$h_2 := ECW_k^* \cdot \left(1 - \gamma LT + \gamma ECP + \frac{\varrho_L}{\varrho_G} \cdot \gamma LT\right) +$$

$$+ ICW_k^* \cdot \left(1 - \gamma LT + \gamma PL \cdot \gamma LI + \frac{\varrho_L}{\varrho_G} \cdot \gamma LT - \gamma PL \cdot \gamma LI \cdot \frac{\varrho_P}{\varrho_G}\right) +$$

$$(\gamma LI - \gamma PL \cdot \gamma LI - 1) \cdot ICW_j^* + 1.732 \cdot BM - \frac{\varrho_L}{\varrho_G} \cdot L_j + \frac{\varrho_P}{\varrho_G} \cdot P_j = 0$$

$$Eq. 368$$

$$h_2 := kECW_j^* \cdot \left(\frac{H^2 \cdot \sqrt{W_k}}{R_0}\right)^{2/3} \cdot \left(1 - \gamma LT + \gamma ECP + \frac{\varrho_L}{\varrho_G} \cdot \gamma LT\right) +$$

$$+ kICW_j^* \cdot \left(\frac{H^2 \cdot \sqrt{W_k}}{R_\infty}\right)^{2/3} \cdot \left[\gamma LI - \gamma LT + \gamma PL \cdot \gamma LI + \frac{\varrho_L}{\varrho_G} \cdot \gamma LT - \gamma PL \cdot \gamma LI \cdot \frac{\varrho_P}{\varrho_G}\right] +$$

$$(\gamma LI - \gamma PL \cdot \gamma LI - 1) \cdot ICW_j^* + 1.732 \cdot BM - \frac{\varrho_L}{\varrho_G} \cdot L_j + \frac{\varrho_P}{\varrho_G} \cdot P_j = 0$$

$$Eq. 369$$

$$ECW_k^{BC'} := kECW_j^* \cdot \left(\frac{H^2 \cdot \sqrt{W_k}}{R_0^{BC'}}\right)^{2/3} \quad ; \quad Eq. 370$$

$$ICW_k^{BC'} := kICW_j^* \cdot \left(\frac{H^2 \cdot \sqrt{W_k}}{R_\infty^{BC'}}\right)^{2/3} \quad ; \quad Eq\ 371$$

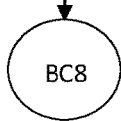

SYSTEMS AND METHODS FOR HIGH FREQUENCY IMPEDANCE SPECTROSCOPY DETECTION OF DAILY CHANGES OF DIELECTRIC PROPERTIES OF THE HUMAN BODY TO MEASURE BODY COMPOSITION AND HYDRATION STATUS

CROSS REFERENCE

This is a divisional patent application of U.S. patent application Ser. No. 15/673,092, filed on Aug. 9, 2017, and titled SYSTEMS AND METHODS FOR HIGH FREQUENCY IMPEDANCE SPECTROSCOPY DETECTION OF DAILY CHANGES OF DIELECTRIC PROPERTIES OF THE HUMAN BODY TO MEASURE BODY COMPOSITION AND HYDRATION STATUS, which claims priority to U.S. patent application Ser. No. 14/541,033, filed on Nov. 13, 2014, and titled AN APPARATUS AND METHOD FOR THE ANALYSIS OF THE CHANGE OF BODY COMPOSITION AND HYDRATION STATUS AND FOR DYNAMIC INDIRECT INDIVIDUALIZED MEASUREMENT OF COMPONENTS OF THE HUMAN ENERGY METABOLISM, which claims priority to U.S. Provisional Application Ser. No. 62/372,363, filed on Aug. 9, 2016, and titled APPARATUS AND METHOD FOR ANALYSIS OF BODY COMPOSITION AND HYDRATION STATUS AND DYNAMIC INDIRECTED INDIVIDUALIZED MEASUREMENT OF COMPONENTS OF THE HUMAN ENERGY METABOLISM, the disclosures of which are incorporated herein by reference in their entireties.

TECHNICAL FIELD

Embodiments described herein relate to the analysis of body composition and hydration status and dynamic indirect individualized measurement of components of the human energy metabolism. More particularly, embodiments described herein relate to the analysis of body composition and hydration status and individualized mathematical modeling of the human energy metabolism relates generally to the measurement of the resistance and reactance of the human subject, to fitting mathematical models to serial measurements of indirectly measured lean body mass and fat mass, and to performing minimum variance estimation and prediction of variable of the human energy metabolism.

BACKGROUND

Biomedical engineering tools and multiple patented inventions of bioimpedance spectroscopy have been concerned with the problems of measuring the resistance and reactance of the human body at a multitude of frequencies in order to determine body composition and hydration status. Advancements in mathematical modeling of the human energy metabolism have provided tools to describe the relationship between energy balance, which is the difference of the energy intake and the total energy expenditure, and body composition changes. State space modeling coupled with the use of time variant minimum variance Kalman filtering or prediction has been successfully used in control engineering for over 50 years to observe and control state variables of complex dynamic systems. This technology holds great potential in monitoring difficult to measure daily body composition changes along with other essential components of the human energy metabolism in order to maximize capabilities of controlling them.

Bioimpedance spectroscopy has become a widely used technique in body composition and hydration status analysis in recent decades. The measurement of impedance, which is measuring resistance and reactance at frequencies from 1 to 1000 kHz, is purported to assist in the determination of extracellular and intracellular water mass. According to the Cole model of body impedance as interpreted by Cornish[1], a current at low frequency flows through the extracellular water mass while at higher frequencies it flows through both the extracellular and intracellular water mass, allowing for extracellular and total water mass measurements. The Cole model fitted to resistances and reactances of the human subject at various frequencies can be extrapolated to the resistance values at zero and infinite frequencies. Using the resistance values at zero and an extrapolated infinite frequency, Moissl developed equations corrected with body mass index to calculate extracellular and intracellular water mass.[2] The problem with Moissl's equations was that they contained errors in the references, which accounted for the errors in the body mass index corrected extracellular and intracellular water mass calculation's accuracy.[3]

[1] Cornish, DOI: 10.1088/0031-9155/38/3/001
[2] Moissl, DOI: 10.1088/0967-3334/27/9/012
[3] Id.

The errors in bioimpedance measurements of extracellular and intracellular water have hampered their accuracy and reliability. When using bioimpedance instruments, artefactual errors occur everywhere along the path of the flowing current around the entire electric circuit, which consists of current sources, a human subject, measurement electrodes, cable connections from subject to measuring instrument, and calibration elements. One example of a disadvantage of the prior art is that the errors due to offset voltage and voltage noise at nodal junction points of the circuit elements cannot be determined, analyzed, and mitigated.[4]

[4] U.S. Pat. No. 5,280,429 (1994).

Moreover, at higher frequencies in bioimpedance spectroscopy, unexpected phase shifts in the results occur due to human subject stray capacitance and the instrument introduces distortions in the results due to nonlinearity. Errors due to stray capacitance are unavoidable in practice, uncontrollable to a large degree, and likely to be more pronounced where other devices are also attached to the subject, but they are measurable. An example of a disadvantage of the prior art is that the errors due to stray capacitances and other measuring errors are neither determined, nor analyzed, nor reduced.[5]

[5] Id.

Another problem with the current bioimpedance spectroscopy technology is the variation in measurement results among machines due to the systemic errors introduced by the techniques, the instrumentation used, and other errors. Another example of the disadvantage of the prior art is that no effort was made to measure quality and inform the user about the size of the detectable error during measurement and about the reliability of the measurement results.[6]

[6] Id.

Another problem with bioimpedance measurements could be the placement of the preamplifier and the drivers of the shielded cables far away from the sensing electrodes. The disadvantage of such arrangements is that the magnitude of the interference from outside electromagnetic sources and the capacitive load from the shielded cables could cause suboptimal results. The prior art uses Fast Fourier Transformation, substituting summation for integration and evaluating only two wavelengths.[7] These simplifications would be allowed if the analog to digital conversation were accurate, which it is not.

[7] Id.

With regard to measuring variable of human energy metabolism, decades of research into the causes of the obesity epidemic and related scientific research for the cause of it led to the creation of mathematical models of obesity. These models were based on the first law of thermodynamics and proffered that imbalance between energy intake and energy expenditure lead to changes in energy storage, primarily in lipids. The effort to quantify changes of the lipid store led Hall to construct mathematical models describing body composition changes matched to group averages.[8] However, everyone's metabolism has unique characteristics, and individualized modeling is needed. Further, there is a need for real-time metabolic modeling and tracking. The Hall models[9] work off line when all data are available for retrospective analysis. Differential equations with infinitesimal time resolution are used in the Hall models, requiring significant software capacity to solve and knowledge of how the system changes during the 24 hour time period, when neither is needed for real-time use and for measuring changes every 24 hour period. Importantly, the Hall model equations do not succeed in satisfying the constraint of conservation of energy (i.e. the First Law of Thermodynamics), at the end of each day, which is essential for individualized real-time modeling. Further, Hall does not consider the constraint that the model calculated body composition with its daily change together with changes of hydration status have to add up to the measured body weight and its daily change to allow for individualized real-time modeling.

[8] Hall, DOI: 10.1152/ajpendo.00523; DOI: 10.1109/MEMB.2009.935465; DOI: 10.1152/ajpendo.00559.2009

[9] Hall, DOI: 10.1152/ajpendo.00523; DOI: 10.1152/ajpendo.00559.2009

The imprecision of current methods for determining the variable associated with body composition change, energy expenditure, and energy intake have precluded accurate quantification of the energy balance and thus precluded definitive statements regarding the cause of the obesity epidemic. The currently accepted method for tracking calorie intake in scientific studies of energy balance is self-reported calorie intake counting. For example, the daily ingested calories broken down into the three macronutrient groups are needed every day for the calculations in the Hall models. However, self-reported calorie intake counting is fraught with systemic errors.[10]

[10] Hebert, DOI: 10.1016/S1047-2797(01)00297-6

Model calculations of the macronutrient oxidation rate are an essential component of the modeling of the human energy metabolism. Hall created models for the macronutrient oxidation rates.[11] However, Hall's equations are ad-hoc and are inherently nonlinear and not suitable for inverse calculations when model input is sought from known model output.

[11] Hall, DOI: 10.1152/ajpendo.00523; DOI: 10.1152/ajpendo.00559.2009

The problems of prediction and noise filtering also exist in the dynamic modeling of the metabolism. The estimation or prediction of the state variables of a dynamic system model poses the challenges of ensuring accuracy and stability of estimations. Therefore, there is a need for accurate and simplified tracking of body composition change, energy expenditure, and especially energy intake exists.

With current clinical trial usage of the bioelectrical impedance measurement method, it has become quite apparent that there are several shortcomings in clinical applications of the method. Some of the concerns of clinical applications are summarized in Buchholtz[12] et al. Currently, the clinical applicability and the measurement accuracy are limited to the group level only rather than providing accurate values specific to an individual. The various bioelectrical impedance models and reference methods differ widely across studies. The results are confusing for a clinician and they break down in disease states.

[12] Buchholtz et al, DOI: 10.1177/0115426504019005433

There is no consensus on which commercially available biomedical impedance instruments are the best and which electrophysiological models best describe the human body in vivo. Some of the shortcomings of the current instrumentation include but are not limited to: lack of quality measurements of the electrode placement and electrical properties of electrodes during measurements, lack of error calculations, no elimination of flawed data, no error calculations for the model fitting, no overall quality measurements regarding results, and no use of statistical improvement of errors when serial measurements are taken from an individual.

Currently, there is no systematic effort to register important but influencing factors on the measurements such as environmental factors including location and room temperature to measure and compensate for local environmental electromagnetic influences. There is no systematic effort to register physiological factors such as accurate body weight, time of the measurement, duration of measurement, skin temperature, recent exercise status, fluid and food consumption diary, timing of last bladder emptying, and bowel movement among others.

The simplistic use of the Cole model is inadequate to capture important changes regarding conductivity and permittivity[13] which occur during acute changes of hydration. The impedance models currently in use fail to predict changes of extracellular water and total body water during short term 2-3% dehydration and rehydration.[14] The Cole model is not individualizable to suit current demand.

[13] Gerritsen et al, DOI:10.1088/1742-6596/434/1/012005

[14] Asselin et al, DOI: 10.1016/S0969-8043(97)00179-6

The problems of measuring hydration status changes with current bioimpedance methods carry over to the problem of measuring body composition changes. The current methods of measuring body composition changes with the bioimpedance spectroscopy method rely primarily on the determination of extracellular as well intracellular water masses.

Current bioimpedance spectroscopy methods revealed significant systematic errors in the difference between fluid volumes and the reference in the extremes of body mass index.[15] These significant systematic errors are due to large variations of the calculated resistances at zero and infinite frequencies, suggestive of the inadequacy of the applied Hanai mixture theory applied together with the Cole model to describe human immittance.

[15] Moissl, DOI: 10.1088/0967-3334/27/9/012

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

Disclosed herein are systems and methods for high frequency impedance spectroscopy detection of daily changes of dielectric properties of the human body to measure body composition and hydration status. According to an aspect, a method at a computing device to determine a set of indirect dynamic human metabolism parameters includes using a sensor on an individual to acquire a set of electrical measurements. The method also includes combining a ratio technique with a canonical model form technique. The also includes performing a series of mathematical calculations on the acquired set of electrical measurements to determine the set of indirect dynamic human metabolism parameters for the individual based on the combined ratio technique and the canonical model form technique. The method further includes generating a trend regarding the set of indirect dynamic human metabolism parameters in response to performing the series of mathematical calculations on the acquired set of electrical measurements to determine the set of indirect dynamic human metabolism parameters for the individual.

BRIEF DESCRIPTION OF THE DRAWINGS

The foregoing summary, as well as the following detailed description of various embodiments, is better understood when read in conjunction with the drawings provided herein. For the purposes of illustration, there is shown in the drawings exemplary embodiments; however, the presently disclosed subject matter is not limited to the specific methods and instrumentalities disclosed.

FIGS. 7A, 7B, 7C, 7D, 7E, 7F, 7G, 7H, and 7I show the flowcharts of the operation with three parts wherein the first part contains three stages, the second part two stages, and the third part three stages of operation.

DETAILED DESCRIPTION

Figure 1A:
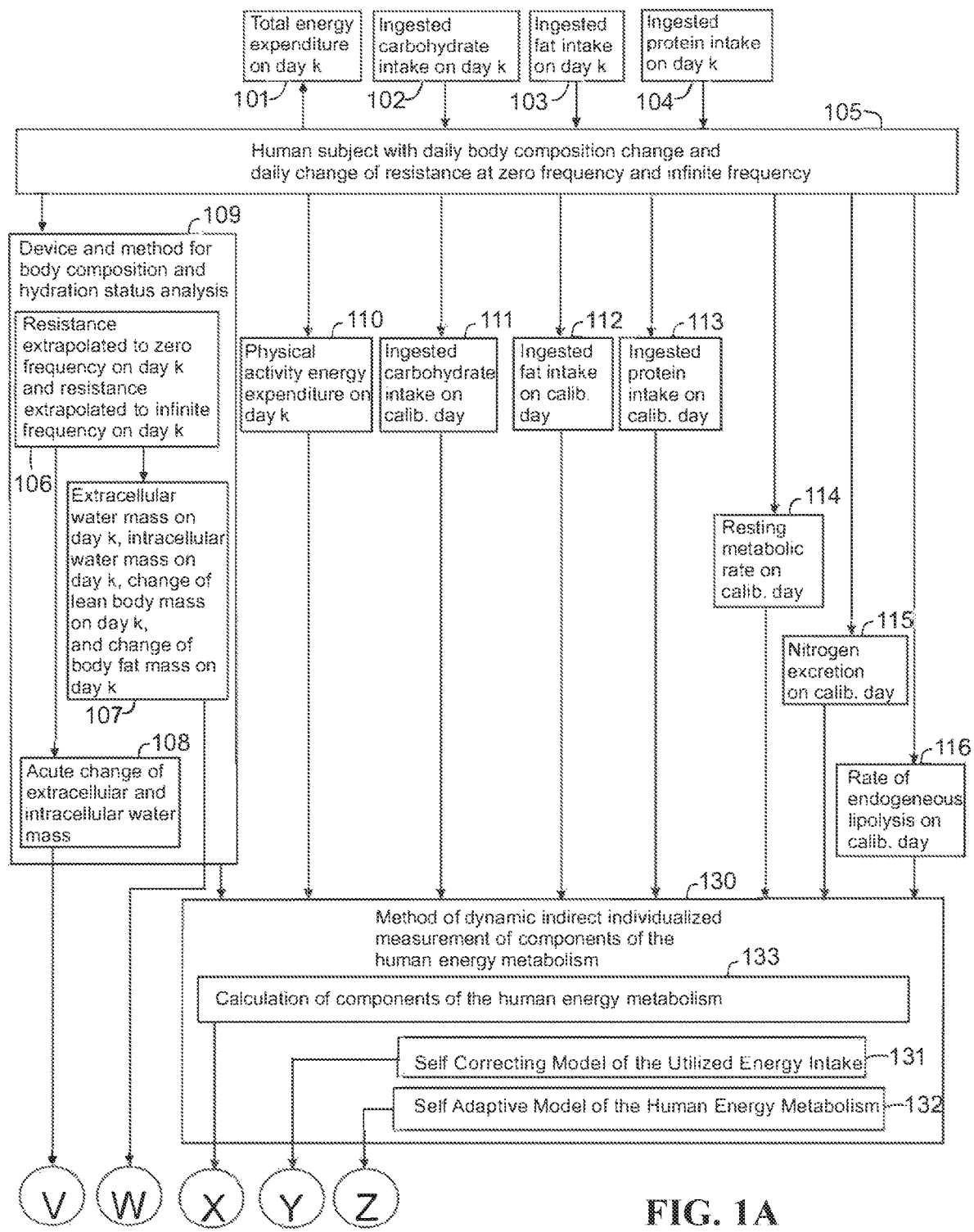
FIGS. 1A and 1B depict flowcharts illustrating how the measurements of a device for body composition and hydration status analysis flow into a method for dynamic indirect individualized measurement of components of the human energy metabolism.

The presently disclosed subject matter is described with specificity to meet statutory requirements. However, the description itself is not intended to limit the scope of this patent. Rather, the inventor has contemplated that the claimed subject matter might also be embodied in other ways, to include different steps or elements similar to the ones described in this document, in conjunction with other present or future technologies. Moreover, although the term "step" may be used herein to connote different aspects of methods employed, the term should not be interpreted as implying any particular order among or between various steps herein disclosed unless and except when the order of individual steps is explicitly described.

Articles "a" and "an" are used herein to refer to one or to more than one (i.e. at least one) of the grammatical object of the article. By way of example, "an element" means at least one element and can include more than one element.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 1%, 0.5%, 0.1%, 0.05%, or 0.01% of the stated value. Unless otherwise clear from context, all numerical values provided herein are modified by the term about.

Unless otherwise defined, all technical terms used herein have the same meaning as commonly understood by one of ordinary skill in the art to which this disclosure belongs.

According to one or more aspects, several advantages of the analysis of change of body composition and hydration status over the prior art include, but are not limited to:
1. Measuring and correcting for stray capacitance.
2. Positioning the preamplifiers and the shield drivers close to the sensing electrodes.
3. Analyzing and removing errors and noise in the measuring circuit by using an input logic circuit.
4. Possessing a current source designed for high output resistance and low output reactance.
5. Using a sine wave fitting algorithm.
6. Using a non-linear curve fitting algorithm.
7. Creating individualized references for the measurement of body composition and hydration status change.

Regarding measuring and correcting for stray capacitance, one aspect measures all capacitances including stray capacitances. One aspect measures the voltage at 6 measuring points along the current path. One aspect applies Kirchhoff's first and second rule and Ohm's rule. All measurements have amplitude, offset, and phase value and one aspect compares them to the zero phase value measured at reference resistances. The advantage of measuring voltage at nodal junctions and applying Kirchhoff's rules and Ohm's rule is that it is possible to calculate the stray capacitance and measure its influence on the results.

Regarding positioning the preamplifiers and the shield drivers close to the sensing electrodes, the advantage of one aspect is positioning the preamplifiers and the shield drivers close to the sensing electrodes so that the input noise will be kept low and no additional noise or capacitive load will be added.

Regarding analyzing and removing errors and noise in the measuring circuit by using an input logic circuit, one aspect use switches to isolate or short circuit or leave intact parts of the measuring circuit without or with excitation at various frequencies. This allows for determining errors due to offset voltage and voltage noise due to various sources. The offset voltage is eliminated by subtracting the measured values at nodal junctions from the measured signal via a software algorithm. Hardware and/or software filtering remove voltage noise. One advantage of using an input logic circuit is that the apparatus will sense the offset voltage and voltage noise in the environment of operation and this allows for reduction of offset voltage and voltage noise.

Regarding a current source designed for high output resistance and low output reactance, one aspect uses two mirrored Howland current sources which are fine tuned for their passive components to achieve high output resistance and low output reactance.[16] This mirrored arrangement has the advantage that the output reactance is cut in half. One aspect uses two reference resistances for each current source. Using two reference resistances for each current source has one advantage such that the current generated or sunk into the circuit will be known for each current source, allowing for precise network analysis. Using two mirrored Howland current sources has another advantage of creating a virtual floating earth potential, avoiding electric charge build up on the sensing electrodes.

[16] Bertemes-Filho, DOI:10.4236/cs.2013.47059

Regarding use of a sine wave fitting algorithm, sine wave fitting has the advantage of providing a priori knowledge of the exact value of the applied frequency of excitation, reducing the number of unknown variables. In statistical terms, sine fitting provides the minimum variance linear estimation for amplitude, phase, and offset. Sine fitting compensates better for the errors of the analog digital conversion than the Fast Fourier Transformation, which remains sensitive to such errors.[17] Using a sine wave fitting algorithm over 6 to 16 wavelengths minimizes sampling error of the analog to digital converter. The sine fitting algorithm also gives a residual value, which one aspect uses to measure quality. One advantage of using the sine fitting algorithm is better overall noise reduction, allowing for elimination of offset voltage, minimization of voltage noise, and the ability to measure quality.

[17] Bertocco, DOI:10.1109/19.571881

Regarding using a non-linear curve fitting algorithm, a Cole model with unknown resistance at zero and an extrapolated infinite frequency and unknown membrane capacitance may be fitted to the resistance and reactance values at each examined frequency. The residual value, calculated as the difference between the measured and the model predicted value, may be used to measure the quality of each individual measurement at each frequency. The sum of squared residual values thus measures the overall performance of the first embodiment of one aspect of the apparatus. The advantage of measuring performance using the sum of squared residual values is that the user obtains quantified information of performance and of reliability of the function of the apparatus.

Regarding creating individualized references for the measurement of body composition and hydration status change, one aspect overcomes the problem that the equations corrected with body mass index contain errors in the references by establishing individual references for extracellular and intracellular water mass. One advantage of creating individualized references is that all of my measurements are individualized, referenced to individual reference values.

According to one or more aspects, several advantages of dynamic indirect individualized measurement of components of the human energy metabolism over the prior art include, but are not limited to:
1. Having an individualized self-correction and self-adaptive modeling.
2. Having a real-time calculation with recursive formulas and daily updates.
3. Applying linear invertible models.
4. Using difference equations.
5. Having a state space method.
6. Calculating macronutrient oxidation rates.
7. Calculating daily utilized macronutrient intake values from ingested macronutrient calorie intake.
8. Using the law of conservation of energy.
9. Estimating the daily utilized macronutrient intake values from indirectly measured body composition changes.
10. Estimating the daily changes of the body composition and stochastic identification of the unidentified energy losses or gains, correction factor of the de novo lipogenesis, and correction factor for gluconeogenesis.
11. Deriving the Canonical Model Form of the Human Energy Metabolism.
12. Deriving a daily energy density of the lean body mass change and the daily energy density of the fat mass change.
13. Estimating the daily ratio of lean body mass change velocity and fat mass change velocity or equivalently R-ratio.

Regarding individualized self-correcting and self-adaptive modeling, one aspect is achieved through serial measurements of body composition changes and adjustment of the model parameters in a way that the model calculations approach the indirectly measured body composition changes or a target trajectory. Individualized self-correcting and self-adaptive modeling has one advantage of reflecting the state of the individual energy metabolism better than previous models, which were adjusted to grouped or averaged data points of a population.

Regarding real-time calculations with recursive formulas and daily updates, one aspect uses models that use recursive formulas which are updated daily with new data, eliminating the need to know all previous data points except for the last day's data during update and allowing for real-time calculations of changes of body composition as they occur. The recursive method preserves the information gained from the last day's data without the need to store the information in the memory for calculations. One advantage of an algorithm using a recursive structure is that it is easy to use on portable computer devices and allows for making indirect measurements in freely moving human subjects.

Regarding applying linear invertible models, the nonlinear equations used in the Hall model are very difficult or sometimes impossible to invert in order to calculate an unidentified input, the utilized energy intake from a known output, the body composition change and energy expenditure. Also, the thermic effect of feeding is calculated implicitly in the Hall models, making inverse calculations to determine utilized energy intake rather difficult. It has also been found that adaptive thermogenesis, as modeled by Hall with an ad-hoc formula, requires unnecessary assumptions and model parameter determinations when indirect measurement of the body composition can provide this information.

The model equations of one aspect are linear and structured to support inverse calculations for unknown input variables, allowing for calculating the unknown macronutrient energy intake. One advantage of a linear invertible model is that by measuring the body composition change and using an inverse calculation, one aspect determines the difficult to measure utilized macronutrient intake which was necessary to produce the measured body composition change in a freely moving human subject.

Regarding using difference equations, rather than using differential equations, which require continuous measurements and elaborate integration methods to solve, one aspect uses difference equations with 24 hour time resolution requiring model calculations only every 24 hours. The calculations require only matrix operations, eliminating the need for the knowledge of the exact course of changes during the 24 hour period. One advantage of using difference equations is that the explicit knowledge of how the metabolism arrived at the measured new state of body composition after a 24 hour time span is not required.

Regarding using the state space method, the state space method allows for interfacing error containing measurements through the use of a measurement model to a process model describing the metabolic process. The state space method provides a convenient framework for the implementation of the time variant minimum variance Kalman estimation or prediction method.

Regarding calculating macronutrient oxidation rates, it has been found that macronutrient oxidation of carbohydrate, fat, and protein can be modeled for inverse calculation purposes using the principles of indirect calorimetry.[18] One aspect uses the formulas introduced by Livesey, G. and Elia, M. to calculate macronutrient oxidation.[19] One advantage of using these formulas is that they can be directly applied to the self-adaptive individualized metabolic model of the human energy metabolism of one aspect because they are linear and suitable for inverse calculations when model input is sought from known model output.

[18] Indirect calorimetry: methodological and interpretative problems, American Journal of Physiology—Endocrinology and Metabolism. March 1990; 258(3):E399-E412

[19] Livesey, G. and M. Elia. Estimation of energy expenditure, net carbohydrate utilization, and net fat oxidation and synthesis by indirect calorimetry: evaluation of errors with special reference to the detailed composition of fuels. American Journal of Clinical Nutrition. April 1988; 47(4):608-628

Regarding calculating utilized macronutrient intake values from ingested macronutrient calorie intake, the input to the equations of one aspect is the daily utilized macronutrient energy intake without thermic effect of feeding and the energy losses due to incomplete absorption. One aspect calculates the thermic effect of feeding and the energy losses due to incomplete absorption from tabled values.[20] The thermic effect of feeding and the energy losses due to incomplete absorption are subtracted from the ingested calories to obtain the daily utilized carbohydrate, fat, and protein intake. Calculating the daily utilized macronutrient values has one advantage that inverse calculations of the utilized energy intake become independent from the individual thermic effect of feeding or food absorption variables.

[20] Food and Nutrition Board, Institute of Medicine. Dietary Reference Intakes for Energy, Carbohydrate, Fiber, Fat, Fatty Acids, Cholesterol, Protein, and Amino Acids (Macronutrients): A Report of the Panel on Macronutrients, Subcommittees on Upper Reference Levels of Nutrients and Interpretation and Uses of Dietary Reference Intakes, and the Standing Committee On the Scientific Evaluation of Dietary Reference Intakes. http://www.nap.edu/books/0309085373/html/

Regarding using the law of conservation of energy, the energy equations of one aspect take into account all major known processes of the human energy metabolism and are built to satisfy the law of conservation of energy at the end of a 24 hour period. One aspect accommodates the so far unknown energy forms in the energy balance equation by using a correction factor for unknown energy losses or gains. Including a correction factor for unknown energy losses or gains has one advantage of balancing the energy equations of one aspect so that they satisfy the law of conservation of energy. The correction factor for unknown energy losses or gains also serves as a measure of performance of the model of one aspect, since the major components of the energy equation are included in the model of one aspect and the expectation is that the unknown energy forms remain small.

Regarding estimating the daily utilized macronutrient intake values from indirectly measured body composition changes, one aspect uses the time variant Kalman prediction method with innovations representation for prediction and estimation of the unknown utilized macronutrient intake.[21] For estimating the error of estimation, one aspect uses a reference or nominal trajectory method.[22] The reference or nominal trajectory method has one advantage of enhancing the accuracy and stability of estimations. One advantage of utilizing the Kalman prediction, innovations representation, and the reference or nominal trajectory method is that is possible to estimate the daily utilized macronutrient intake in a freely moving human subject and requires only daily measurement of the physical energy expenditure and determination of the body composition change along with an infrequently used calibration procedure.

[21] Ljung, L. and T. Söderström. Theory and Practice of Recursive Identification. 1983; MIT Press, Cambridge, Mass., pp. 125

[22] Jazwinski, A. W. Stochastic Processes and Filtering Theory. 1970; Academic Press, Inc. New York, pp. 376

Regarding estimating the daily changes of the body composition and stochastic identification of the unidentified energy losses or gains, correction factor of the de novo lipogenesis, and correction factor for gluconeogenesis, one aspect uses the time variant Kalman filtering method with innovations representation for estimation of the daily body composition change. One aspect calculates the unknown energy losses or gains, the correction factor for de novo lipogenesis, and the correction factor for gluconeogenesis from amino acids with a stochastic identification method.[23] One aspect uses a reference or nominal trajectory method for estimating the daily body composition changes.[24] The method of one aspect has the advantage of enhancing accuracy and stability of estimations of daily body composition changes and allowing for dynamic indirect individualized measurement of components of the human energy metabolism in a freely moving human subject requiring only daily measurement of the physical energy expenditure and the determination of the body composition change along with an infrequently used calibration procedure for body composition and hydration status change.

[23] Walter, E. and L. Pronzato. Identification of Parametric Models from Experimental Data. 1997; Springer Verlag Berlin, Paris, New York. pp. 114

[24] Jazwinski, A. W. Stochastic Processes and Filtering Theory. 1970; Academic Press, Inc. New York, pp. 376

Regarding deriving the Canonical Model Form of the Human Energy Metabolism, in computer science when representing mathematical objects in a computer, there are usually many different ways to represent the same object. In this context, a canonical form is a representation such that every object has a unique representation. Thus, the equality of two objects can easily be tested by testing the equality of their canonical forms. Here, one aspect uses a canonical representation of the human energy metabolism. One advantage of using such a representation is that the calculated metabolic parameters allow for intra- as well as inter-individual comparisons of the indirectly measured metabolic parameters. This allows quantitative characterization of the metabolism and enhances understanding of individual variations and predicts the effect of dietary and exercise interventions.

Regarding daily energy density of the lean body mass change and the daily energy density of the fat mass change, central to the development of the canonical representation of the energy metabolism is to quantify the relationship between total energy balance and daily lean body mass and fat mass change. One aspect uses a method to quantify this energy relationship by estimating the daily energy density of the lean body mass change and the daily energy density of the fat mass change. One advantage is that long term trends or trajectories of the lean body mass and fat mass changes can be estimated to predict future changes quantitatively.

Regarding estimating the daily ratio of lean body mass change velocity and fat mass change velocity or equivalently R-ratio, the association of obesity with type 2 diabetes has been recognized to be in large part due to insulin resistance and consequential hyperinsulinemia. Insulin resistance and ensuing high average level of insulin promotes among other processes of lipogenesis and diminishes triglyceride breakdown by inhibiting lipolysis. Further, the mobilization of fat from the fat stores between meals is reduced, resulting in a surplus of fatty acid at the cellular level, which creates a state described as lipotoxicity.[25] Lipotoxicity is linked to decreased fat oxidation leading to impaired capability of losing weight intentionally. One aspect uses a surrogate measure for insulin resistance called "R-ratio". This ratio establishes a quantitative relationship between daily lean body mass change velocity and fat mass change velocity. Practical, stable methods are used to estimate this relationship. One advantage is that the R-ratio shows strong correlation with other surrogate markers of insulin resistance such as the HOMA-IR (homeostasis assessment model of insulin resistance) and appears to be promising for non-invasive tracking of the insulin resistance change. The calculated correlation coefficient between the R-ratio and HOMA-IR is −0.8383 with P value of 0.0093 and was found by using data from the Dietary Weight Loss and Exercise Effects on Insulin Resistance in Postmenopausal Women.[26]

[25] Lelliott, DOI: 10.1038/sj.ijo.0802854
[26] Mason, DOI: 10.1016/j.amepre.2011.06.042

Figure 1B:
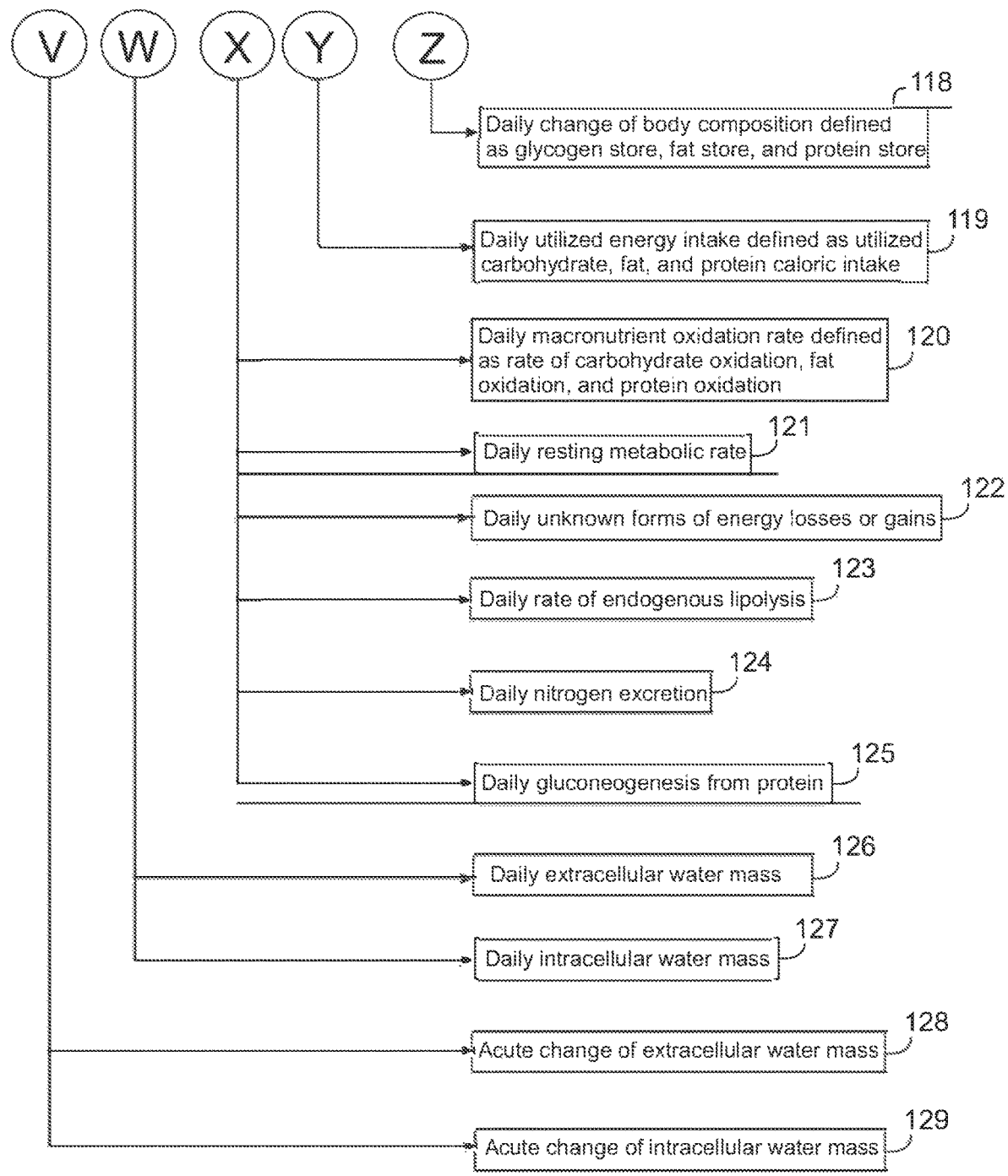
Figure 5A:
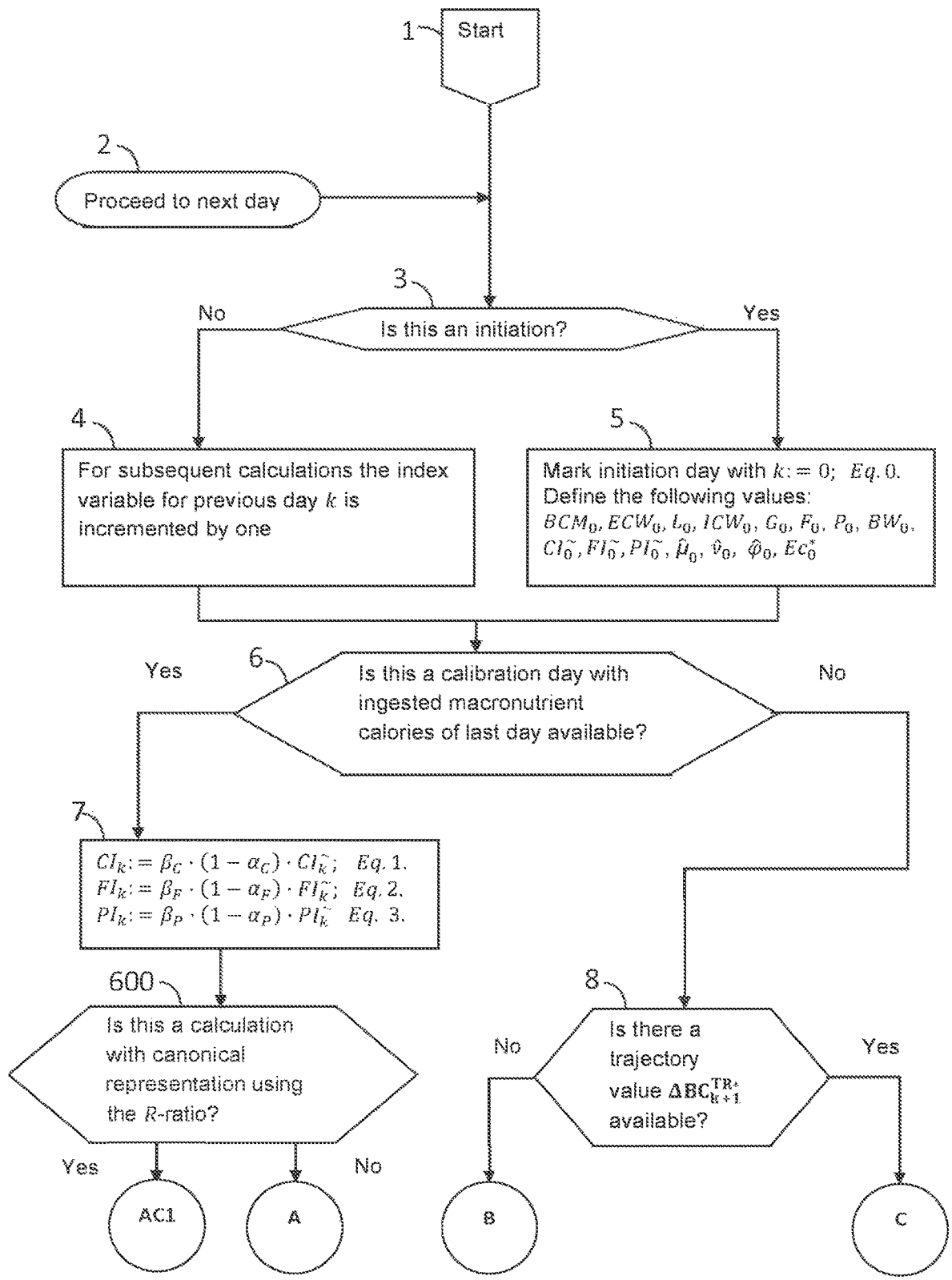
FIGS. 5A, 5B, SC, 5D, 5E, 5F, 5G, 5H, 5I, 5J, 5K, 5L, 5M, 5N, 5O, 5P, 5Q, 5R, 5S, 5T, 5U and 5V are flowcharts illustrating the analysis of change of body composition and hydration status and the dynamic indirect individualized measurement of components of the human energy metabolism, including an R-ratio method using a Canonical Model Form of the Human Energy Metabolism method and estimating the daily energy density of the lean body mass change, the daily energy density of the fat mass change, and the daily ratio of lean body mass change velocity and fat mass change velocity or equivalently R-ratio.
Figure 5D:
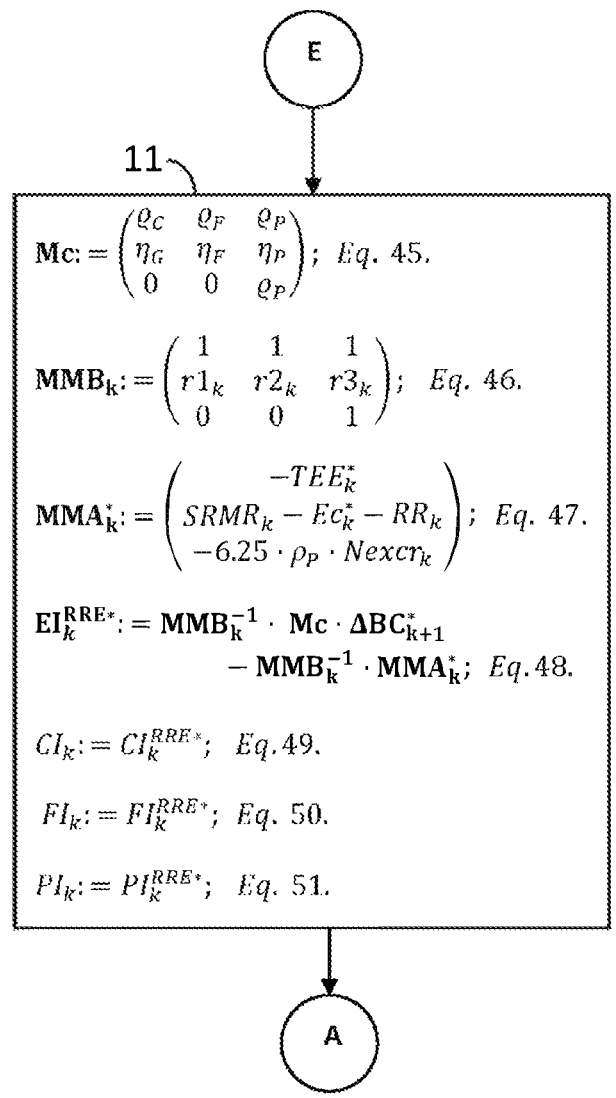
Figure 5I:
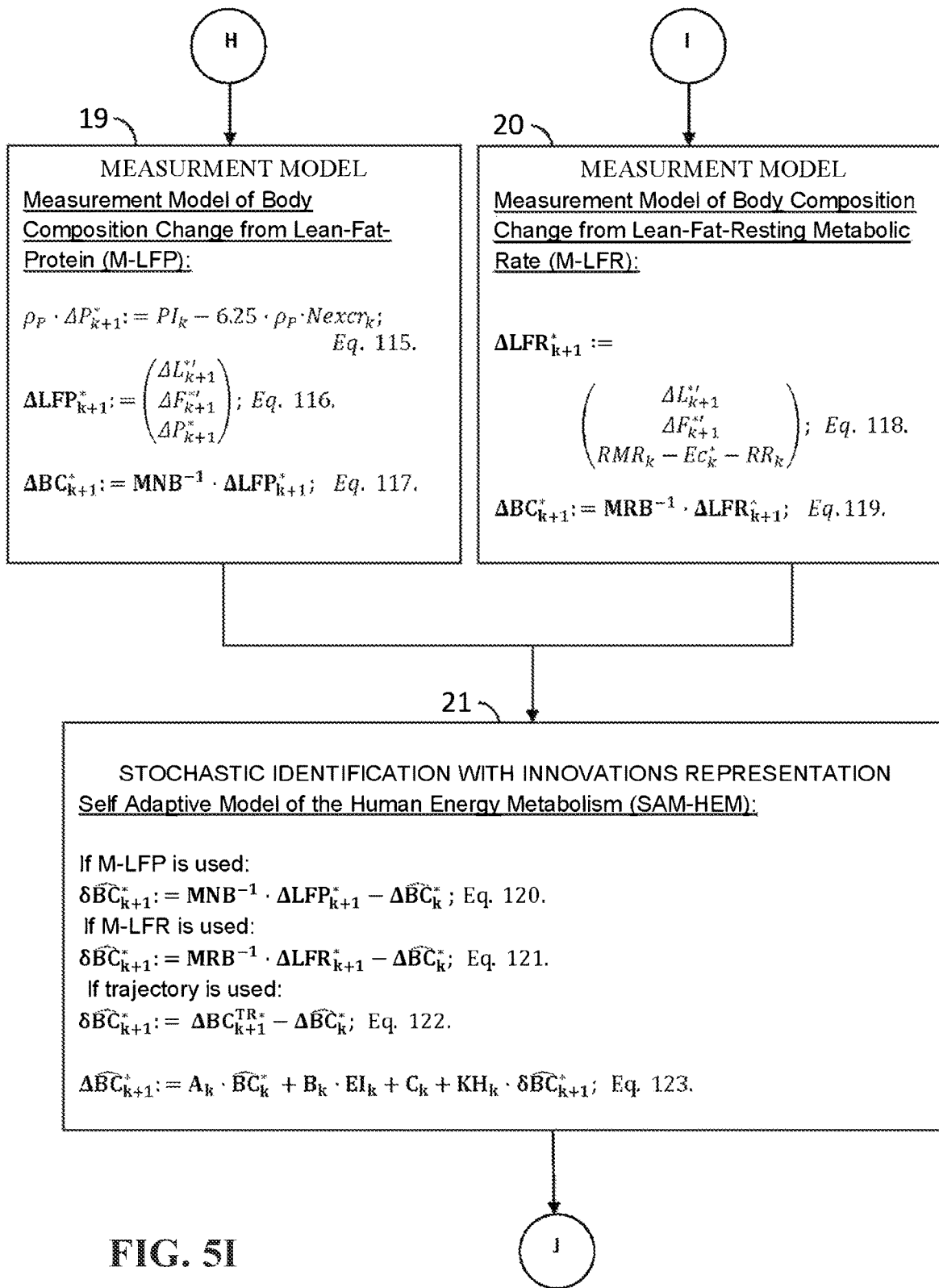
Figure 5J:
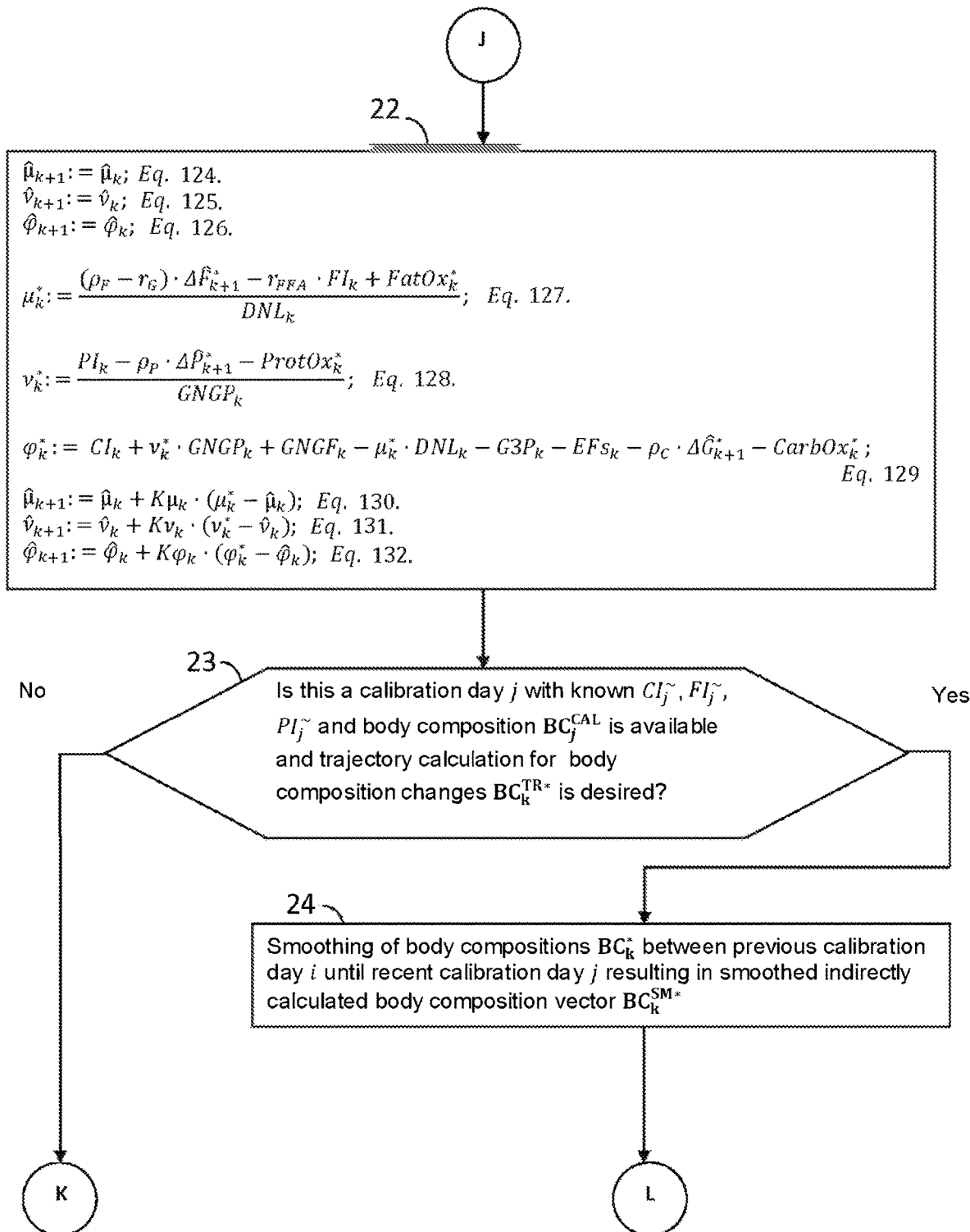
Figure 5K:
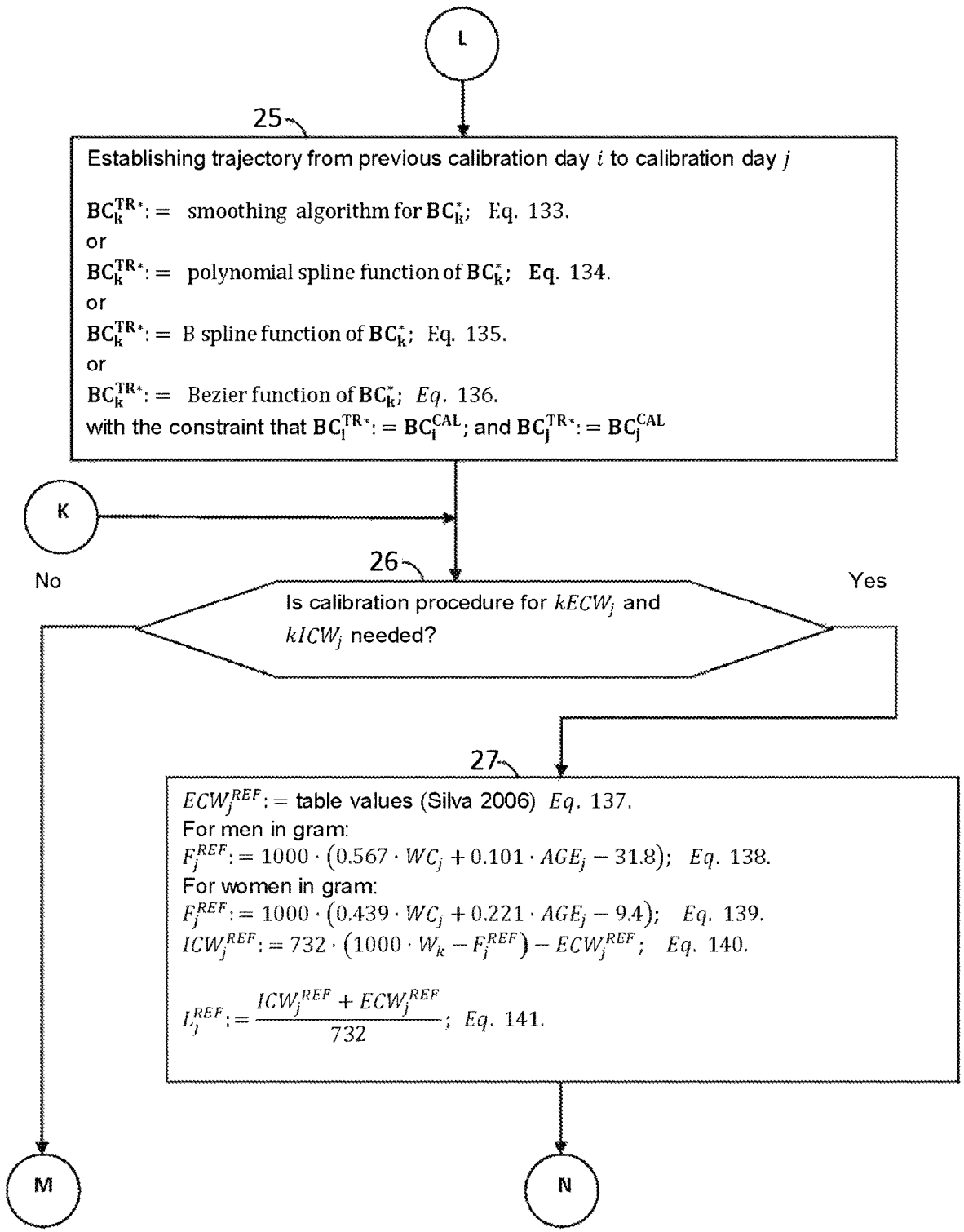

FIGS. 1A and 1B illustrate how the measurements of a first embodiment for body composition and hydration status analysis 109 flows into a method 130 for dynamic indirect individualized measurement of components of the human energy metabolism, and this method 130 is illustrated in detail in the flowchart in FIG. 5A to 5V.

A human subject 105 undergoes a body composition change of his or her glycogen store, fat store, and protein store on an examined day k. A total energy expenditure 101 is produced on day k and leaves the human subject 105 on day k. Energies enter the human subject 105 in the form of the ingested carbohydrate intake 102, fat intake 103, and protein intake 104 on day k. A device for body composition and hydration status analysis 109 measures resistance directly at multiple frequencies and extrapolated indirectly to a zero frequency and an extrapolated infinite frequency on day k 106. The same device for body composition and hydration status analysis 109 measures the extracellular water mass on day k 126, the intracellular water mass on day k 127, and the change of lean body mass and fat mass on day k 107. The same device 109 can optionally measure acute change of extracellular water mass and intracellular water mass 108. A measurement of physical activity energy expenditure 110 is required on day k. Optional measurements of ingested energy in the form of carbohydrate 111, fat 112, and protein 113 are taken on day j for calibration purposes. An optional measurement of resting metabolic rate 114 is taken on day j for calibration purposes. An optional measurement of nitrogen excretion 115 is taken on day j for calibration purposes and to indirectly measure the daily gluconeogenesis. An optional measurement of the rate of endogenous lipolysis 116 is taken on day j for calibration purposes and to indirectly measure the daily lipolysis. The method for dynamic indirect individualized measurement of components of the human energy metabolism 130 comprises a Self-Correcting Model of the Utilized Energy Intake 131, a Self-Adaptive Model of the Human Energy Metabolism 132, and a calculation of the components of the human energy metabolism 133. The Self-Correcting Model of the Utilized Energy Intake 131 estimates the utilized energy intake, defined as the daily utilized energy of carbohydrate, fat, and protein caloric intake 119. The Self-Adaptive Model of the Human Energy Metabolism 132 estimates the daily change of body composition, defined as the change of glycogen store, fat store, and protein store 118. The calculation of the components of the human energy metabolism 133 provides the macronutrient oxidation rate results, defined as the daily rate of carbohydrate oxidation, fat oxidation, and protein oxidation 120; daily resting metabolic rate 121; daily unknown forms of energy losses or gains 122; daily rate of endogenous lipolysis 123; daily nitrogen excretion 124; and daily gluconeogenesis from protein 125.

Figure 2:
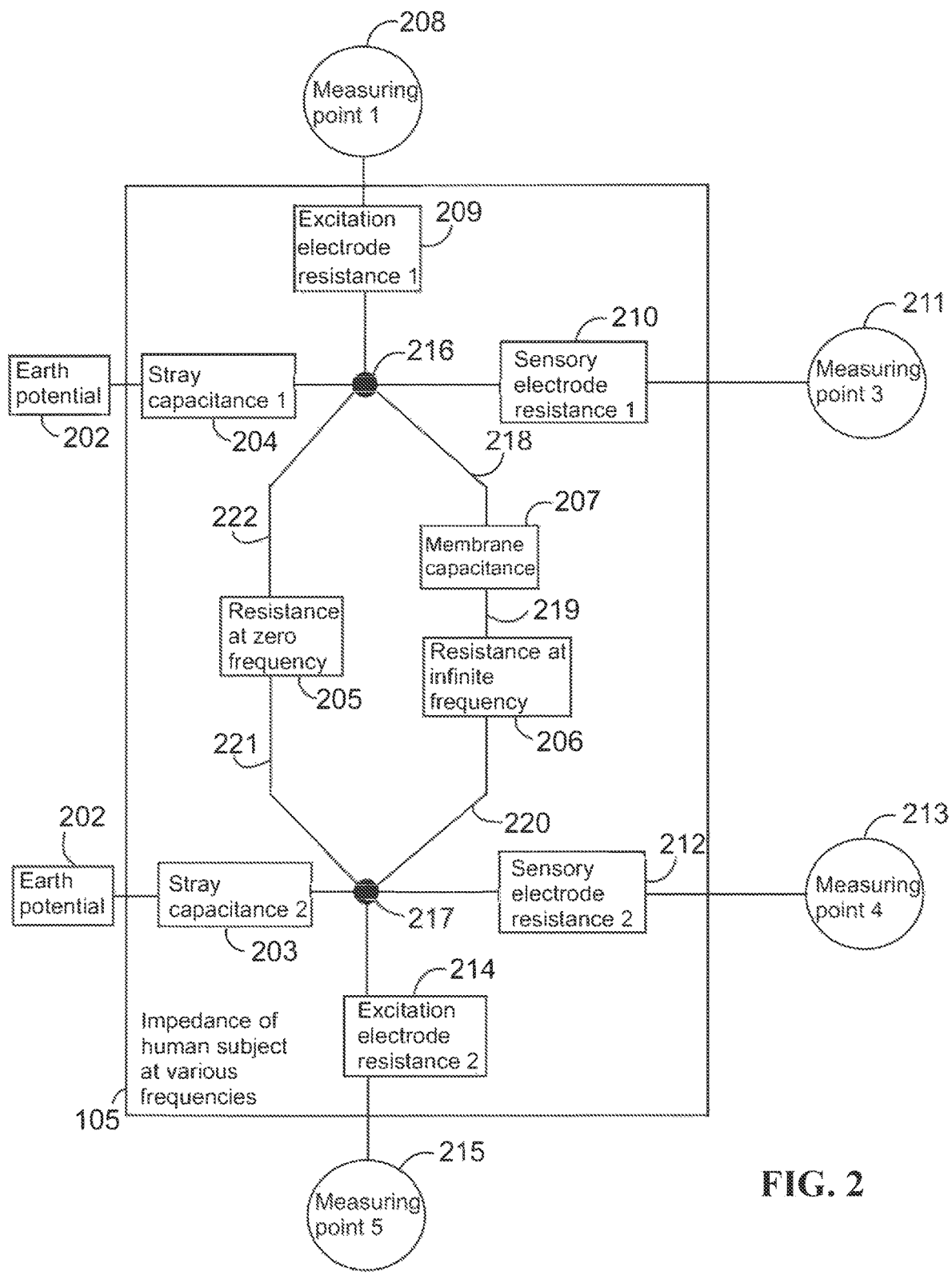
FIG. 2 is an interface electrical connection between a human subject and measuring points.

FIG. 2 illustrates an interface electrical connection between the human subject 105 and measuring points 1, 208, measuring point 3, 211, measuring point 4, 213, and measuring point 5, 215. The same figure also shows the lumped circuit diagram equivalent of the human subject 105 connected to nodal junctions 216 and 217. The lumped circuit diagram is made up of the resistance at an estimated zero frequency 205 connected parallel to the serially connected membrane capacitance 207 and resistance at an extrapolated infinite frequency 206. Nodal junction 216 is also connected to earth potential 202 through stray capacitance 1, 204. Nodal junction 216 is also connected to measuring point 1, 208 through excitation electrode resistance 1, 209, and to measuring point 3, 211, through Sensory electrode resistance 1, 210. Nodal junction 217 is also connected to earth potential 202 through stray capacitance 2, 203. Nodal junction 217 is also connected to measuring point 5, 215 through excitation electrode resistance 2, 214 and to measuring point 4, 213 through sensory electrode resistance 2, 212. I model the human impedance with a Cole circuit model consisting of a resistance at an estimated zero frequency 205 connected parallel to the serially connected membrane capacitance 207 and resistance at an extrapolated infinite frequency 206. This Cole circuit model provides the impedance of the human subject 105.

Figure 3:
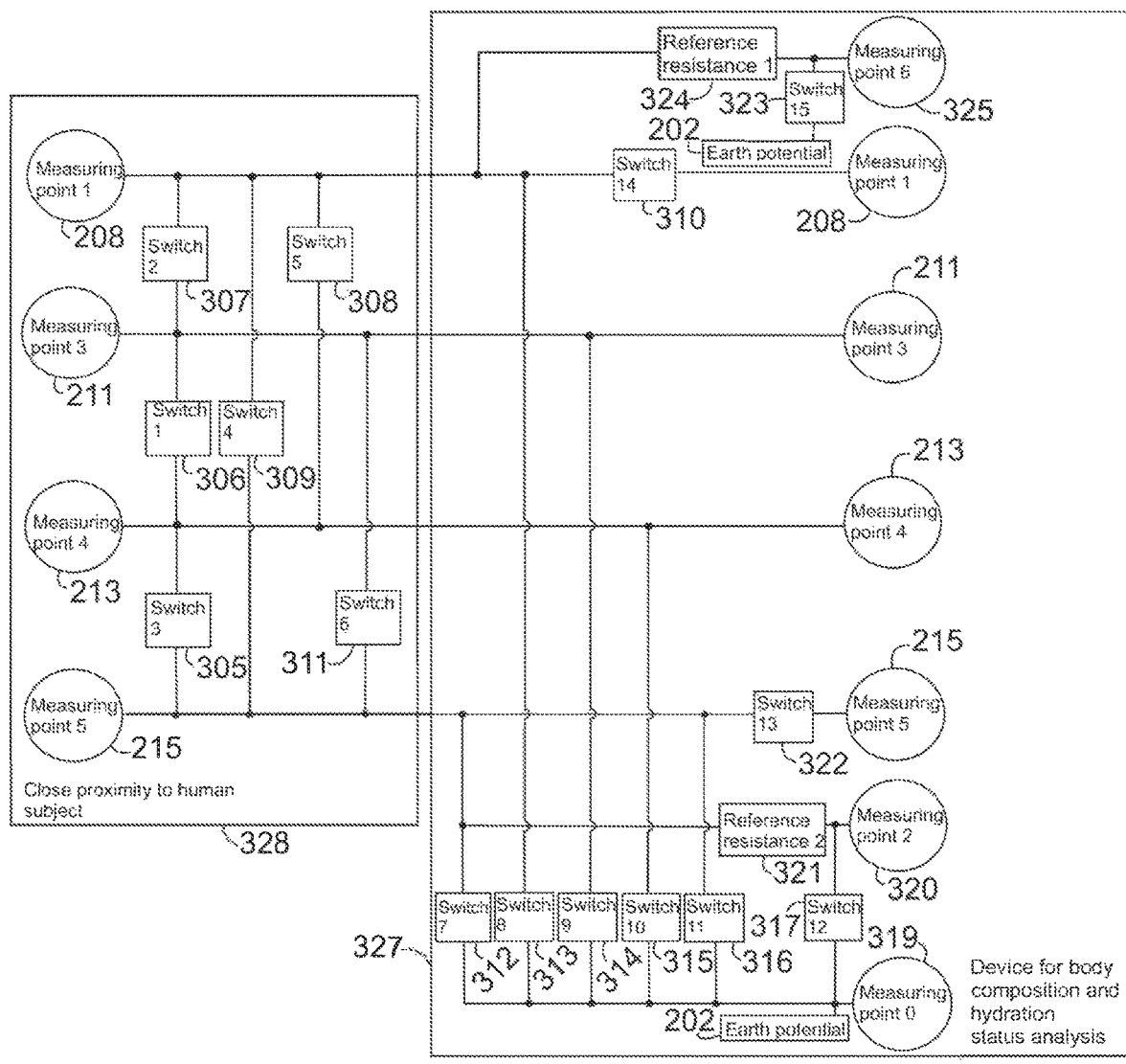
FIG. 3 is an input logic circuit connecting measuring points.

FIG. 3 illustrates an input logic circuit connecting measuring point 1, 208, measuring point 3, 211, measuring point 4, 213, and measuring point 5, 215, which are in close proximity to the human subject 328, with measuring point 1, 208, measuring point 3, 211, measuring point 4, 213, measuring point 5, 215, and measuring point 6, 325, inside of a device for body composition and hydration status analysis 327. Measuring point 1, 208, in close proximity to the human subject 328, is connected to measuring point 1, 208, inside of the device for body composition and hydration status analysis 327, through on and off switch 14, 310. Measuring point 1, 208, in close proximity to the human subject 328, is also connected to measuring point 6, 325, inside of the device for body composition and hydration status analysis 327, through reference resistance 1, 324. Measuring point 3, 211, in close proximity to the human subject 328, is directly connected to measuring point 3, 211, inside of a device for body composition and hydration status analysis 327. Measuring point 4, 213, in close proximity to the human subject 328, is directly connected to measuring point 4, 213, inside of a device for body composition and hydration status analysis 327. Measuring point 5, 215, in close proximity to the human subject 328, is connected to measuring point 5, 215, inside of the device for body composition and hydration status analysis 327, through on and off switch 13, 322. Measuring point 5, 215, in close proximity to the human subject 328, is connected to measuring point 2, 320, inside of the device for body composition and hydration status analysis 327, through reference resistance 2, 321. Measuring point 5, 215, in close proximity to the human subject 328, is connected to measuring point 0, 319, inside of the device for body composition and hydration status analysis 327, through on and off switch 7, 312.

Measuring points 1, 3, 4, and 5, 208, 211, 213, and 215, respectively, in close proximity to the human subject 328, are connected through on and off switches 1-6, 306, 307, 305, 309, 308, and 311, respectively. Measuring point 1, 208, is connected to measuring point 3, 211, through on and off switch 2, 307. Measuring point 1, 208, is connected to measuring point 5, 215, through on and off switch 4, 309. Measuring point 1, 208, is connected to measuring point 4, 213, through on and off switch 5, 308. Measuring point 3, 211, is connected to measuring point 4, 213, through on and off switch 1, 306. Measuring point 3, 211, is connected to measuring point 5, 215, through on and off switch 6, 311. Measuring point 4, 213, is connected to measuring point 5, 215, through on and off switch 3, 305.

Measuring points 6, 1, 3, 4, 5, 2, and 0, 325, 208, 211, 213, 215, 320, and 319, respectively, inside of the device for body composition and hydration status analysis 327, are connected through on and off switches 7-15, 312, 313, 314, 315, 316, 317, 322, 310, and 323, respectively. Measuring point 0, 319, is connected to earth potential 202. Measuring point 6, 325, is connected to measuring point 0, 319, through reference resistance 1, 324, and on and off switch 8, 313. Measuring point 6, 325, is also connected to earth potential 202 through on and off switch 15, 323. Measuring point 1, 208, is connected to measuring point 0, 319, through on and off switch 14, 310, and on and off switch 8, 313. Measuring point 3, 211, is connected to measuring point 0, 319, through on and off switch 9, 314. Measuring point 4, 213, is connected to measuring point 0, 319, through on and off switch 10, 315. Measuring point 5, 215, is connected to measuring point 0, 319, through on and off switch 11, 316. Measuring point 2, 320, is connected to measuring point 0, 319, through on and off switch 12, 317.

Figure 4:
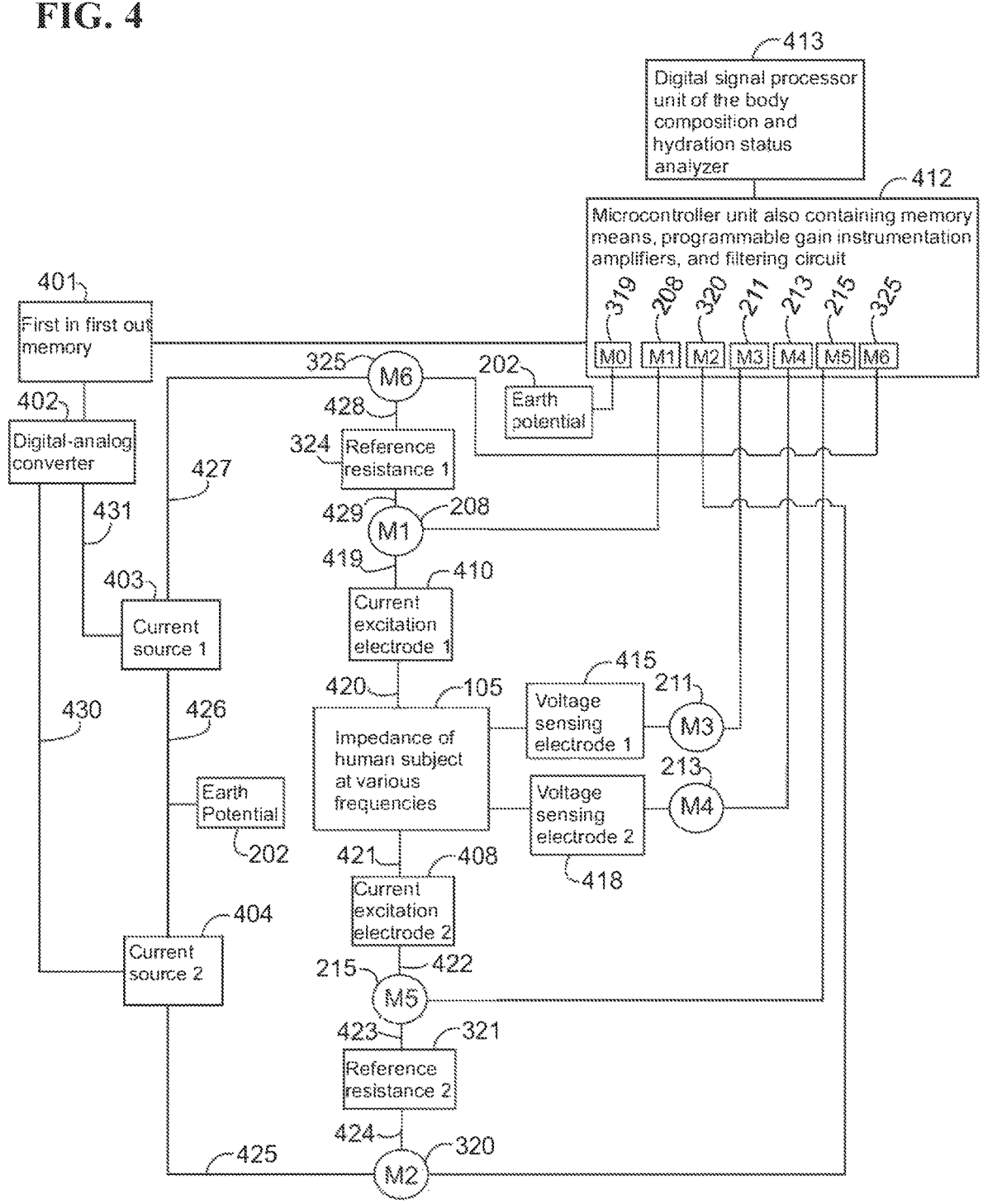
FIG. 4 is the measuring circuit of the first embodiment configured to determine the impedance of a human subject at various frequencies.

FIG. 4. illustrates the measuring circuit of the first embodiment to determine the impedance of a human subject at various frequencies. The measuring circuit consists of the following elements in this order: connecting element 427; M6 or measuring point 6, 325; connecting element 428; reference resistance 1, 324; connecting element 429; M1 or measuring point 1, 208; connecting element 419; current excitation electrode 1, 410; connecting element 420; impedance of the human subject at various frequencies consisting of resistance and reactance, 105; connecting element 421; current excitation electrode 2, 408; connecting element 422; M5 or measuring point 5, 215; connecting element 423; reference resistance 2, 321; connecting element 424; M2 or measuring point 2, 320; connecting element 425; current source 2, 404; connecting element 426, which is also connected to earth potential 202; current source 1, 403; and again connecting element 427.

The current source driving means consists of a first in first out memory 401 and a digital-analog converter 402, which are connected with each other. The first in first out memory 401 is connected to the microcontroller unit 412 also containing memory means and a six-channel programmable gain instrumentation amplifier and filtering circuit. The digital-analog converter 402 is connected 431 to current source 1, 403, and is also connected 430 to current source 2, 404.

M1 or measuring point 1, 208, is between reference resistance 1, 324, and current excitation electrode 1, 410, on the measuring circuit and is also connected to M1 or measuring point 1 input 208 inside the microcontroller unit 412. M2 or measuring point 2, 320, is between current source 2, 404, and reference resistance 2, 321, on the measuring circuit and is also connected to M2 or measuring point 2 input 320 inside the microcontroller unit 412. M3 or measuring point 3, 211, is connected to voltage sensing electrode 1, 415, and is also connected to M3 or measuring point 3 input 211 inside the microcontroller unit 412. M4 or measuring point 4, 213, is connected to voltage sensing electrode 2, 418, and is also connected to M4 or measuring point 4 input 213 inside the microcontroller unit 412. M5 or measuring point 5, 215, is between current excitation electrode 2, 408, and reference resistance 2, 321, on the measuring circuit and is also connected to M5 or measuring point 5 input 215 inside the microcontroller unit 412. M6 or measuring point 6, 325, is between reference resistance 1, 324, and current source 1, 403, on the measuring circuit and is also connected to M6 or measuring point 6 input 325 inside the microcontroller unit 412.

Voltage sensing electrode 1, 415, is between the human subject with its impedance at various frequencies 105 and M3 or measuring point 3, 211. Voltage sensing electrode 2, 418, is between the human subject with its impedance at various frequencies 105 and M4 or measuring point 4, 213. M0 or measuring point 0 input 319 inside the microcontroller unit 412 is connected to earth potential 202. The digital signal processor unit of the device for body composition and hydration status analysis 413 is connected to the microcontroller unit 412.

The overview of the operation of the first embodiment of the apparatus and method for the analysis of change of body composition and hydration status and for dynamic indirect individualized measurement of components of the human energy metabolism is depicted in FIGS. 1A and 1B. Appendix A lists the definitions of the upper indices, definitions of lower indices, signs for the estimated value and assigned variable, scalar variables, vector variables, matrix variables, dynamic system and process models, measurement models, and model constants and definitions used in my first embodiment.

Figure 5L:
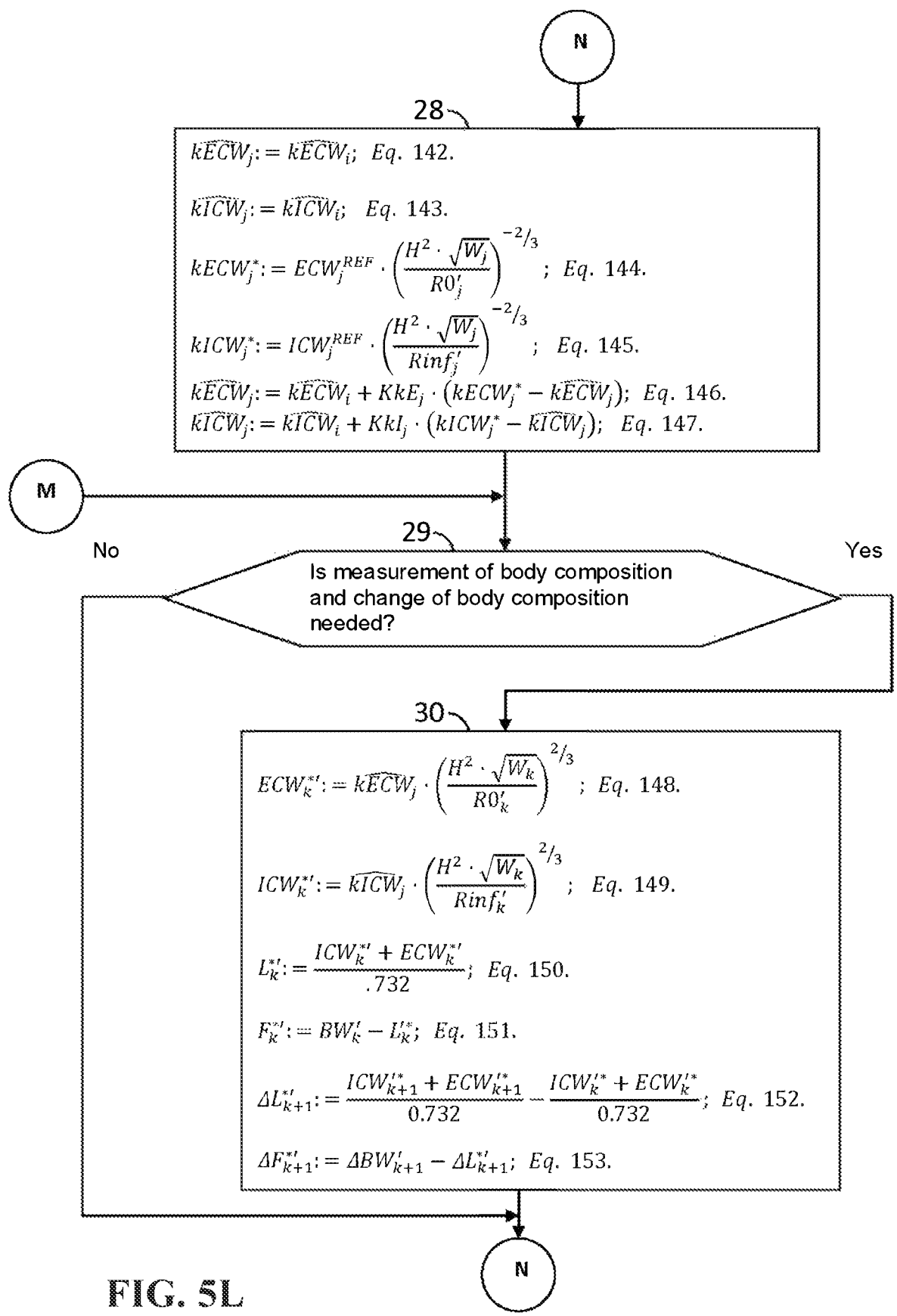
Figure 5M:
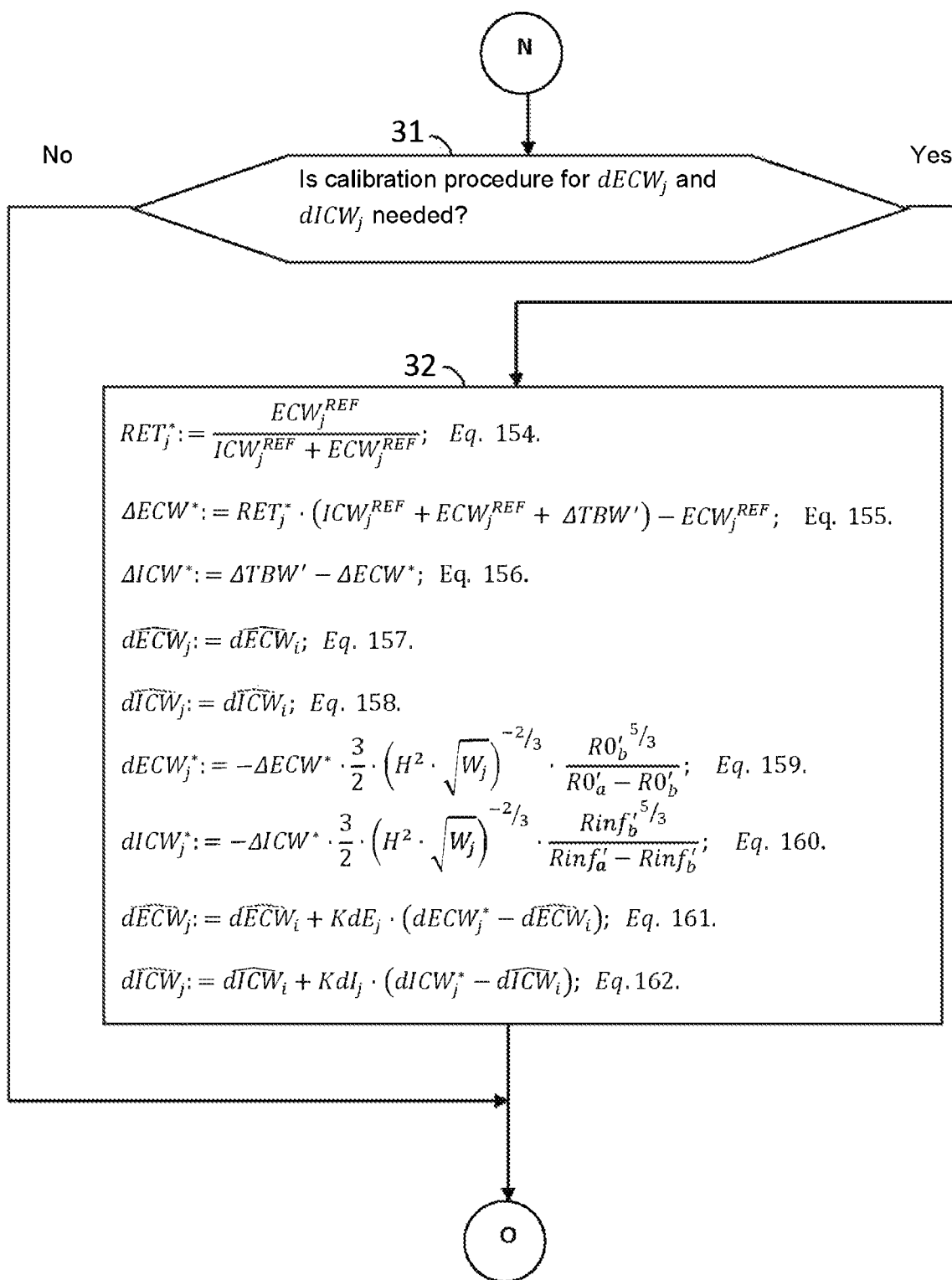
Figure 5N:
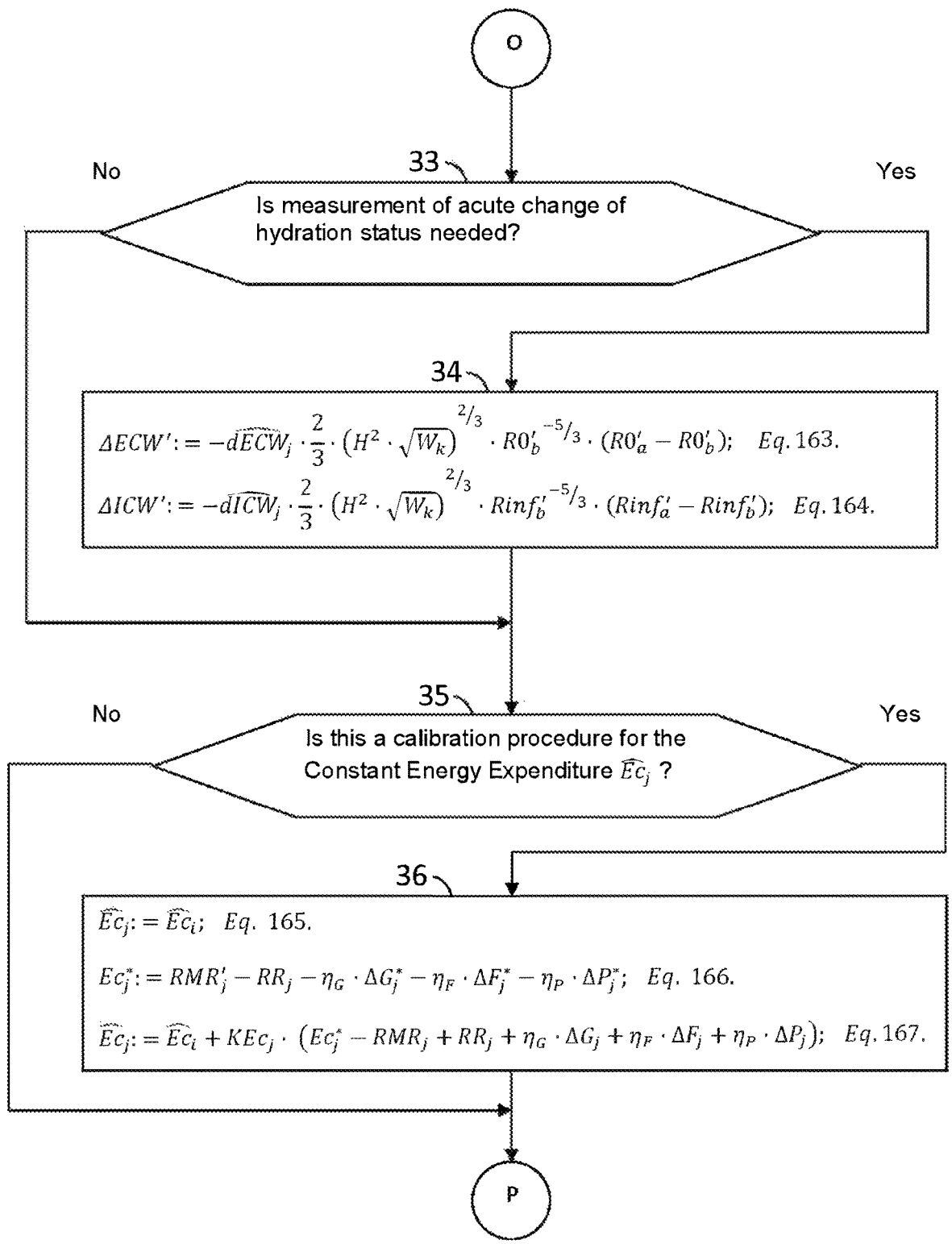
Figure 50:
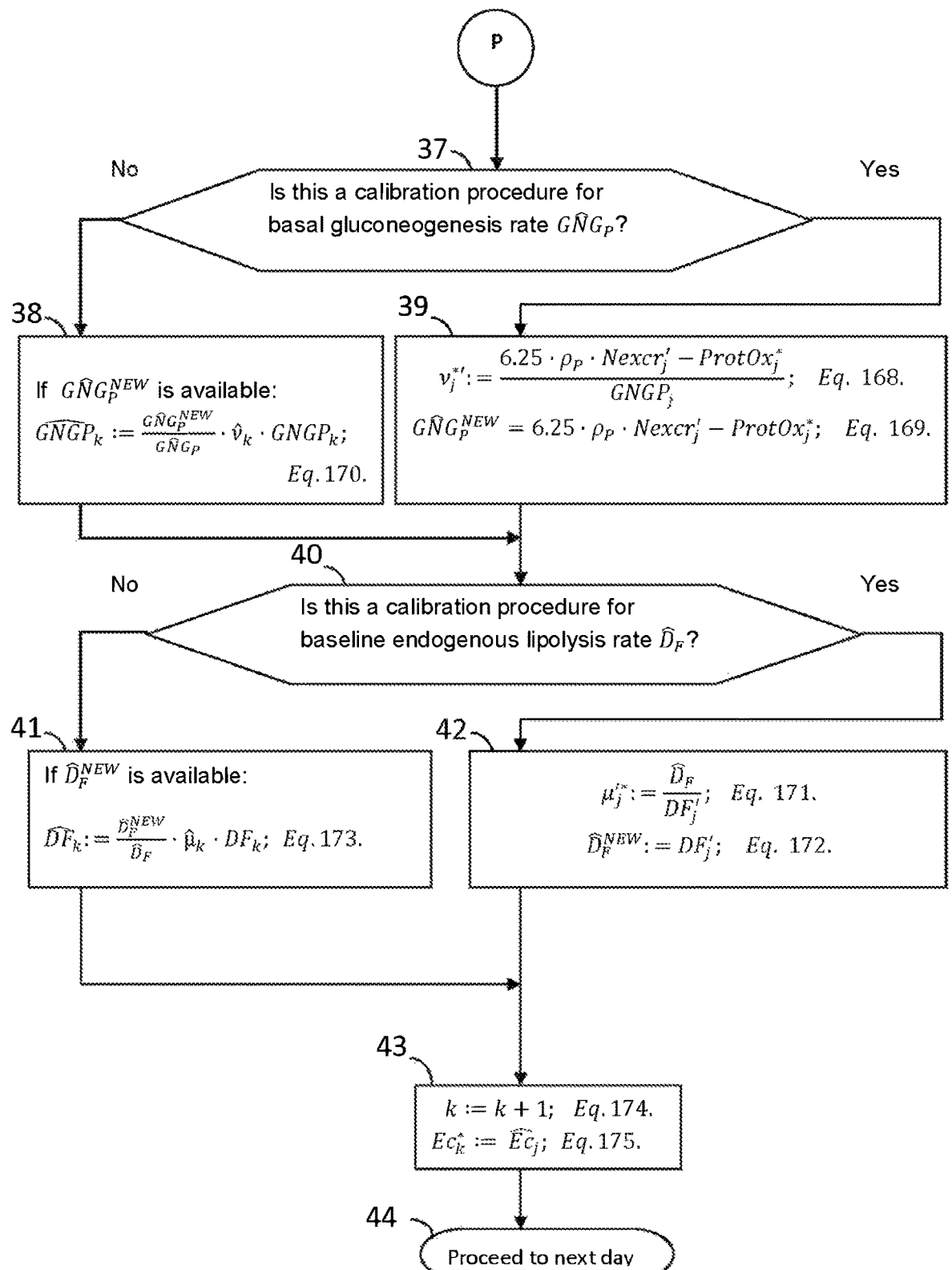
Figure 5P:
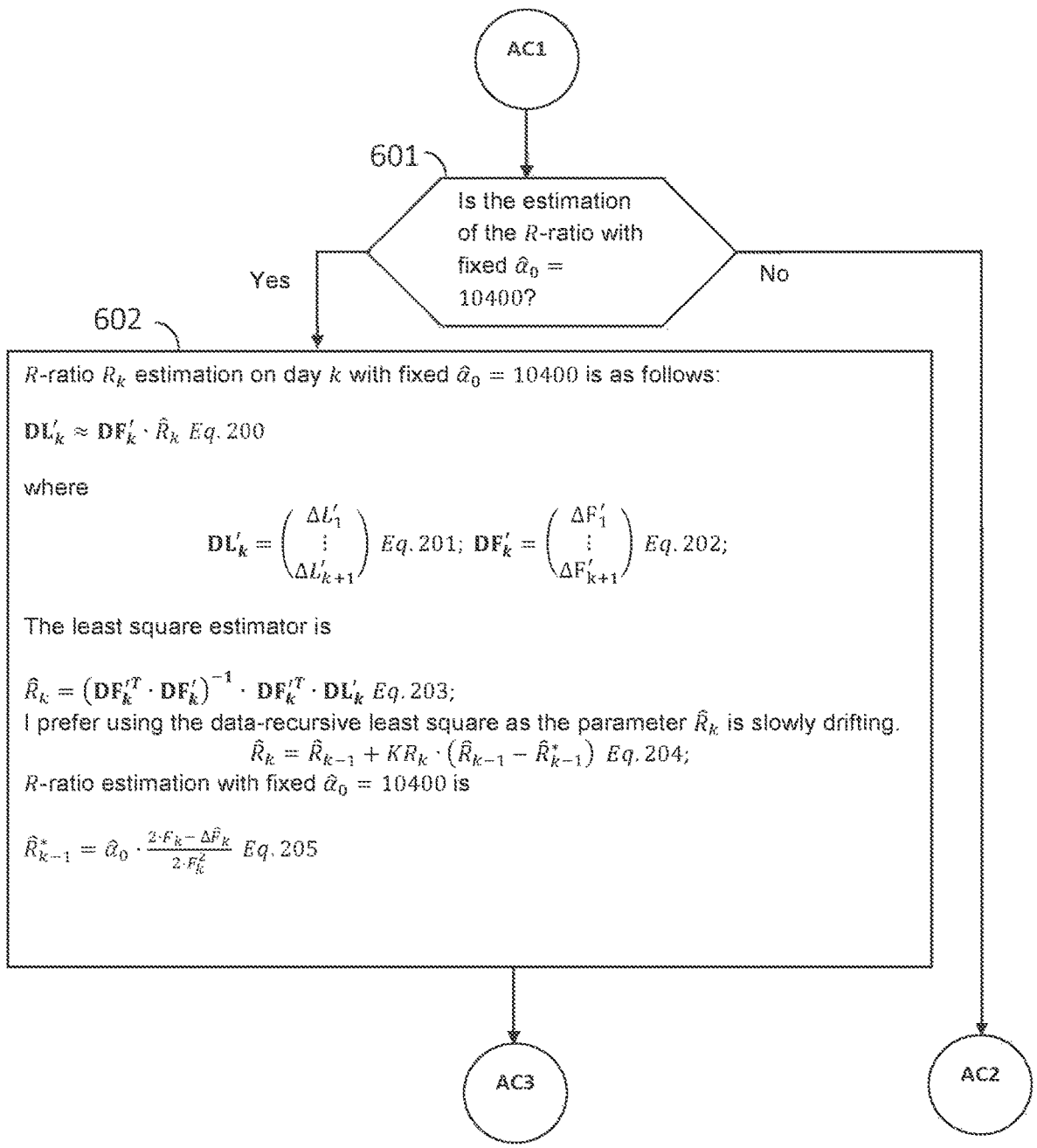
Figure 5Q:
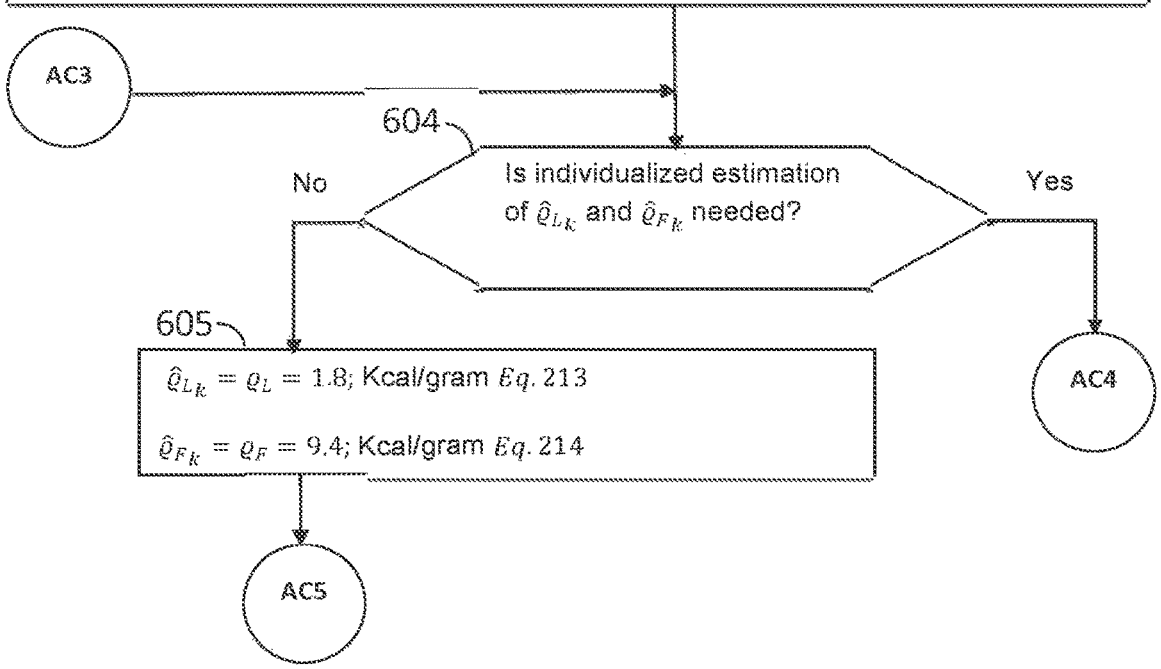
Figure 5T:
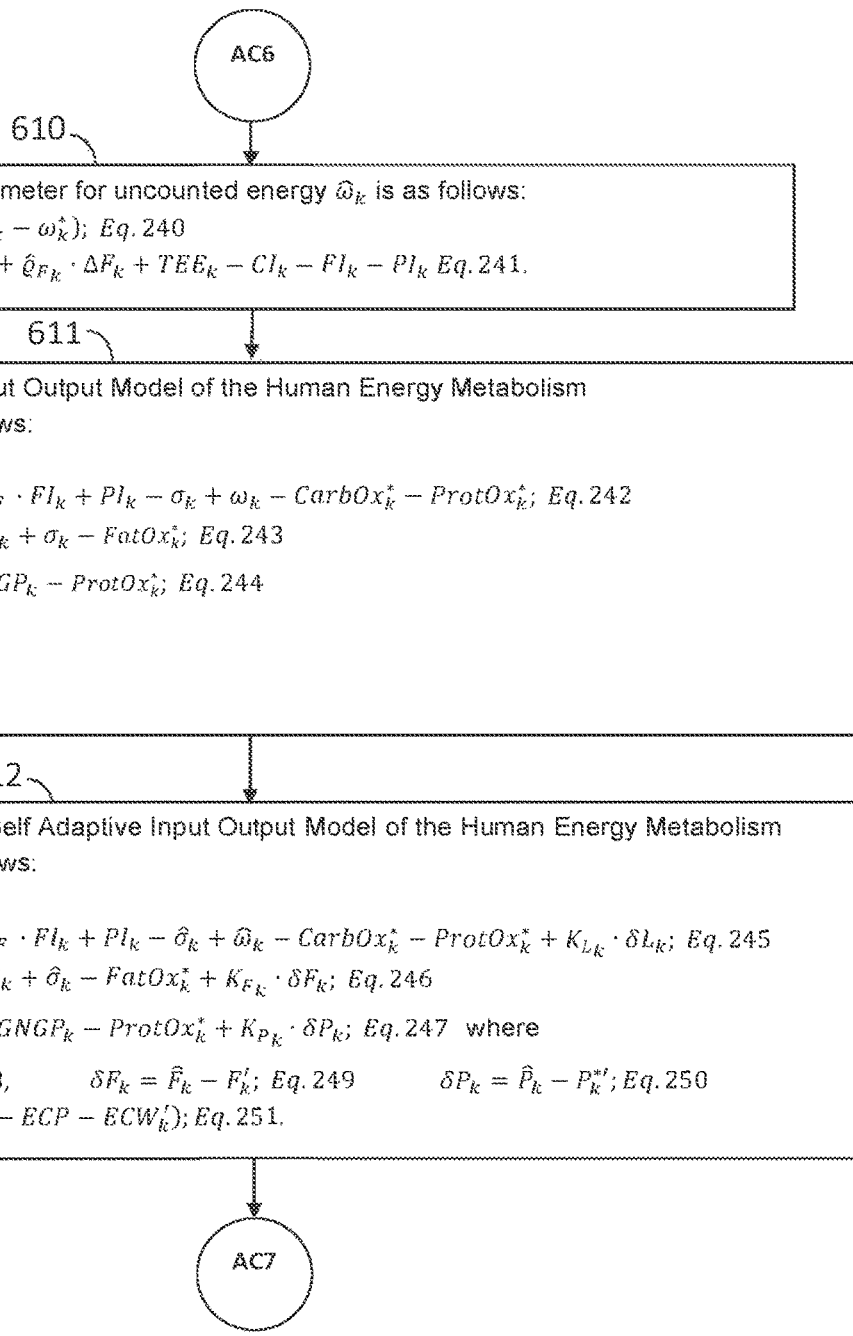

The human subject's metabolism 105 takes up energy in the form of the ingested carbohydrate intake 102, fat intake 103, and protein intake 104 on day k. The metabolism uses this energy intake; the human subject 105 undergoes body composition change of his or her glycogen store, fat store, and protein store on an examined day k; and a total energy expenditure 101 is produced. The embodiment of the apparatus for the analysis of change of body composition and hydration status 109 measures resistance directly at multiple frequencies and extrapolates indirectly to zero frequency and an extrapolated infinite frequency on day k 106. Using these results the same device 109 measures the extracellular water mass 126, the intracellular water mass 127, the change of lean body mass, and change of fat mass on day k 107. The extracellular water mass and intracellular water mass 107 are calculated as in Eq. 148. and Eq. 149., respectively, in process 30, FIG. 5L. The change of lean body mass and change of body fat mass 107 are calculated as in Eq. 152. and Eq. 153., respectively, in process 30, FIG. 5L. The same device 109 can optionally measure acute change of extracellular water mass and intracellular water mass 108. The acute change of extracellular and intracellular water mass 108 are calculated as in Eq. 163. and Eq. 164., respectively, in process 34, FIG. 5N. A measurement of physical activity energy expenditure 110 is required on day k. Optional measurements of ingested energy in the form of carbohydrate 111, fat 112, and protein 113 are taken on day j for calibration purposes. An optional measurement of resting metabolic rate 114 is taken on day j for calibration purposes. An optional measurement of nitrogen excretion 115 is taken on day j for calibration purposes to indirectly measure daily gluconeogenesis. An optional measurement of the rate of endogenous lipolysis 116 is taken on day j for calibration purposes to indirectly measure daily lipolysis. The method for dynamic indirect individualized measurement of components of the human energy metabolism 130 comprises a Self-Correcting Model of the Utilized Energy Intake 131, a Self-Adaptive Model of the Human Energy Metabolism 132, and a calculation of the components of the human energy metabolism 133. The Self-Correcting Model of the Utilized Energy Intake 131 estimates the utilized energy intake, defined as the daily utilized energy of carbohydrate, fat, and protein caloric intake 119. The Self-Adaptive Model of the Human Energy Metabolism 132 estimates the daily change of body composition, defined as the change of glycogen store, fat store, and protein store 118. The calculation of the components of the human energy metabolism 133 provides the macronutrient oxidation rate results, defined as the daily rate of carbohydrate oxidation, fat oxidation, and protein oxidation 120; daily resting metabolic rate 121; daily unknown forms of energy losses or gains 122; daily rate of endogenous lipolysis 123; daily nitrogen excretion 124; and daily gluconeogenesis from protein 125.

The overview of the operation of an embodiment of the apparatus for the analysis of change of body composition and hydration status 109 is depicted on FIG. 2, FIG. 3, and FIG. 4. The passive circuit elements of the Cole circuit model representing the impedance of the human subject 105 is measured. The Cole circuit model consists of a resistance at an estimated zero frequency 205 connected parallel to the serially connected membrane capacitance 207 and resistance at an extrapolated infinite frequency 206. At an estimated zero frequency, the Cole circuit model consists of a resistance at the estimated zero frequency 205 and at an extrapolated infinite frequency it reduces to a parallel circuit of a resistance at the estimated zero frequency 205 connected parallel to a resistance at the extrapolated infinite frequency 206. For higher frequencies than zero and lower frequencies than an extrapolated infinite frequency, the Cole circuit model has properties of a complex impedance with a resistance and reactance value. I perform measurements at a multitude of discrete preset frequencies from 1 kilohertz to 1 megahertz. At these frequencies, the presence of a membrane capacitance 207 is also measurable and 205, 206, and 207 is detected as a specific resistance and reactance value of an impedance 105. For each preset frequency, a particular impedance is found. The digital signal processor unit 413 calculates 205 and 206 by fitting the Cole circuit model to the measured impedance values. In the measuring environment, other passive elements with electrical properties are present as well. These are the stray capacitance 1, 204, the stray capacitance 2, 203 the excitation electrode resistance 1, 209, the excitation electrode resistance 2, 214, the sensory electrode resistance 1, 210, and the sensory electrode resistance 2, 212. To determine the value of the unknown circuit elements, an excitation current of sinusoidal form flows through the unknown circuit elements and the voltage signal measurements are taken at the same time at six measuring points 208, 320, 211, 213, 215, and 325. The excitation current comes from current sources 1 and 2, 403 and 404, where one of the two current sources injects the excitation current and the other sinks the current. The injecting and sinking function alternates between the current sources 403 and 404 every half period of the excitation frequency. The voltage signal is measured along the path of the measuring circuit, which starts off at earth potential 202, continues with 426, 403, 427, 325, 428, 324, 429, 208, 419, 410, 420, 209, and 216, branches off to 204, 202, 222, 205, and 221, and 218, 207, 219, 206, 205, and 220, merges at 217, branches off to 203, 202, 214, 421, 408, 422, 215, 423, 321, 424, 320, 425, 404, and ends at 202. An input logic circuit 327 and 328 is used to isolate or short circuit or leave unchanged preselected parts of the measurement circuit. The determination of the unknown lumped passive elements 105, 203, 204, 209, 210, 212, and 214 occurs with appropriate setting of the input logic circuit 327 and 328. Before each measurement cycle both offset voltage and voltage noise at six measuring points 208, 320, 211, 213, 215, and 325 are measured. These results are used later for elimination of offset error and minimization of voltage noise. The measurement cycle has two steps. With step one, the following are determined: the value of stray capacitance 1, 204, excitation electrode resistance 1, 209, sensory electrode resistance 1, 210, stray capacitance 2, 203, excitation electrode resistance 2, 214, and sensory electrode resistance 2, 212, using the input logic circuit 328 and 327 with appropriate setting of switches 1-15, 306, 307, 305, 309, 308, 311, 312, 313, 314, 315, 316, 317, 322, 310, and 323, respectively, and applying Ohm's law and Kirchhoff's first and second law.

In the second step, the following are determined: the unknown impedance or resistance and reactance of the human subject 105 at a preset frequency by using the input logic circuit 328 and 327 with appropriate setting of switches 1-15, 306, 307, 305, 309, 308, 311, 312, 313, 314, 315, 316, 317, 322, 310, and 323, respectively, and applying Ohm's law and Kirchhoff's first and second law. The magnitude of the offset voltage and amplitude as well as the phase angle of the voltage signal from measuring point 6, 326, measuring point 1, 208, and measuring point 3, 211, are referenced to reference resistance 1, 324, and from measuring point 2, 320, measuring point 5, 215, and measuring point 4, 213, are referenced to reference resistance 2, 321, respectively.

The measurement of resistance and reactance of the human subject at each preset frequency starts with loading a sine function of at least 16 wave lengths to a first in first out memory 401 by a microcontroller unit 412. Upon a trigger by the microcontroller unit 412, the train of at least 16 sine waves is sent to a digital-analog converter 402 at a predetermined rate by the microcontroller unit 412. The digital-analog converter 402 generates an excitation pattern with opposing phase for current source 1, 403, and current source 2, 404. Programmable gain instrumentation amplifiers within the microcontroller unit 412 pick up the voltage signals at the six measuring points 208, 320, 211, 213, 215, and 325 and amplify and filter the signal adjusted by the microcontroller within the microcontroller unit 412. The microcontroller unit 412 performs analog-digital conversion of the amplified and filtered voltage signal from the six measuring points 208, 320, 211, 213, 215 and 325. The microcontroller unit 412 then sends the signal first to the memory means of the microcontroller unit 412 and upon demand sends the signal to a digital signal processor unit 413. The digital signal processor unit 413 uses a sine wave function fitting algorithm to determine amplitude, phase, and offset of the digitized, amplified, and filtered voltage signal from the six measuring points 208, 320, 211, 213, 215 and 325 by minimizing the sum of the square of the deviations between the measured signal and a mathematical sine function of known frequency. The errors of the filtered voltage signal, defined as the difference between the predicted and measured digitalized, amplified, and filtered voltage signal from the six measuring points 208, 320, 211, 213, 215 and 325, are used for measurement of quality and to indicate whether a repeat measurement cycle is needed.

The digital processor unit 413 performs a non-linear curve fitting algorithm of the Cole circuit model to the measured resistances and reactances of human subject 105 at preset frequencies and extrapolates the best fitting Cole circuit model curve to zero and an extrapolated infinite frequency to obtain resistance of the human subject at zero and an extrapolated infinite frequency. The sum of the square of the deviations between Cole circuit model predicted and actually measured impedance values is used to measure quality and reliability of my apparatus' functioning.

FIG. 5A shows the detailed overview of the operation of the first method for the analysis of change of body composition and hydration status and for dynamic indirect individualized measurement of components of the human energy metabolism. The method starts at 1. The calculation for subsequent days merges with the start at 2. The algorithm branches off at decision point 3.

If this is an initiation day then the process continues at 5. The index variable for the day k is set to zero as expressed in Eq. 0. The initial values are entered for body cell mass $BCM_0$, extracellular water mass $ECW_0$, lean body mass $L_0$, intracellular water mass $ICW_0$, glycogen mass $G_0$, fat mass $F_0$, protein mass $P_0$, ingested carbohydrate intake $CI_0^\sim$, ingested fat intake $FI_0^\sim$, ingested protein intake $PI_0^\sim$, estimated correction factor for de novo lipogenesis $\mu_0$, estimated correction factor for gluconeogenesis from amino acids $\hat{v}_0$, and estimated correction factor for unidentified energy losses or gains $\hat{\varphi}_0$.

If this is not an initiation day then the process continues at 4 where the index variable for day k is set to a chosen value.

The algorithm branches off at decision point 6.

If this is a calibration day and the ingested macronutrient calories are available, the process continues at 7 with Eq. 1. to Eq. 3, which calculate the utilized macronutrient energy intake vector[27] from the ingested macronutrient intake.

[27] Hall, DOI: 10.1152/ajpendo.00559.2009

The algorithm branches off at decision point 600.

If a calculation with canonical representation using the R-ratio is chosen then the process will continue with an R-ratio method using a Canonical Model Form of the Human Energy Metabolism method. The serially measured lean body mass $L'_k$ and fat mass $F'_k$ is used throughout this algorithm where k runs from zero to the last day or day k. The measured values can come directly from process 19 or can be the result of smoothing as in process 24 or the result of a trajectory calculation as in process 25.

At decision point 601, the process branches off.

If the estimation of the R-ratio will be with fixed $\hat{a}_0=10400$, then the process continues at process 602. The goal is to find the best R-ratio estimate $\hat{R}_k$ which would achieve the closest approximation of the vector with elements of daily lean body mass changes $DL'_k$ to the product of R-ratio estimate $\hat{R}_k$ and vector with elements of daily fat mass changes $DF'_k$ with lowest sum of squared errors as in Eq. 200. The vector with elements of daily lean body mass changes $DL'_k$ is defined in Eq. 201 and the vector with elements of daily fat mass changes $DF'_k$ is defined in Eq. 202. This estimation with minimum least square error can be done as in Eq. 203 or using the data recursive least square estimation as in Eq. 204. The Kalman gain $KR_k$ for R-ratio is calculated as in Grewal.[28] The indirectly calculated estimation R-ratio $\hat{R}^*_{k-1}$ is calculated as in Eq. 205. The process continues with decision point 604.

[28] Grewal M. S. and A. P. Andrews. Kalman Filtering: Theory and Practice Using MATLAB. John Wiley & Sons, New Jersey. Third Ed.; September 2011, 136 pp.

If the estimation of the R-ratio will be with slowly drifting $\hat{a}_k$ on day k then the process continues at process 603. The goal is to find the best R-ratio estimate $\hat{R}_k$ which would achieve the closest approximation of the vector with elements of daily lean body mass $LL'_k$ to the product of vector with elements of the natural logarithm of the daily fat mass $LF'_k$ and the parameter vector of the lean body mass-fat mass interrelationship $\hat{p}_k$ as in Eq. 206. The vector with elements of daily lean body mass $LL'_k$ is defined in Eq. 207 and the vector with elements of the natural logarithm of the daily fat mass $LL'_k$ is defined in Eq. 208. The vector parameter of lean body mass-fat mass interrelationship $\hat{p}_k$ is defined in Eq. 206a. The estimation of $\hat{p}_k$ with minimum least square error can be done as in Eq. 209 or using the data recursive least square estimation as in Eq. 210. The Kalman gain matrix $Kp_k$ is calculated as in Grewal.[29] The calculation of the parameter vector of the lean body mass-fat mass inter relationship $p^*_k$ on day k is in Eq. 211. $\hat{R}_k$ is estimated in Eq. 212. The process continues with decision point 604.

[29] Grewal M. S. and A. P. Andrews. Kalman Filtering: Theory and Practice Using MATLAB. John Wiley & Sons, New Jersey. Third Ed.; September 2011, 136 pp.

The algorithm branches off at decision point 604.

If individualized estimation of daily energy density of the lean body mass change $\varrho_{L_k}$ and daily energy density of the fat mass change $\varrho_{F_k}$ is needed, then the process continues at 606. Here the coefficient of daily energy balance and lean mass change interrelationship $\hat{A}_k$ and the coefficient of daily energy balance and fat mass change interrelationship $\hat{B}_k$ are estimated with the goal of error least square for $\hat{A}_k$ as in Eq. 215 and for $\hat{B}_k$ as in Eq. 216. The definition of the vector with elements of daily energy balance values $DIO'_k$ is as in Eq. 217. The definition of the vector with elements of daily lean body mass changes $DL'_k$ is as in Eq. 218. The definition of the vector with elements of daily fat mass changes $DF'_k$ is as in Eq. 219. The estimation of $\hat{A}_k$ with minimum least square error can be done as in Eq. 220a or using the data recursive least square estimation as in Eq. 221. The Kalman gain $KA_k$ is calculated as in Grewal.[30] The indirectly calculated coefficient of daily energy balance and lean mass change interrelationship $\hat{A}^*k$ is calculated as in Eq. 223. The estimation of $\hat{B}_k$ with minimum least square error can be done as in Eq. 220b or using the data recursive least square estimation as in Eq. 222. The Kalman gain $KB_k$ is calculated as in Grewal.[31] The indirectly calculated coefficient of daily energy balance and lean mass change interrelationship $\hat{B}^*_k$ is calculated as in Eq. 224. The indirectly calculated daily energy density of the fat mass change $\varrho^*_{F_k}$ is calculated in Eq. 225a if there was a fat mass gain on previous day or in Eq. 225b if there was no fat mass gain on previous day. The indirectly calculated daily energy density of the lean body mass change $\varrho^*_{L_k}$ is calculated in Eq. 226. The estimated daily energy density of the fat mass change $\hat{\varrho}_{F_k}$ is calculated in Eq. 227. The estimated daily energy density of the lean body mass change $\hat{\varrho}_{L_k}$ is calculated in Eq. 228. The Kalman gains $K\varrho_{F_k}$ and $K\varrho_{L_k}$ are calculated as in Grewal.[32] The process continues with decision point 607.

[30] Id.
[31] Id.
[32] Id.

If individualized estimation of daily energy density of the lean body mass change $\hat{\varrho}_{L_k}$ and daily energy density of the fat mass change $\hat{\varrho}_{F_k}$ are not needed, then the process continues with 605 and $\varrho_{L_k}$ takes up its default value as in Eq. 213 and $\varrho_{F_k}$ takes up its default value as in Eq. 214. The process continues with decision point 607.

At process 607 the gluconeogenesis from protein is calculated with Eq. 229-Eq. 233. In the next process step 608 the macronutrient oxidations are calculated. The protein oxidation is calculated in Eq. 234 using the protein mass indirectly calculated with measured values $\Delta P^{*\prime}_{k+1}$. The daily change $\Delta P^{*\prime}_{k+1}$ is calculated in Eq. 235. The rate of fat oxidation is calculated in Eq. 236. The rate of carbohydrate oxidation is calculated in Eq. 237. In the next process 609 the energy flux from carbohydrate pool to fat pool $\hat{\sigma}_k$ is estimated as in Eq. 238. The indirectly calculated parameter for energy flux from carbohydrate pool to fat pool $\sigma^*_k$ is calculated as in in Eq. 239. The Kalman gain $K\sigma_k$ is calculated as in Grewal.[33] In the next process 610 the estimation of parameter for uncounted energy $\hat{\omega}_k$ is performed as in Eq. 240. The indirectly calculated parameter for uncounted energy $\omega^*_k$ is calculated as in Eq. 241. The Kalman gain $K\omega_k$ is calculated as in Grewal.[34] In the next process 611 the Self-Adaptive Input Output Model of the Human Energy Metabolism (SIO-HEM) is shown. In Eq. 242 the daily change of the lean body $\Delta L_{k+1}$ mass is calculated. In Eq. 243 the daily change of the fat mass $\Delta F_{k+1}$ is calculated. In Eq. 244 the daily change of the protein mass $\Delta P_{k+1}$ is calculated. In the next process 612 the estimator equations of the Self-Adaptive Input Output Model of the Human Energy Metabolism (SIO-REM) are shown. In Eq. 245 estimated daily change of the lean body mass at end of day k $\Delta L_{k+1}$ is calculated. In Eq. 246 estimated daily change of the fat mass at end of day k $\Delta P_{k+1}$ is calculated. In Eq. 247 estimated daily change of the protein mass at end of day k $\Delta P_{k+1}$ is calculated. In Eq. 248 the deviation of estimated lean body mass from measured lean body mass $\delta L_k$ is calculated. In Eq. 249 the deviation of estimated fat mass from measured fat mass $\delta F_k$ is calculated. In Eq. 250 the deviation of estimated protein mass from measured protein mass $\delta P_k$ is calculated. In Eq. 251 the protein mass indirectly calculated with measured values $P^{*\prime}_k$ is calculated.

[33] Id.
[34] Id.

In the next process 613 the Canonical Model Form of the Human Energy Metabolism (C-HEM) is shown. In Eq. 252 the lean body mass $L_{k+1}$ at the end of day k is calculated. In Eq. 253 the fat mass $F_{k+1}$ at the end of day k is calculated. In Eq. 254 the protein mass $P_{k+1}$ at the end of day k is calculated. In the next process 614 the estimator equations of the Canonical Model Form of the Human Energy Metabolism (C-HEM) are shown. In Eq. 255 the estimation of the lean body mass $\hat{L}_{k+1}$ at the end of day k is calculated. In Eq. 256 the estimation of fat mass $\hat{F}_{k+1}$ at the end of day k is calculated. In Eq. 257 the estimation of protein mass $\hat{P}_{k+1}$ at the end of day k is calculated.

In the next process 615 inverse calculation of utilized macronutrient intake using trajectory values of the body composition changes is shown. In matrix equation Eq. 258 the estimated utilized carbohydrate intake $\widehat{CI}_k$, the estimated utilized fat intake $\widehat{FI}_k$, and the estimated utilized protein intake $\widehat{PI}_k$ are calculated from known change of lean body mass trajectory on day k $\Delta L^*_{k+1}{}^{TR}$, change of fat mass trajectory on day k $\Delta L^*_{k+1}{}^{TR}$, and change of protein mass trajectory on day k $\Delta P^*_{k+1}{}^{TR}$. The trajectory values can come from indirectly measured data as generated by process 19 as indicated in Eq. 260 or can be the result of smoothing as in process 24 or trajectory calculation as process 25. The indirectly measured $Nexcr^{*\prime}_k$ can be calculated as in Eq. 259.

The process continues at 44. If at decision point 600 no calculation with canonical representation using the R-ratio is chosen, then the process continues at 9.

At process 9, Eq. 4. calculates the rate of proteolysis and Eq. 5. calculates the rate of glycogenolysis. Eq. 6. calculates the fat store dependent coefficient for rate of endogenous lipolysis on day k. Eq. 7. calculates the carbohydrate intake dependent coefficient for rate of endogenous lipolysis. Eq. 8. calculates the bias for rate of endogenous lipolysis on day k. Eq. 9. calculates the rate of endogenous lipolysis on day k. Eq. 10. calculates the carbohydrate intake dependent coefficient for rate of de novo lipogenesis. Eq. 11. calculates the glycogen store dependent coefficient for rate of de novo lipogenesis on day k. Eq. 12. calculates bias for rate of endogenous lipolysis on day k. Eq. 13. calculates the rate of de novo lipogenesis. Eq. 14. calculates the rate of glycerol gluconeogenesis. Eq. 15. calculates the protein store dependent coefficient for gluconeogenesis from protein. Eq. 16. calculates the carbohydrate intake dependent coefficient for gluconeogenesis from protein. Eq. 17. calculates the protein intake dependent coefficient for gluconeogenesis from protein. Eq. 18. calculates the bias for gluconeogenesis from protein. Eq. 19. calculates the rate of gluconeogenesis from protein. Eq. 20. calculates the glycerol 3-phosphate synthesis. Eq. 21. calculates the resting metabolic rate with a filtering formula on day k. Eq. 22. calculates the indirectly calculated total energy expenditure from the resting metabolic rate with the filtering formula on day k and directly measured physical activity energy expenditure. Eq. 23. calculates the 24 hour nitrogen excretion from utilized protein intake on day k and the daily change of the protein store for day k−1. The process continues at 16.

If at decision point 6 this is not a calibration day and the ingested macronutrient calories are not available, the process continues at decision point 8.

If there is no trajectory value $\Delta BC_{k+1}{}^{TR*}$, called the change of trajectory of indirectly calculated change of body composition vector of day k, available for $\Delta BC^*_{k+1}$, called the indirectly calculated change of body composition vector of day k, at decision point 8, then the algorithm continues with process 10.

At process 10, Eq. 24. shows the calculation of the rate of proteolysis on day k. Eq. 25. calculates the rate of glycogenolysis on day k. Eq. 26. calculates the fat store dependent coefficient for the rate of endogenous lipolysis on day k. Eq. 27. calculates the carbohydrate intake dependent coefficient for the rate of endogenous lipolysis on day k. Eq. 28.

calculates the bias for the rate of endogenous lipolysis on day k. Eq. 29. calculates the rate of endogenous lipolysis on day k. Eq. 30. calculates the carbohydrate intake dependent coefficient for the rate of de novo lipogenesis on day k. Eq. 31. calculates the glycogen store dependent coefficient for the rate of de novo lipogenesis on day k. Eq. 32. calculates the bias for the rate of endogenous lipolysis on day k. Eq. 33. calculates the rate of de novo lipogenesis on day k. Eq. 34. calculates the rate of glycerol gluconeogenesis on day k. Eq. 35. calculates the protein store dependent coefficient for gluconeogenesis from protein on day k. Eq. 36. calculates the carbohydrate intake dependent coefficient for gluconeogenesis from protein on day k. Eq. 37. calculates the protein intake dependent coefficient for gluconeogenesis from protein on day k. Eq. 38. calculates the bias for gluconeogenesis from protein on day k. Eq. 39. calculates the rate of gluconeogenesis from protein on day k. Eq. 40. calculates a part of the resting metabolic rate which is independent of the body composition vector changes and the time-varying constant energy expenditure on day k. Eq. 41. calculates the resting metabolic rate with predictive formula on day k. Eq. 42. calculates a part of the resting metabolic rate which is dependent on the utilized carbohydrate intake on day k. Eq. 43. calculates a part of the resting metabolic rate which is dependent on the utilized fat intake on day k. Eq. 44. calculates a part of the resting metabolic rate which is dependent on the utilized protein intake on day k. The process continues at 11.

At process 11, Eq. 45. constructs the energy constant matrix of the Retained or Released Energy Model of the Human Energy Metabolism on day k. Eq. 46. constructs the time varying utilized energy intake coupling matrix in the Retained or Released Energy Model of the Human Energy Metabolism on day k. Eq. 47. constructs the indirectly calculated bias vector of the Retained or Released Energy Model of the Human Energy Metabolism on day k. Eq. 48. calculates the utilized energy intake vector indirectly with the Measurement Model of the Utilized Energy Intake from body composition vector change on day k, which I obtain either from Eq. 117. or Eq. 119. where I obtain the lean body mass change and fat mass change from 107, which is part of 109, the device and method for body composition and hydration status analysis. Eq. 49. assigns the value of the utilized carbohydrate intake indirectly calculated by the Measurement Model of the Utilized Energy Intake from body composition vector change on day k to the variable for the utilized carbohydrate intake on day k. Eq. 50. assigns the value of the utilized fat intake indirectly calculated by the Measurement Model of the Utilized Energy Intake from body composition vector change on day k to the variable for the utilized fat intake on day k. Eq. 51. assigns the value of the utilized protein intake indirectly calculated by the Measurement Model of the Utilized Energy Intake from body composition vector change on day k to the variable for the utilized protein intake on day k. The process continues at process 9.

If there is a trajectory value $\Delta BC_{k+1}^{TR*}$, called the change of trajectory of indirectly calculated change of body composition vector of day k, available for $\Delta BC^*_{k+1}$, called the indirectly calculated change of body composition vector of day k, at decision point 8, then the algorithm continues with process 12.

At process 12, Eq. 52. shows the calculation of the rate of proteolysis on day k−1. Eq. 53. calculates the rate of glycogenolysis on day k−1. Eq. 54. calculates the fat store dependent coefficient for the rate of endogenous lipolysis on day k−1. Eq. 55. calculates the carbohydrate intake dependent coefficient for the rate of endogenous lipolysis on day k−1. Eq. 56. calculates the bias for the rate of endogenous lipolysis on day k−1. Eq. 57. calculates the rate of endogenous lipolysis on day k−1. Eq. 58. calculates the carbohydrate intake dependent coefficient for the rate of de novo lipogenesis on day k−1. Eq. 59. calculates the glycogen store dependent coefficient for the rate of de novo lipogenesis on day k−1. Eq. 60. calculates the bias for the rate of endogenous lipolysis on day k−1. Eq. 61. calculates the rate of de novo lipogenesis on day k−1. Eq. 62. calculates the rate of glycerol gluconeogenesis on day k−1. Eq. 63. calculates the protein store dependent coefficient for gluconeogenesis from protein on day k−1. Eq. 64. calculates the carbohydrate intake dependent coefficient for gluconeogenesis from protein on day k−1. Eq. 65. calculates the protein intake dependent coefficient for gluconeogenesis from protein on day k−1. Eq. 66. calculates the bias for gluconeogenesis from protein on day k−1. Eq. 67. calculates the rate of gluconeogenesis from protein on day k−1. Eq. 68. calculates a part of the resting metabolic rate which is independent of the body composition vector changes and the time-varying constant energy expenditure on day k−1. Eq. 69. calculates the resting metabolic rate with predictive formula on day k−1. Eq. 70. calculates a part of the resting metabolic rate which is dependent on the utilized carbohydrate intake on day k−1. Eq. 71. calculates a part of the resting metabolic rate which is dependent on the utilized fat intake on day k−1. Eq. 72. calculates a part of the resting metabolic rate which is dependent on the utilized protein intake on day k−1. The process continues at 13.

At process 13, Eq. 73. shows the calculation of rate of proteolysis on day k. Eq. 74. calculates the rate of glycogenolysis on day k. Eq. 75. calculates the fat store dependent coefficient for rate of endogenous lipolysis on day k. Eq. 76. calculates carbohydrate intake dependent coefficient for rate of endogenous lipolysis on day k. Eq. 77. calculates the bias for rate of endogenous lipolysis on day k. Eq. 78. calculates the rate of endogenous lipolysis on day k. Eq. 79. calculates the carbohydrate intake dependent coefficient for the rate of de novo lipogenesis on day k. Eq. 80. calculates the glycogen store dependent coefficient for the rate of de novo lipogenesis on day k. Eq. 81. calculates the bias for the rate of endogenous lipolysis on day k. Eq. 82. calculates the rate of de novo lipogenesis on day k. Eq. 83. calculates the rate of glycerol gluconeogenesis on day k. Eq. 84. calculates the protein store dependent coefficient for gluconeogenesis from protein on day k. Eq. 85. calculates the carbohydrate intake dependent coefficient for gluconeogenesis from protein on day k. Eq. 86. calculates the protein intake dependent coefficient for gluconeogenesis from protein on day k. Eq. 87. calculates the bias for gluconeogenesis from protein. Eq. 88. calculates the rate of gluconeogenesis from protein on day k. Eq. 89. calculates a part of the resting metabolic rate that is independent of the body composition vector changes and the time-varying constant energy expenditure on day k. Eq. 90. calculates the resting metabolic rate with a predictive formula on day k. Eq. 91. calculates a part of the resting metabolic rate which is dependent on the utilized carbohydrate intake on day k. Eq. 92. calculates a part of the resting metabolic rate which is dependent on the utilized fat intake on day k. Eq. 93. calculates a part of the resting metabolic rate which is dependent on the utilized protein intake on day k. The process continues at 14.

At process 14, Eq. 94. constructs the time varying utilized energy intake coupling matrix in the Retained or Released Energy Model of the Human Energy Metabolism on day k−1. Eq. 95. constructs the indirectly calculated bias vector of the Retained or Released Energy Model of the Human Energy Metabolism on day k−1. Eq. 96. constructs the time varying utilized energy intake coupling matrix in the Retained or Released Energy Model of the Human Energy Metabolism on day k. Eq. 97. constructs the indirectly calculated bias vector of the Retained or Released Energy Model of the Human Energy Metabolism on day k. Eq. 98. calculates the dynamic transition matrix in the Self-Correcting Model of the Utilized Energy Intake on day k−1. Eq. 99. calculates dynamic coupling matrix in the Self Corrective Model of the Utilized Energy Intake on day k−1. Eq. 100. calculates the time varying bias vector in the Self Corrective Model of the Utilized Energy Intake on day k−1. Eq. 101. calculates the utilized energy intake vector, with the elements consisting of the daily metabolized macronutrient intake from carbohydrate, fat and protein on day k. I refer to Eq. 101. as the Linear Model of the Utilized Energy Intake, and this linear model also serves as the process model of the Self-Correcting Model of the Utilized Energy Intake. Eq. 102. calculates the indirectly measured utilized energy intake vector on day k using the Retained or Released Energy Model of the Human Energy Metabolism, and I refer to Eq. 102. as the Measurement Model of the Utilized Energy Intake from body composition vector change. The input variable to Eq. 102. is the indirectly calculated change of body composition vector of day k, which I obtain either from Eq. 117. or Eq. 119. where the lean body mass change and fat mass change from 107 are obtained, which is part of 109, the device and method for body composition and hydration status analysis. The process continues at process 15.

At process 15, the deviation of the estimated indirectly calculated utilized energy intake vector is evaluated with one of two optional equations, Eq. 103. or Eq. 104. Eq. 103. calculates the deviation of the estimated indirectly calculated utilized energy intake vector from the indirectly measured utilized energy intake vector on day k using the indirectly calculated change of body composition vector of day k and the Measurement Model of the Utilized Energy Intake. Eq. 104. calculates the deviation of the estimated indirectly calculated utilized energy intake vector from a trajectory using the change of trajectory of indirectly calculated change of body composition vector of day k and the Measurement Model of the Utilized Energy Intake. Eq. 105. implements the discrete time Kalman estimator with innovations representation for the daily utilized macronutrient energy intake vector using the Self-Correcting Model of the Utilized Energy Intake with innovations representation. The Kalman gain matrix is calculated as in Grewal, (Grewal M. S. and A. P. Andrews. Kalman Filtering: Theory and Practice Using MATLAB. John Wiley & Sons, New Jersey. Third Ed.; September 2011, 136 pp.). Eq. 106. assigns the estimated indirectly calculated utilized energy intake vector by the Self-Correcting Model of the Utilized Energy Intake on day k to the utilized energy intake vector with elements of daily metabolized macronutrient intake of carbohydrate, fat, and protein on day k. The process continues at 9.

At process 16, the macronutrient oxidation rates are calculated. Eq. 107. constructs the oxygen caloric heat equivalent constants matrix. Eq. 108. constructs the indirectly calculated heat energy equivalent vector on day k. Eq. 109. calculates the indirectly calculated macronutrient oxidation vector with the elements of energy content obtained after oxidation of carbohydrate, fat, and protein on day k. Eq. 110. assigns the values of the components of the macronutrient oxidation vector to variables of the calculated rate of carbohydrate oxidation, calculated rate of fat oxidation, and calculated rate of protein oxidation. The process continues at 17.

The process at 17 shows the process model of the Linear Extended Model of the Human Energy Metabolism. Eq. 111. calculates the daily energy of the glycogen store change for day k. Eq. 112. calculates the daily energy of fat store change for day k. Eq. 113. calculates the daily energy of protein store change for day k. The calculations in Eq. 111. to Eq. 113. are represented also in Eq. 114. with a matrix representation to calculate the change of body composition vector at the end of day k.

The algorithm branches off at decision point 18 and reunites again at 21. The measurement model can be either the Measurement Model of Body Composition Change from Lean-Fat-Protein as in Eq. 115. to Eq. 117. at process 19 or the Measurement Model of Body Composition Change from Lean-Fat-Resting Metabolic Rate as in Eq. 118. to Eq. 119. at process 20. Eq. 115. calculates daily change of the indirectly calculated body protein mass on day k. Eq. 116. calculates the change of the indirectly calculated lean-fat-protein vector of day k. Eq. 117. calculates the indirectly calculated change of body composition vector for day k, where I obtain the lean body mass change and fat mass change from 107, which is part of 109, the device and method for body composition and hydration status analysis. I refer to Eq. 117 as the Measurement Model of Body Composition Change from Lean-Fat-Protein. The algorithm continues at 21.

At process 20, Eq. 118 is the change of the indirectly calculated lean-fat-resting-metabolic-rate vector of day k. Eq. 119 calculates the indirectly calculated change of body composition vector for day k where I obtain the lean body mass change and fat mass change from 107, which is part of 109, the device and method for body composition and hydration status analysis. I refer to Eq. 119. as the Measurement Model of Body Composition Change from Lean-Fat-Resting-Metabolic-Rate. The algorithm continues at 21.

At process 21, the deviation of the estimated indirectly calculated change of body composition vector is evaluated with one of three optional equations, Eq. 120, Eq. 121, or Eq. 122. Eq. 120 calculates the deviation of the estimated indirectly calculated change of body composition vector of day k from the indirectly measured one using the Measurement Model of Body Composition Change from Lean-Fat-Protein. Eq. 121 calculates the deviation of the estimated indirectly calculated change of body composition vector of day k from the indirectly measured one using the Measurement Model of Body Composition Change from Lean-Fat-Resting-Metabolic-Rate. Eq. 122 calculates the deviation of the estimated indirectly calculated change of body composition vector from a trajectory on day k. Eq. 123 implements the discrete time variant Kalman estimator with innovations representation for the estimation of the indirectly calculated change of body composition of day k. In this equation, I use the Self-Adaptive Model of the Human Energy Metabolism and innovations representation technique. The resulting estimates of the daily body composition change of day k allow for stochastic identification of the correction factors for de novo lipogenesis, gluconeogenesis from amino acids, and the correction factor for unidentified energy losses or gains, so that these model parameters become Self-Adaptive. The Kalman gain matrices are calculated as in Grewal.[35] The algorithm continues at 22.

[35] Grewal M. S. and A. P. Andrews. Kalman Filtering: Theory and Practice Using MATLAB. John Wiley & Sons, New Jersey. Third Ed.; September 2011, pp. 136

At process 22, the estimators for the correction factors for de novo lipogenesis, gluconeogenesis from amino acids, and for unidentified energy losses or gains are shown in Eq. 124 to Eq. 126 Eq. 124 sets the a posteriori estimation of the correction factor for de novo lipogenesis of day k equal to the a priori estimation of the correction factor for de novo lipogenesis of day k+1. Eq. 125 sets the a posteriori estimation of the correction factor for gluconeogenesis of day k equal to the a priori estimation of the correction factor for gluconeogenesis of day k+1. Eq. 126 sets the a posteriori estimation of the correction factor for unidentified energy losses or gains of day k equal to the a priori estimation of the correction factor for unidentified energy losses or gains of day k+1. The measurement equations for the correction factors for de novo lipogenesis, gluconeogenesis from amino acids, and for unidentified energy losses or gains are calculated as in Eq. 127 to Eq. 129. The a posteriori estimation of the correction factors for de novo lipogenesis, gluconeogenesis from amino acids, and for unidentified energy losses or gains is performed using the Kalman filter as in Eq. 130 to Eq. 132. The Kalman gains are calculated as a scalar problem as in Grewal.[36] The algorithm continues at 23.

[36] Grewal M. S. and A. P. Andrews. Kalman Filtering: Theory and Practice Using MATLAB. John Wiley & Sons, New Jersey. Third Ed.; September 2011, pp. 140

The algorithm branches off at decision point 23.

If no calibrations are desired than the process continues at decision point 26.

If this is a calibration day j with known ingested carbohydrate, fat, and protein calories; a known calibration value for body composition vector; and a trajectory calculation for body composition vector changes is desired, then a smoothing procedure of the indirectly calculated body composition vector change is performed and the process continues at 24. It may be preferable to use optimal smoothers.[37] The process continues at 25.

[37] Grewal M. S. and A. P. Andrews. Kalman Filtering: Theory and Practice Using MATLAB. John Wiley & Sons, New Jersey. Third Ed.; September 2011, pp. 183

At process 25, the trajectory calculation is performed. My first embodiment uses the smoothed values of the indirectly measured body composition vector. The time interval for the trajectory is day i, which is the day of the previous calibration, to day j, which is the day of the last calibration. The constraint is that the trajectory starts with a calibration value of day i and ends with a calibration value of day j for the body composition vector. Eq. 133 calculate the trajectory of the body composition vector from day i to day j using the results of the smoothing algorithm. Alternative methods of trajectory creation include using mathematical methods[38] which express the function of the trajectory as a parametric curve. Eq. 134 calculates the trajectory of the body composition vector from day i to day j using a polynomial spline function. Eq. 135 calculates the trajectory of the body composition vector from day i to day j using a B spline function. Eq. 136 calculates the trajectory of the body composition vector from day i to day j using a Bezier function. The algorithm continues at 26 and branches off at decision point 26. If no calibrations for the adjustable coefficients to calculate extracellular water and intracellular water masses are needed, then the process continues at 29.

[38] Venkataraman, P. Applied Optimization with MATLAB Programming. March 2009; John Wiley & Sons, pp. 490

If a calibration procedure for the adjustable coefficients to calculate extracellular water and intracellular water masses is needed, then the process continues at 27 and reference values are generated first. The reference value for extracellular water mass on calibration day j is obtained from tabled values[39] as shown in Eq. 137, where the values are dependent on weight, height, age, sex and race. The reference value for intracellular water mass on calibration day j is calculated in Eq. 140.[40] The formula requires the body weight and the reference value for fat mass on calibration day j. The reference value for fat mass on calibration day j is obtained from the anthropomorphic determination of body fat as in Lean[41], as in Eq. 138 for men and Eq. 139 for women. Eq. 141 calculates the reference value for the lean body mass.

[39] Silva, DOI:10.1088/0967-3334/28/5/004
[40] Jaffrin, DOI: 10.1016/j.medengphy.2008.06.009
[41] Lean, et al. Predicting body composition vector by densitometry from simple anthropometric measurements. American Journal of Clinical Nutrition, January 1996; 63(1): 4-14

The calibration process proceeds to 28, where the adjustable coefficients to calculate extracellular water and intracellular water masses are estimated. Eq. 142. sets the a posteriori estimation of the adjustable coefficient to calculate extracellular water on calibration day i equal to the a priori estimation of the adjustable coefficient to calculate extracellular water on day j. Eq. 143. sets the a posteriori estimation of the adjustable coefficient to calculate intracellular water on calibration day i equal to a priori estimation of the adjustable coefficient to calculate intracellular water on day j. The measurement equations for the adjustable coefficients to calculate extracellular water and intracellular water masses are calculated as in Eq. 144. to Eq. 145. The a posteriori estimation of the adjustable coefficients to calculate extracellular water and intracellular water masses is performed using the Kalman filter as in Eq. 146 and Eq. 147. The Kalman gains are calculated as a scalar problem as in Grewal.[42] The algorithm continues at 29.

[42] Grewal M. S. and A. P. Andrews. Kalman Filtering: Theory and Practice Using MATLAB. John Wiley & Sons, New Jersey. Third Ed.; September 2011, pp. 140

The algorithm branches off at decision point 29. If no measurement of the body composition vector and daily change in body composition vector is needed, then the process continues at decision point 31.

If measurement of the body composition vector and daily change in body composition vector is needed, then these can be calculated at process 30. Eq. 148 calculates the extracellular water mass from the resistance extrapolated at zero frequency. Eq. 149 calculates the intracellular water mass from the resistance at an extrapolated infinite frequency. The lean body mass is calculated with Eq. 150.[43] The body fat mass is obtained by subtracting the lean body mass from body weight as in Eq. 151. The lean body change from one day to the next day is obtained by subtracting the previous day's lean body mass from the next day's lean body mass as in Eq. 152. The daily fat mass change is obtained by subtracting the daily change of lean body mass from the daily body weight change as in Eq. 153. The algorithm continues at 31.

[43] Jaffrin, DOI: 10.1016/j.medengphy.2008.06.009

The algorithm branches off at decision point 31. If no calibration procedure for the adjustable dynamic coefficients to calculate extracellular water and intracellular water mass changes is needed, then the process continues at decision point 33.

If a calibration procedure for the adjustable dynamic coefficients to calculate extracellular water and intracellular water mass changes is needed, then the process continues at 32.

At process 32, a calibration procedure is performed for the adjustable dynamic coefficients to calculate extracellular water mass and intracellular water mass changes. In calculating dynamic changes of extracellular water and intracellular water, I take advantage of the observation that the ratio of the extracellular and total body water is tightly regulated in normal physiology.[44] The ratio can be calculate using reference values on day j. The ratio of the extracellular and total body water is determined from reference extra cellular water and intracellular water mass as in Eq. 154.

[44] Ellis K J, Wong W W (1998) Human hydrometry: comparison of multi-frequency bioelectrical impedance with $^2H_2O$ and bromine dilution. J Appl Physiol 85(3): 1056-1062

For the calibration of the acute change of extracellular and intracellular water mass, a known change of the total water mass is needed in a relatively short period of time so as not to affect the body composition vector change. Vigorous perspiration or rapid hydration with fluid can be such a sentinel event when the body loses or gains a measurable weight in a short period of time without any significant change of the body composition. The ensuing body weight change, and equivalently, the total body water change from the beginning to the end of the sentinel event causes the hydration change. The indirectly calculated extracellular water change for this scenario can be calculated as in Eq. 155. Eq. 155 requires the knowledge of the total water change of the body which can be obtained by measuring the weight before and after a sentinel event and calculating the difference. The ensuing change of the intracellular water is calculated in Eq. 156. Eq. 157 sets the a posteriori estimation of the adjustable dynamic coefficient to calculate extracellular water on calibration day i equal to the a priori estimation of the adjustable dynamic coefficient to calculate extracellular water on day j. Eq. 158 sets the a posteriori estimation of the adjustable dynamic coefficient to calculate intracellular water on calibration day i equal to the a priori estimation of the adjustable dynamic coefficient to calculate intracellular water on day j. The measurement equations for the adjustable dynamic coefficients to calculate extracellular and intracellular water masses are calculated in Eq. 159 to Eq. 160. The a posteriori estimation of the adjustable dynamic coefficients to calculate extracellular and intracellular water masses is performed using the Kalman filter in Eq. 161 and Eq. 162 and the Kalman gains are calculated as a scalar problem as in Grewal.[45] The algorithm continues at decision point 33.

[45] Grewal M. S. and A. P. Andrews. Kalman Filtering: Theory and Practice Using MATLAB. John Wiley & Sons, New Jersey. Third Ed.; September 2011, page 140

The algorithm branches off at decision point 33. If no measurement of acute change of hydration status is needed, then the process continues at decision point 35.

If measurement for acute change of hydration status is needed, then the process continues at 34. Eq. 163 calculates dynamic changes of extracellular water indirectly from resistance value changes before and after the acute event causing hydration status change using the resistance extrapolated at zero frequency before and after a sentinel event of hydration status change. Eq. 164 calculates dynamic changes of intracellular water indirectly from resistance value changes before and after the acute event causing hydration status change using the resistance at an extrapolated infinite frequency before and after a sentinel event of hydration change. The process continues at decision point 35 and branches off at decision point 35. If no calibration procedure for the estimation of the time varying constant energy expenditure is needed, the process continues at 37.

If a calibration procedure for the estimation of the time varying constant energy expenditure is needed, then the process continues at 36. Eq. 165 sets the a posteriori estimation of the time varying constant energy expenditure of the previous calibration day i equal to the a priori estimation of the time varying constant energy expenditure of the last calibration day j. The measurement equation for the time-varying constant energy expenditure for calibration day j is calculated as in Eq. 166. In this equation, the components of the indirectly calculated body composition vector change are entered, taken from the day before the calibration day j. Next, the a posteriori estimation of the time-varying constant energy expenditure is performed using the Kalman filter as in Eq. 167, and the Kalman gains are calculated as a scalar problem as in Grewal.[46] The process continues at decision point 37.

[46] Id.

At decision point 37, if no calibration procedure for the basal gluconeogenesis rate is needed, the process continues at process 38. If a new value for the basal gluconeogenesis rate after previous calibration on day j is available than an estimated gluconeogenesis from protein on day k with calibration can be calculated as in Eq. 170 by multiplying the new value for the basal gluconeogenesis rate after calibration on day j with the estimation of the correction factor for gluconeogenesis from amino acids on day k and the gluconeogenesis from protein on day k and dividing the result with the old basal gluconeogenesis rate before calibration. The process continues at decision point 40.

At decision point 37, if a calibration procedure for the basal gluconeogenesis rate is needed, then the process continues at 39. For this calibration procedure, the measured nitrogen excretion on calibration day j is required. Eq. 168 calculates the indirectly measured correction factor for gluconeogenesis from amino acids on calibration day j by evaluating a ratio with the numerator being the product of six point twenty-five multiplied with the energy density of protein and multiplied with the measured nitrogen excretion on calibration day j minus the calculated rate of protein oxidation rate on day j, divided by the gluconeogenesis from protein on day j. The indirectly measured correction factor for gluconeogenesis from amino acids on calibration day j could be used for the process equation Eq. 125 allowing for calibrated estimation of the gluconeogenesis from protein. Eq. 169 calculates the new value for the basal gluconeogenesis rate after previous calibration on day j by adding up the product of six point twenty-five multiplied with the energy density of protein, and multiplied with the measured nitrogen excretion on calibration day j minus the calculated rate of protein oxidation rate on day j. The process continues at decision point 40.

At decision point 40, if no calibration procedure for baseline lipolysis rate is needed, then the process continues at 41. If a new value for the baseline lipolysis rate after previous calibration on day j is available than an estimated rate of endogenous lipolysis on day k with calibration can be calculated as in Eq. 173 by multiplying the new value for the baseline lipolysis rate after calibration on day j with the estimation of the correction factor for de novo lipogenesis on day k and the rate of endogenous lipolysis on day k and dividing the result by the old baseline lipolysis rate before calibration. The process continues at decision point 43.

At decision point 40, if a calibration procedure for baseline lipolysis rate is needed, then the process continues at 42. For the calibration procedure, the measured rate of endogenous lipolysis on calibration day j is required. Eq. 171 calculates the indirectly measured correction factor for de novo lipogenesis on calibration day j by calculating the ratio of the baseline lipolysis rate before calibration and the measured rate of endogenous lipolysis on calibration day j.

The indirectly measured correction factor for de novo lipogenesis on calibration day j could be used for the process equation Eq. 124 allowing for calibrated estimation of the rate of endogenous lipolysis. Eq. 172 calculates the new value for the baseline lipolysis rate after previous calibration on day j by equating it with the measured rate of endogenous lipolysis on calibration day j. The process continues at decision point 43.

At process 43, preparations are made to proceed with calculations for the next day. Eq. 173. increases the index variable for day k by one. Eq. 174 calculates the time-varying constant energy expenditure on day k+1.

At process 44, the entire calculation for the next day can be performed by proceeding from 44 to 2.

Thus, at least one embodiment of the apparatus and method for the analysis of the change of body composition and hydration status and for dynamic indirect individualized measurement of components of the human energy metabolism provides several advantages. The advantages of the apparatus include, but are not limited to:
1. Measuring and correcting for stray capacitances.
2. Minimizing input noise and reduces capacitances of connecting cables.
3. Measuring and eliminating offset voltage at six measuring points and reduces noise by hardware and software means at six measuring points.
4. Providing high output resistance and low output reactance of the current sources.
5. Minimizing noise due to analog-digital conversion.
6. Providing information on performance and reliability of measurements.
7. Providing individualized measurements of the extracellular and intracellular water mass and fat and lean body mass.

The advantages of dynamic indirect individualized measurement include, but are not limited to:
1. Providing individualized self-correcting and self-adaptive modeling of the human energy metabolism.
2. Providing real-time calculation of components of the human energy metabolism.
3. Allowing for inverse calculations and for inferring unknown input data from output results.
4. Allowing for real-time calculations in a freely moving human subject with the need for measurements only in 24 hour increments.
5. Allowing for dynamic serial measurements of the body composition change where the metabolic model is fitted to the measured data and by using error measurements of the model which becomes individualized and self-adaptive.
6. Allowing for calculating the macronutrient oxidation rates.
7. Allowing for estimation of the utilized macronutrient intake.
8. Allowing for detecting the unknown part of the energy metabolism and the error of metabolic model estimations.
9. Allowing for identification of parameters of lipid degradation and gluconeogenesis from protein.
10. Allowing for intra- as well as inter-individual comparisons of the indirectly measured metabolic parameters when using the canonical representation of the human energy metabolism, which allows quantitative characterization of the metabolism and enhances understanding of individual variations and predicts the effect of dietary and exercise interventions.
11. Allowing for trend or trajectory calculations of the lean body mass and fat mass to predict future changes quantitatively based on the daily energy density of the lean body mass change and the daily energy density of the fat mass change calculations.
12. Displaying a strong correlation between the R-ratio and other surrogate markers of insulin resistance such as the HOMA-IR (homeostasis assessment model of insulin resistance) and it can serve as a surrogate measure for non-invasive tracking of the insulin resistance change.
13. Using the R-ratio to estimate fat oxidation and gage indirectly mitochondrial dysfunction.

While the above description contains many specificities, these are not limitations on the scope, but rather as an illustration of an example embodiment. For example, the apparatus can:
1. Have a multiplicity of measuring circuits to allow segmental measurements of the parts of the human body.
2. Take measurements continuously rather than just daily or intermittently.
3. Accommodate complex lumped network models of the human body consisting of a multitude of resistances, capacitances, and inductances.
4. Obtain measurements at a higher frequency than 1 megahertz.
5. Measure the capacitances of the excitation electrodes and sensory electrodes.
6. Measure frequency dependent characteristics of the human tissue.

Further, the dynamic indirect individualized measurement method can, for example, be extended to measure dynamically:
1. The de novo lipogenesis.
2. The glycerol 3-phosphate synthesis.
3. The gluconeogenesis from glycerol.
4. The synthesis or burning of visceral fat and other segmental fat masses of a body segment.
5. The building or wasting of segmental muscle masses of a body segment.
6. The total energy expenditure.
7. The physical activity energy expenditure.
8. A daily change of lean body mass, a daily change of body fat mass, a daily change of protein mass; a daily utilized carbohydrate intake; a daily utilized fat intake; a daily utilized protein intake; a daily rate of carbohydrate oxidation; a daily rate of fat oxidation; a daily rate of protein oxidation; a daily parameter for energy flux from carbohydrate pool to fat pool; a daily parameter for uncounted energy; a daily energy density of the lean body mass change; a daily energy density of the fat mass change; and a daily R-ratio for tracking changes of insulin resistance using the R-ratio method using a Canonical Model Form of the Human Energy Metabolism method operating on portable computers or smart phones.

FIG. 6 and FIG. 7A to 7I of present disclosure on systems and methods for high frequency impedance spectroscopy detection of daily changes of dielectric properties of the human body to measure body composition and hydration status are now described in detail.

FIG. 6 and FIG. 7A to 7I show an alternative embodiment of the apparatus and method for the analysis of body composition and hydration status 109 as in FIGS. 1A and 1B. The high frequency four electrode excitation apparatus for the analysis of the human body's foot-to-foot electrical impedance and the errors of measurements as shown in FIG. 6 and FIG. 7A to 7I are primarily designed to work in the high frequency range, typically 100,000 kHz to 10 MHz. This is the frequency range which has caused many difficulties in conventional bioelectric impedance measurement mainly because the stray capacitances are not negligible.[47] The challenging issue is to measure the human body's resistance at an extrapolated infinite frequency. Finding the human body's resistance at an estimated zero frequency poses far less technical challenge.

[47] Scharfetter et al, DOI:10.1088/0967-3334/19/2/012

The high frequency four electrode excitation apparatus for the analysis of the human body's foot-to-foot electrical impedance and the errors of measurements as in FIG. 6 and FIG. 7A to 7I work as a process divided up in three parts:
1. The first part is the impedance measurement of the human body. Impedance values of the human body are measured at pre-programmed frequencies. Error analysis of the primary data collection is used to recognize and reject flawed results.
2. The second part is fitting a parametric model of human impedance. The traditional Cole model is used to fit to the measured impedance values. Model parameters are determined. These are the resistance at an estimated zero frequency, the resistance at an extrapolated infinite frequency, the characteristic time of relaxation, and the alpha exponential symbol of relaxation time dispersion. Error checking of the curve fitting procedure is performed. In case of modeling error, the data will be fitted to an extended version of the Cole model or to an individual impedance model introducing more parameters than in the original Cole model.
3. The third part is predicting the hydration status and body composition changes. A statistical calculation is performed here to predict the most likely change of hydration status and body composition since the last measurement is compared to the reference method.

The high frequency four electrode excitation apparatus for the analysis of the human body's foot-to-foot electrical impedance and the analysis errors is a second embodiment of the first embodiment of the measuring device for hydration status and body composition changes represented in FIG. 1A, 109 of the U.S. patent application Ser. No. 14/541,033 "Apparatus And Method For The Analysis Of The Change Of Body Composition And Hydration Status And For Dynamic Indirect Individualized Measurements Of The Human Energy Metabolism" and in FIG. 2 to FIG. 5V. One important innovation is that the unidirectional flow of measurement data from the apparatus to the method becomes bidirectional because the method also supplies data to the apparatus. In this application, the a priori knowledge of predictable and expected change of the human body composition and hydration status calculated by the method improves the accuracy, validity, consistency, reliability, stability, and robustness of the measured results of the daily change of the extracellular water mass, intracellular water mass, lean body mass, fat mass, and protein mass.

Part One: Impedance Measurement of the Human Body

The goal of this measurement is to determine the unknown complex impedance $Z^*_i$ of the human body to a current flow $I_i^*$ through the measured segments of the body at the predetermined frequencies 702. The measurements are fitted to an electric circuit model which describes the resistive and capacitive properties of the human body located between the sensing electrodes C1 and C2 of FIG. 6. The measurement procedure determines the complex impedance $Z^*_i$ and current flow $I^*_i$ as well as measurement and modeling errors. The mode of operation is cyclic and it is performed at preset frequencies $f_i$ ranging from 100 kHz up to 10 MHz.

The first realization of the high frequency four-electrode-excitation method is described here. A standup scale combined with the necessary electronics will perform the procedure. A user will stand on the scale with both feet positioned properly on the scale in the marked areas. The distal excitation electrode A1 for the right foot and A2 for the left foot will be snugly placed into the skin fold between the proximal toe end and distal forefoot of FIG. 6. The distal excitation electrodes B1 for the right foot and B2 for the left foot in FIG. 6 will nestle at the highest elevation and medial portion of the plantar arch. The sensing electrodes C1 for the right foot and C2 for the left foot in FIG. 6 are situated in front of the heel area which is pressing down on the scale.

Figure 6:
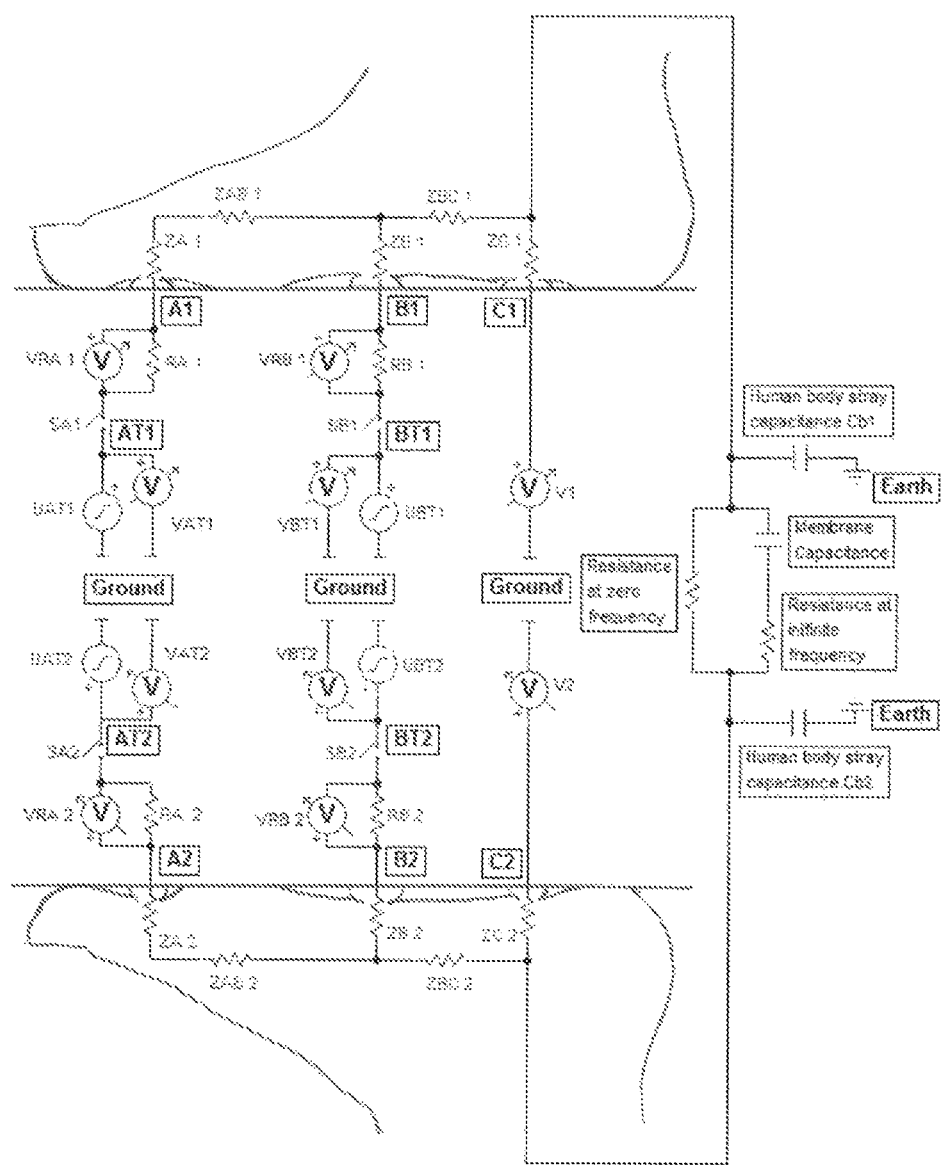
FIG. 6 shows an example arrangement of two voltage sources, two excitation electrodes and one sensing electrode for each foot. Represented are the four reference resistances and the five voltage measuring points and the model circuit elements of the complex human impedances of both feet. Depicted are the measured segment of the human body including stray capacitances of the human body, the resistance at an estimated zero frequency, resistance of an extrapolated infinite frequency, and the membrane capacitance.
Figure 7A:
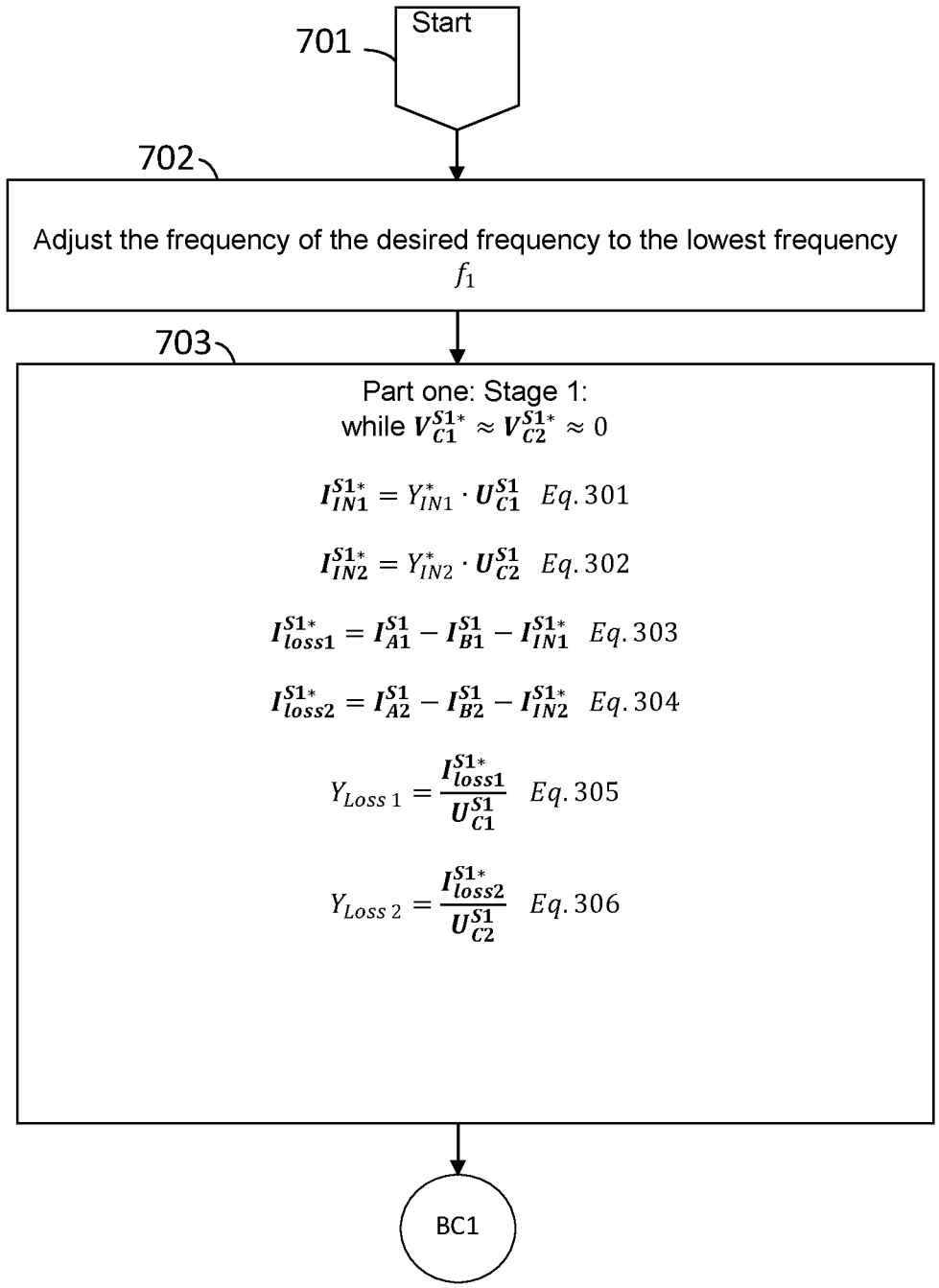
Figure 7B:
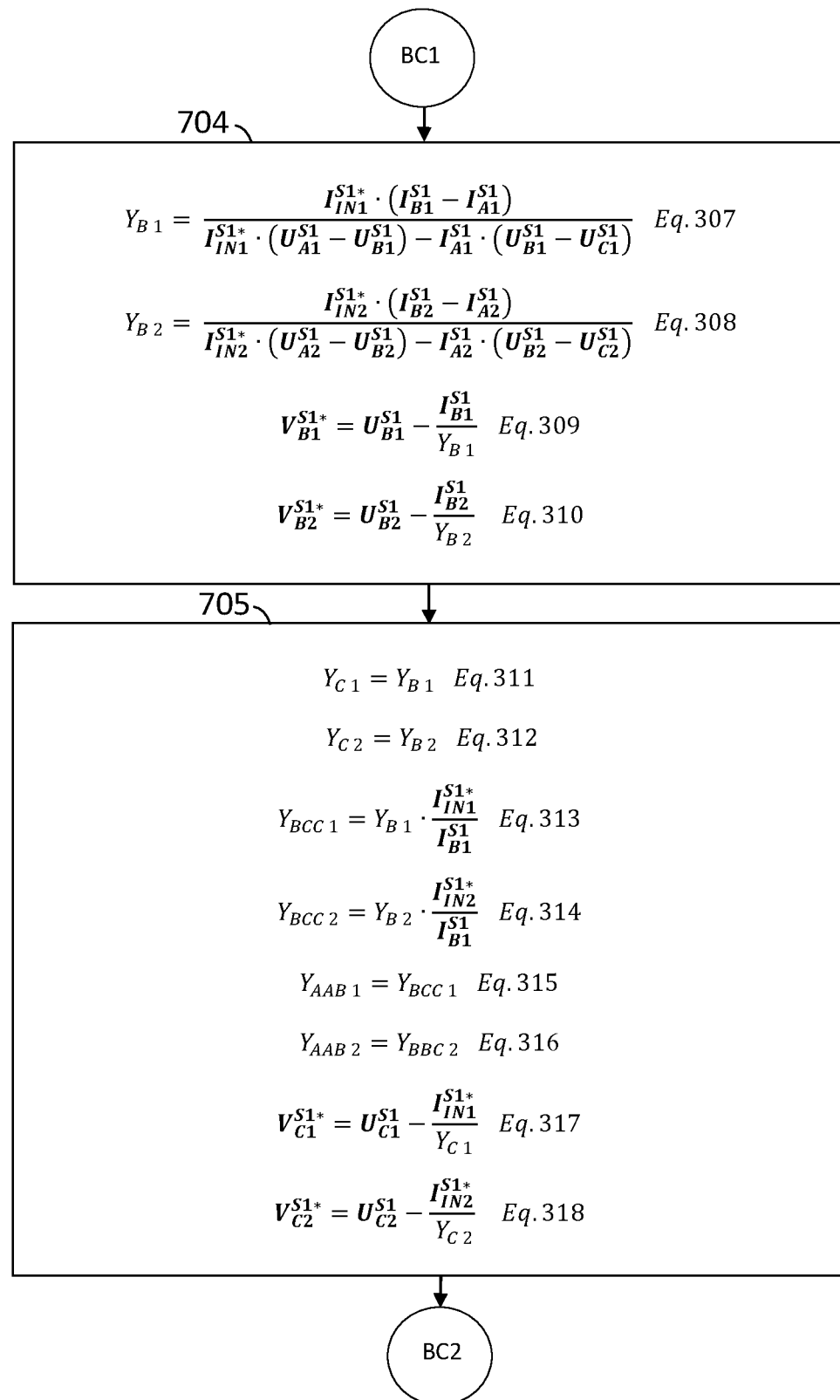
Figure 7C:
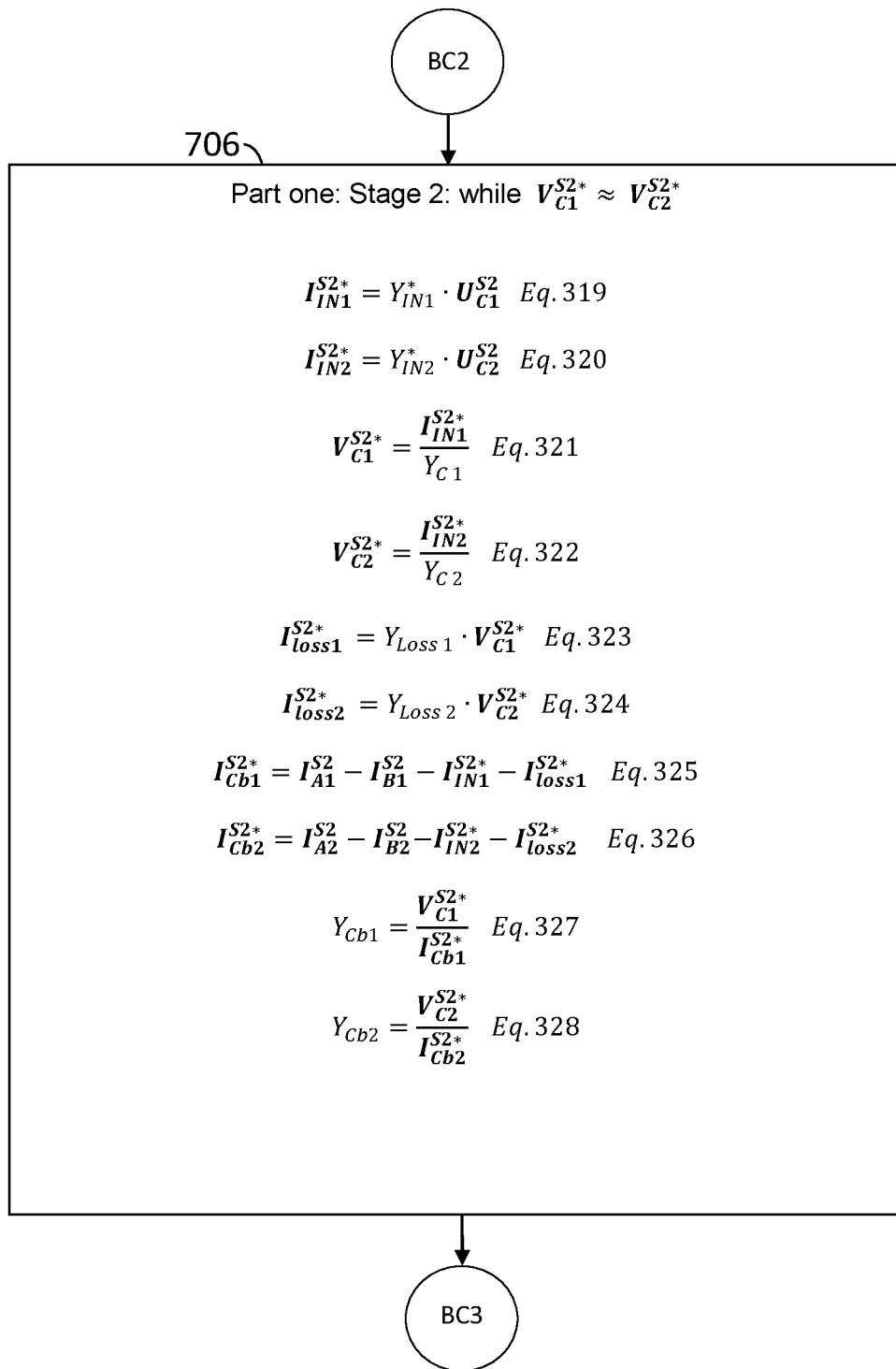
Figure 7D:
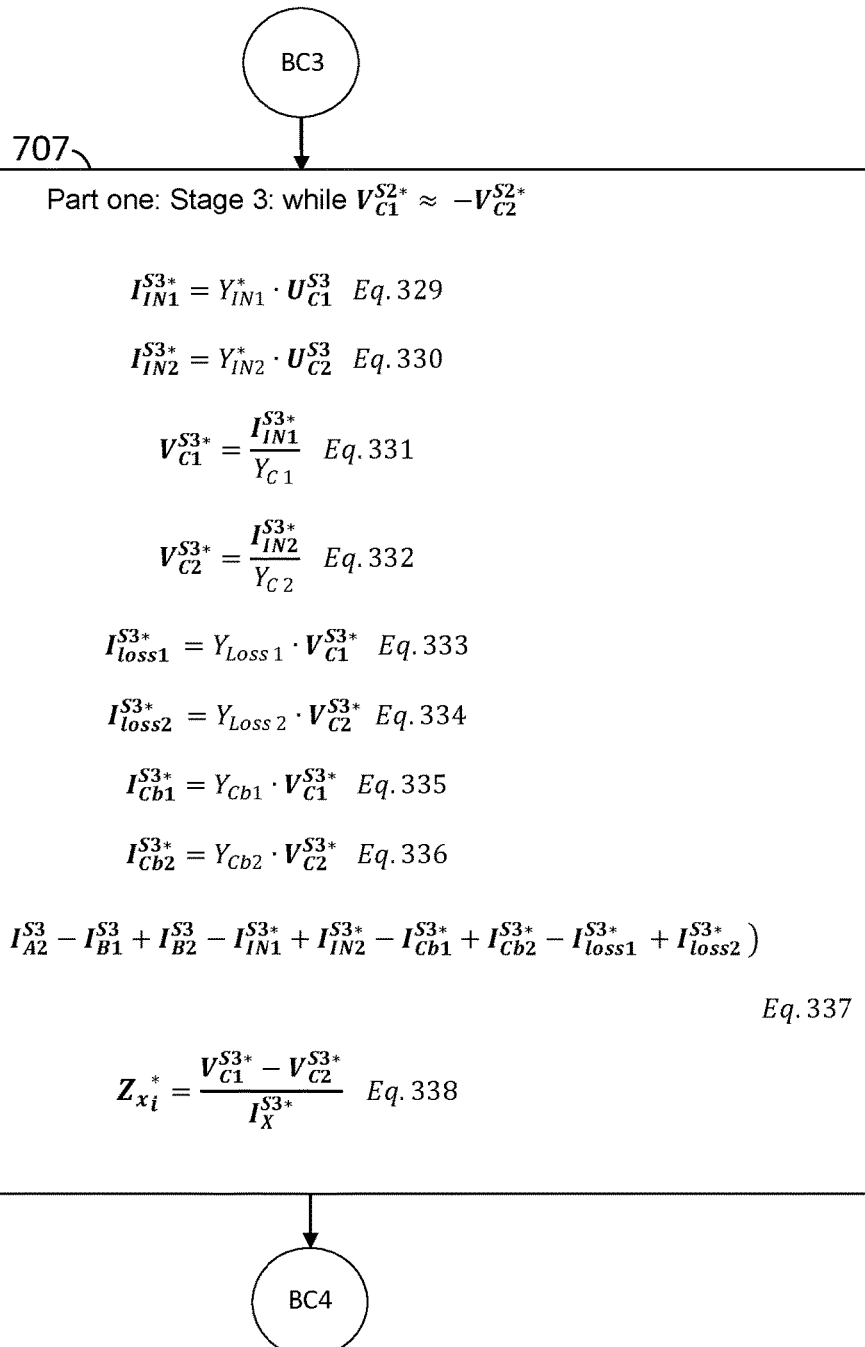
Figure 7E:
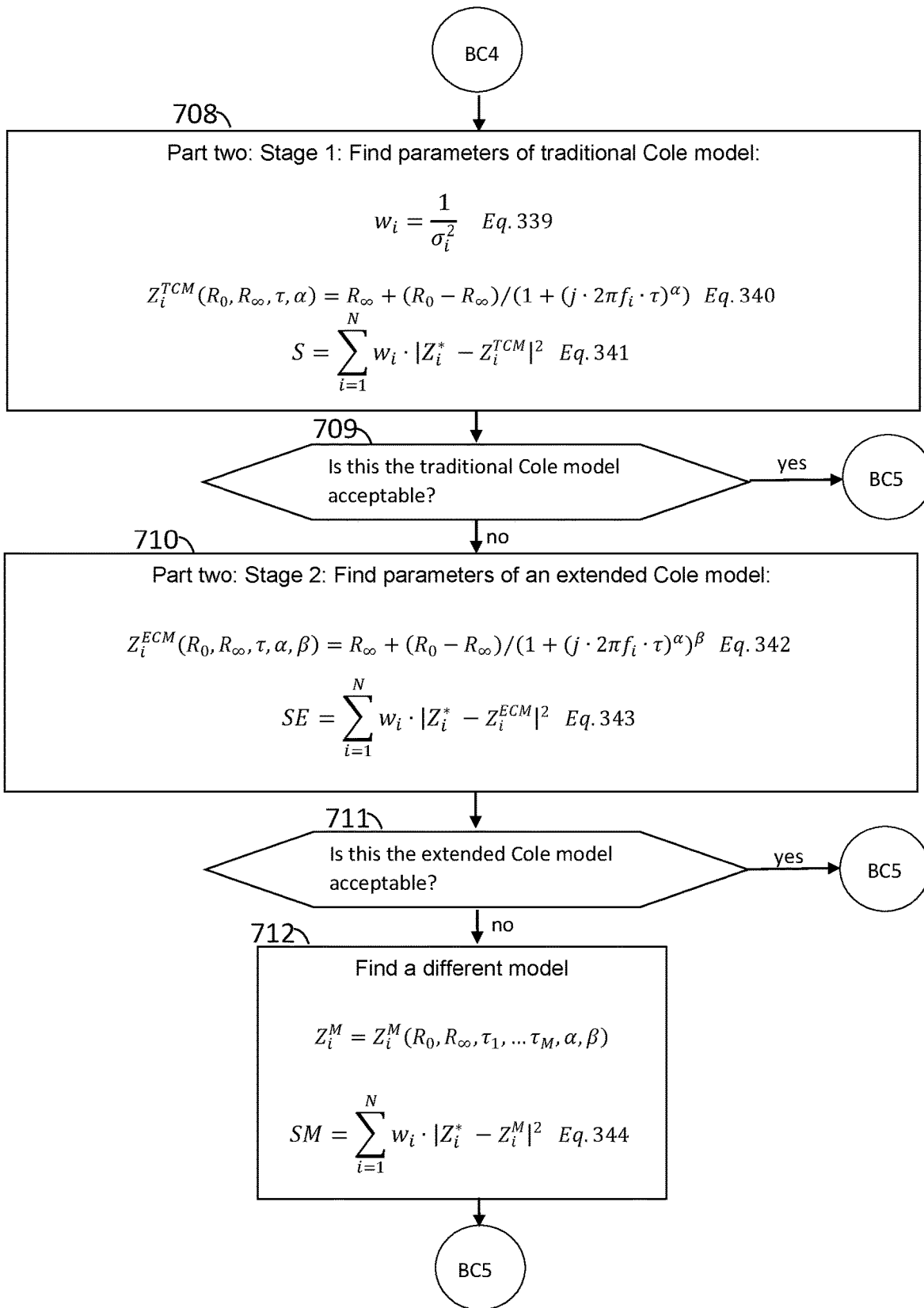
Figure 7F:
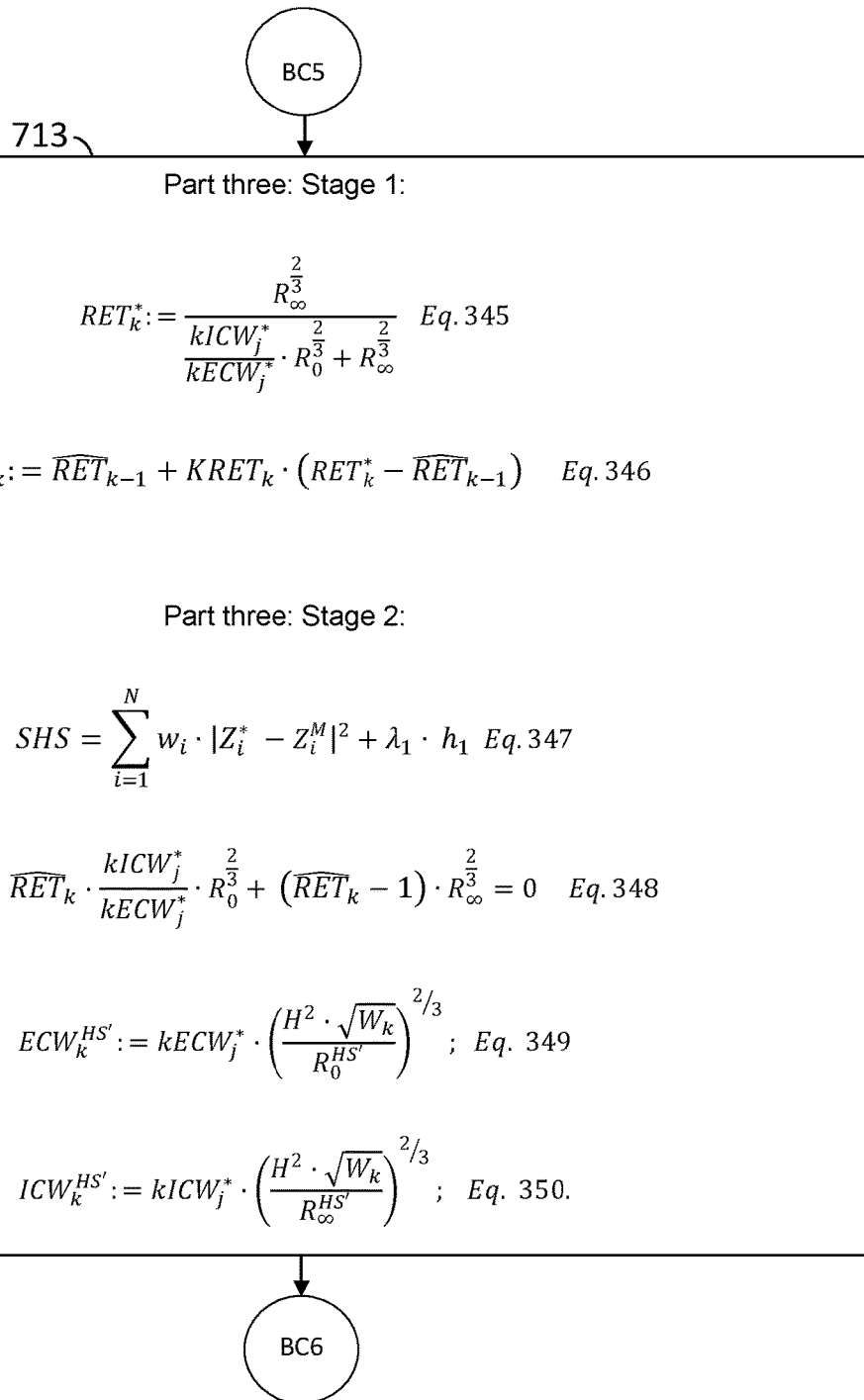
Figure 7I:
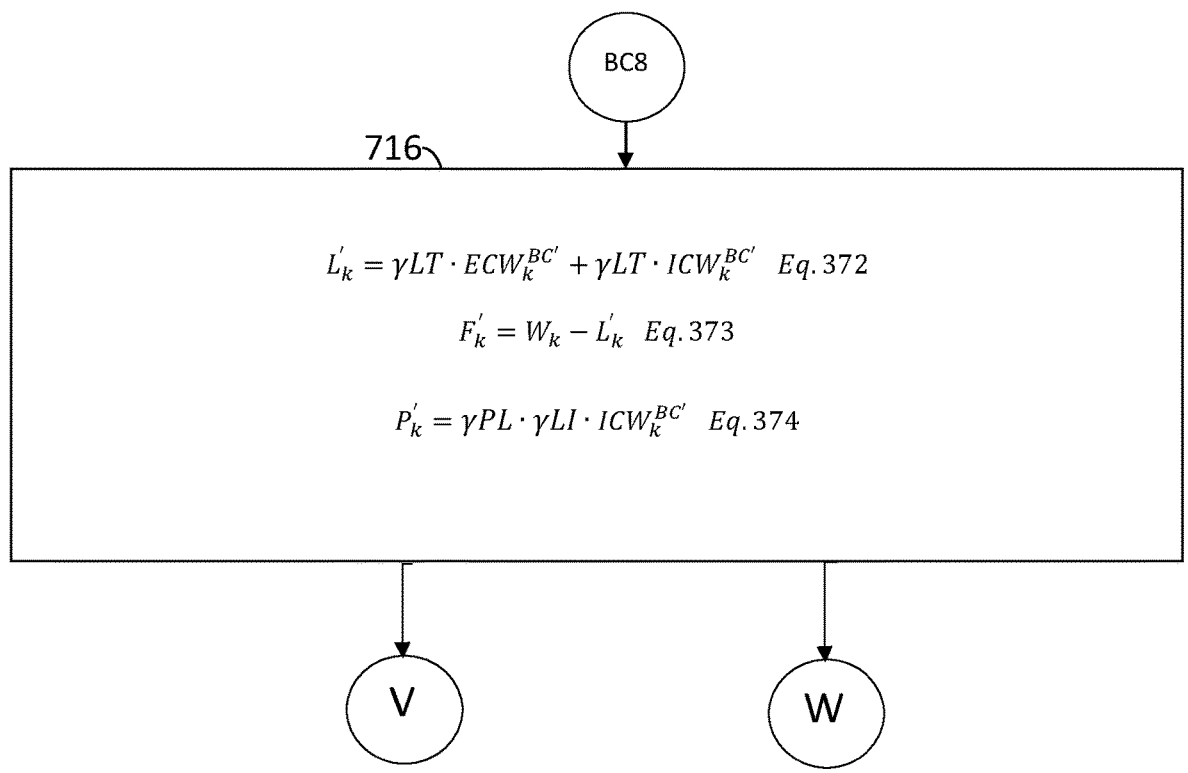

The microcontroller unit organizes the process of parallel excitation on the excitation electrodes A1, A2, B1, B2 with simultaneous measurements at the sensing electrodes C1, C2 of FIG. 6. Voltmeters VAT1, VRA 1, VBT1, VRB 1, V1 in FIG. 6 measure the amplitude, phase and offset of the signals for the right foot and voltmeters VAT2, VRA 2, VBT2, VRB 2, V2 of FIG. 6 measure the amplitude, phase and offset of the signals for the left foot. For finding the amplitude, phase and offset of a captured and digitalized voltage signal, it may be preferable to use the IEEE Std. 1057, "An Algorithm for Three Parameter (Known Frequency) Least Squared Fit to Sine-Wave Data".[48] This method provides the root mean square error, which was calculated from the best-fit sine wave. The root mean square error is used as the primary screening for errors in the primary data.

[48] IEEE *Trial-Use Standard for Digitizing Waveform Records*, pg. 13-14.

The high frequency four electrode excitation apparatus for the analysis of the human body's foot-to-foot electrical impedance and measurements errors represent an improved and second embodiment of the first embodiment of the apparatus for body composition and hydration status measurement as shown in process 109 of FIG. 1A containing processes 106, 107 and 108 of FIG. 1A, as described in the utility U.S. patent application Ser. No. 14/541,033 filed on Nov. 13, 2014 and the provisional patent application Ser. No. 62/372,363, filed on Aug. 9, 2016. The measurement process starts at 701 of FIG. 7A and ends with reaching the connectors V and W of FIG. 1A.

Part One, Stage 1, 703.

Voltage sources UAT1, UAT2, UBT1 and UBT2 of FIG. 6 are turned on at the desired measuring frequency L. Voltage source switches SA1, SB1, SA2 and SB2 of FIG. 6 are also turned on. The absolute value of the amplitude voltage sources UAT1 is approximately 1 Volt at the excitation electrode AT1 of FIG. 6 and this value is used as a reference point for all other voltage sources, i.e. for UAT2, UBT1, and UBT2. The absolute value of the amplitude of the voltage sources UAT2, UBT1 and UBT2 are chosen in a way that the voltage values at measuring electrodes C1 and C2 of FIG. 6 become equal and are as close as possible to zero. To obtain a balanced resistance bridge, the voltage source UAT1 is used as the reference source for the phase value so that the phase of voltage source UAT2 will have the same phase as UAT1. The phase values of voltage sources of UBT1 and UBT2 will be close to the opposite phase of UAT1, while adjusting the phase of UBT1 and UBT2 to satisfy the required condition that the voltage values at the sensing electrodes at C1 and C2 of FIG. 6 measured with voltmeters V1 and V2 of FIG. 6 have near zero positive value for both the real and imaginary part of the measured voltage. This tuning maneuver can be made faster by using the voltage source switches SA1, SB1, SA2 of FIG. 6 and SB2 of FIG. 6. In this case, the UBT1 voltage source is adjusted so that the voltage at V2 attains a near zero positive value for both the real and imaginary part of the measured voltage while switches SA2 and SB2 are in the off position.

Then UBT2 voltage source is adjusted so that the voltage at V1 attains a near zero positive value for both real and imaginary part of the measured voltage while switches SA1 and SB1 are in the off position.

To obtain the unknown admittance values $Y_{AAB\ 1}$, $Y_{B\ 1}$, $Y_{BCC\ 1}$, $Y_{C\ 1}$, $Y_{AAB\ 2}$, $Y_{B\ 2}$, $Y_{BCC\ 2}$, and, $Y_{C\ 2}$ of FIG. 6, Kirchhoff's first and second law for circuit analysis are used.

Directly measured current flow values are: $I_{A1}^{S1}$ at VRA 1 across resistance RA 1 of FIG. 6, $I_{B1}^{S1}$ at VRB 1 across resistance RB 1 of FIG. 6, $I_{A2}^{S1}$ at VRA 2 across resistance RA 2 of FIG. 6, and $I_{B2}^{S1}$ at VRB 2 across resistance RB 2 of FIG. 6. Directly measured voltage values are $U_{A1}^{S1}$ by adding up the voltages at VRA 1+VAT1, $U_{B1}^{S1}$ by adding up the voltages at VRB 1+VBT1, $U_{A2}^{S1}$ by adding up the voltages at VRA 2+VAT2, and $U_{B2}^{S1}$ by adding up the voltages at VRB 2+VBT2.

The current flow through electrode C1 $I_{IN1}^{S1*}$ is indirectly measured and it is calculated from the known value of $Y^*_{N1}$ characteristic to the sensing instrument V1 and the directly measured $U_{C1}^{S1}$ with V1 as in Eq. 301. The current flow through electrode C2 $I_{IN2}^{1*}$ is indirectly measured and it is calculated from known value of $Y^*_{N2}$ characteristic to the sensing instrument V2 and the directly measured $U_{C2}^{S2}$ with V2 as in Eq. 302. These characteristics are known admittance values and are obtained from the sensing device's manufacturer. An expected current loss $I_{loss1}^{S1*}$ appears which is not flowing through the measured portion of the body or through sensing electrode C1. The value of $I_{loss1}^{S1*}$ is calculated with Eq. 303. Likewise, an expected current loss $I_{loss1}^{S1*}$ appears which is not flowing through the measured portion of the body or through sensing electrode C2. The value of $I_{loss1}^{S1*}$ is calculated with Eq. 304. The current losses $I_{loss1}^{S1*}$ and $I_{loss2}^{S1*}$ represent error of measurement. This will appear because of stray capacitances on both feet and the current leakage to ground and to earth potential. This current loss is modeled by admittance $Y_{Loss\ 1}$ for the right foot and admittance $Y_{Loss\ 2}$ for the left foot; their values are calculated in Eq. 305 and Eq. 306, respectively.

For the first realization of the high frequency four-electrode-excitation method the following assumptions are made:

1. The following equations are valid for admittances $Y_{B\ 1}=Y_{C\ 1}$, $Y_{B\ 2}=Y_{C\ 2}$, $Y_{AAB\ 1}=Y_{BCC\ 1}$, and $Y_{AAB\ 2}=Y_{BBC\ 2}$ where $Y_{B\ 1}$ represents the reciprocal value of the resistance ZB 1 of FIG. 6, $Y_{C\ 1}$ represents the reciprocal value of the resistance ZC 1 of FIG. 6, $Y_{B\ 2}$ represents the reciprocal value of the resistance ZB 2 of FIG. 6, $Y_{C\ 2}$ represents the reciprocal value of the resistance ZC 2 of FIG. 6, $Y_{AAB\ 1}$ represents the reciprocal value of the resistance of ZA 1+ZAB1 of FIG. 6, $Y_{BCC\ 1}$ represents the reciprocal value of the resistance ZBC 1+ZC 1 of FIG. 6, $Y_{AAB\ 2}$ represents the reciprocal value of the resistance of ZA 2+ZAB2 of FIG. 6, and $Y_{BCC\ 2}$ represents the reciprocal value of the resistance ZBC 2+ZC 2 of FIG. 6.

2. Further, it is assumed that a successful tuning of the amplitude and phase of voltage sources of UBT1 and UBT2 are possible to achieve $U_{C1}^{S1} \approx U_{C2}^{S1}$ with values as closest as possible to zero and that this process will result in a voltage $V_{C1}^{S1*}$ between resistances ZBC 1 of FIG. 6 and ZC 1, as well as in a voltage value $V_{C2}^{S1*}$ between resistances ZBC 2 of FIG. 6 and ZC 2 to be quasi equal i.e. $V_{C1}^{S1*} \approx V_{C2}^{S1*}$ and with closest possible values to zero. Essentially, we are trying to make the voltages at these nodes to be approximately equal to each other and as close as possible to zero. At the same time, the magnitude of the current losses $I_{loss1}^{S1*}$ and $I_{loss2}^{S1*}$ approaches minimal value approximating zero.

The value of $Y_{B\ 1}$ is calculated with Eq. 307. The value of $Y_{B\ 2}$ is calculated with Eq. 308. The voltage value $V_{B1}^{S1*}$ at junction point ZAB 1 of FIG. 6 with ZBC 1 and ZB 1, and the voltage value $V_{B2}^{S1*}$ at junction point ZAB 2 of FIG. 6 with ZBC 2 and ZB 2 are calculated indirectly with Eq. 309 and Eq. 310 respectively. The value of $Y_{C\ 1}$ is calculated with Eq. 311. The value of $Y_{C\ 2}$ is calculated with Eq. 312. The value of $Y_{BCC\ 1}$ is calculated with Eq. 313. The value of $Y_{BCC\ 2}$ is calculated with Eq. 314. The value of $Y_{AAB\ 1}$ is calculated with Eq. 315. The value of $Y_{ABB\ 2}$ is calculated with Eq. 316. The voltage value $V_{C1}^{S1*}$ at junction point ZBC 1 with ZC 1, and the voltage value $V_{C2}^{S1*}$ at junction point ZBC 2 with ZC 2 are calculated indirectly with Eq. 317 and Eq. 318, respectively.

The next step is to calculate the impedance values of ZA 1, ZAB 1, ZB 1, ZBC 1, ZC 1, ZA 2, ZAB 2, ZB 2, ZBC 2, and ZC 2 in FIG. 6. The reciprocal value of $Y_{AAB\ 1}$ will give ZA 1+ZAB 1; taking the reciprocal value of $Y_{B\ 1}$ will give ZB 1; taking the reciprocal value of $Y_{BCC\ 1}$ will give ZB 1+ZBC 1; taking the reciprocal value of $Y_{C\ 1}$ will give ZC 1; taking the reciprocal value of $Y_{AAB\ 2}$ will give ZA 2+ZAB 2; taking the reciprocal value of $Y_{B\ 2}$ will give ZB 2; taking the reciprocal value of $Y_{BCC\ 2}$ will give ZB 2+ZBC 2; and taking the reciprocal value of $Y_{C\ 2}$ will give ZC 2.

Part One, Stage 2, 706.

Voltage sources UAT1, UBT1, UAT2, UBT2 are turned on at the desired measuring frequency $f_i$. Voltage source switches SA1, SB1, SA2 and SB2 are also turned on. The absolute value of the amplitude voltage sources UAT1 is approximately 1 Volt at the excitation electrode AT1 and this value is used as a reference point for all the other voltage sources, i.e. for UAT2, UBT1, and UBT2. The absolute value of the amplitude of the voltage sources UAT2, UBT1 and UBT2 remain the same as in stage 1. Using the voltage source UAT1 as the reference source for the phase value, the phase of the voltage source UAT2 will have the same phase as the UAT1 phase. The phase values of voltage sources of UBT1 and UBT2 will be close to the same phase as the reference voltage source UAT1.

For the first realization of the high frequency four-electrode-excitation method, it is assumed that a successful tuning of the amplitude and phase of the voltage sources UBT1 and UBT2 are possible to achieve $U_{C1}^{S2} \approx U_{C2}^{S2}$ and that this process will result in a voltage $V_{C1}^{S2*}$ between the resistances ZBC 1 and ZC 1, as well as in a voltage value $V_{C2}^{S2*}$ between the resistances ZBC 2 and ZC 2 which have the same amplitude and phase, i.e. $V_{C1}^{S2*} \approx V_{C2}^{S2*}$.

It is assumed here that under these conditions there will be a measurable current flow $I_{Cb1}^{S2}$ which is channeled through the human body stray capacitance $C_{b1}$ to ground in FIG. 6 and that there is also a measurable current flow $I_{Cb2}^{S2}$ which is channeled through the human body stray capacitance $C_{b2}$ of FIG. 6. It is further assumed that there will be a current flow $I_{loss1}^{S2*}$ at the right foot and a current flow $I_{loss2}^{S2*}$ at the left foot bypassing the measured segment of the human body between the sensing electrodes C1 and C2.

Directly measured current flow values are: $I_{A1}^{S2}$ at VRA 1 across resistance RA 1 of FIG. 6, $I_{B1}^{S2}$ at VRB 1 across resistance RB 1 of FIG. 6, $I_{A2}^{S2}$ at VRA 2 across resistance RA 2 of FIG. 6, and $I_{B2}^{S2}$ at VRB 2 across resistance RB 2 of FIG. 6. Additional directly measured values are: $U_{A1}^{S2}$ by adding up the voltages at VRA 1+VAT 1, $UB_{B1}^{S2}$ at VRB 1+VBT1, $U_{A2}^{S2}$ at VRA 2+VAT 2, and $U_{B2}^{S2}$ at VRB 2+VBT2.

The current flowing through electrode C1 $I_{IN1}^{S2}*$ is indirectly measured and it is calculated from the known value of the $Y*_{N1}$ characteristic to the sensing instrument V1 and the directly measured $U_{C1}^{S2}$ with V1 as in Eq. 319. The current flowing through electrode C2 $I_{IN2}^{1}*$ is indirectly measured and it is calculated from the known value of the $Y*_{N2}$ characteristic to the sensing instrument V2 and the directly measured $U_{C2}^{S2}$ with V2 as in Eq. 320. These characteristics are known admittance values and are obtained from the sensing device's manufacturer. Indirectly measured $V_{C1}^{S2}*$ is calculated as in Eq. 321. Similarly, indirectly measured $V_{C2}^{S2}*$ is calculated as in Eq. 322.

An expected current loss $I_{loss1}^{S2}*$ at the right foot appears which is not flowing through the measured portion of the body nor through the sensing electrode C1. The value of $I_{loss1}^{S2}*$ is calculated with Eq. 323. Likewise, an expected current loss $I_{loss2}^{S2}*$ at the left foot appears which is not flowing through the measured portion of the body or through the sensing electrode C2. The value of $I_{loss2}^{S2}*$ is calculated with Eq. 324.

The indirectly measured current flow $I_{Cb1}^{S2}*$ which is channeled through the human body stray capacitance $C_{b1}$ and the current flow $I_{Cb2}^{S2}*$ which is channeled through the human body stray capacitance $C_{b2}$ are calculated as in Eq. 325 and Eq. 326 respectively. The susceptance values $Y_{Cb1}$ and $Y^{Cb2}$ of the human body stray capacitance $C_{b1}$ and $C_{b2}$ are calculated as in Eq. 327 and Eq. 328 respectively.

Part One, Stage 3, 707:

Voltage sources UAT1, UBT1, UAT2, UBT2 are turned on at the desired measuring frequency $f_i$. Voltage source switches SA1, SB1, SA2 and SB2 are also turned on. The absolute value of the amplitude voltage sources UAT1 is approximately 1 Volt at the excitation electrode AT1 and this value is used as a reference point for all the other voltage sources, i.e. for UAT2, UBT 1, and UBT2. The absolute value of the amplitude of the voltage sources UAT2, UBT1 and UBT2 remain the same as in stage 2. Using the voltage source UAT1 as the reference source for the phase value the phase of voltage source UBT1 will be in the same phase as UAT1 and UAT2 and UBT2 will have the opposite phase as UAT1.

For the first realization of the high frequency four-electrode-excitation method, it is assumed that a successful tuning of amplitude and phase of voltage sources UBT1 and UBT2 are possible to achieve $U_{C1}^{S3} \approx U_{C2}^{S3}$ and this process will result in a voltage $V_{C1}^{S3}*$ between resistances ZBC 1 and ZC 1, as well as in a voltage value $V_{C2}^{S3}*$ between resistances ZBC 2 and ZC 2 which have the same amplitude but opposing phase, i.e. $V_{C1}^{S2}* \approx -V_{C2}^{S2}*$.

It is assumed here that under these conditions there will be a measurable current flow $I_{Cb1}^{S3}$ which is channeled through the human body stray capacitance $C_{b1}$ to ground and that there is also a measurable current flow $I_{Cb2}^{S3}$ which is channeled through the human body stray capacitance $C_{b2}$. Further, it is assumed that there will be a current flow $I_{loss1}^{S3}*$ at the right foot and a current flow $I_{loss2}^{S3}*$ at the left foot bypassing the measured segment of the human body between sensing electrodes C1 and C2.

Directly measured current flow values are: $I_{A1}^{S3}$ at VRA 1, $I_{B1}^{S3}$ at VRB 1, $I_{A2}^{S3}$ at VRA 2, and $I_{B2}^{S3}$ at VRB 2. Additional directly measured values are: $U_{A1}^{S3}$ by adding up the voltages at VRA 1+VAT1, $U_{B1}^{S3}$ at VRB 1+VBT1, $U_{A2}^{S3}$ at VRA 2+VAT2, and $U_{B2}^{S3}$ at VRB 2+VBT2.

The current flow through electrode C1 $I_{IN1}^{S3}*$ is indirectly measured and it is calculated from known value of $Y_{IN1}*$ characteristic to the sensing instrument V1 and the directly measured $U_{C1}^{S3}$ with V1 as in Eq. 329. The current flow through electrode C2 $I_{IN2}^{S3}*$ is indirectly measured and it is calculated from known value of $Y*_{IN2}$ characteristic to the sensing instrument V2 and the directly measured $U_{C2}^{S3}$ with V2 as in Eq. 330. These characteristics are known admittance values and are obtained from the sensing device's manufacturer. Indirectly measured $V_{C1}^{S3}*$ is calculated as in Eq. 331. Similarly, indirectly measured $V_{C2}^{S3}*$ is calculated as in Eq. 332.

An expected current loss $I_{loss1}^{S3}*$ at the right foot appears at the node between ZBC 1 and ZC 1 wherein the current flows directly to the ground and away from electrodes A1, B1, and C1. This current also flows away from the measured portion of the body, which occurs between the nodes ZBC 1 and ZC 1 of the right foot and nodes ZBC 2 and ZC 2 of the left foot. The value of $I_{loss1}^{S3}*$ is calculated with Eq. 333. Likewise, an expected current loss $I_{loss2}^{S3}*$ at the left foot also appears at the node between ZBC 2 and ZC 2 wherein the current flows directly to the ground and away from electrodes A2, B2, and C2. This current also flows away from the measured portion of the body, which occurs between the nodes ZBC 2 and ZC 2 of the left foot and nodes ZBC 1 and ZC 1 of the right foot. The value of $I_{loss2}^{S3}*$ is calculated with Eq. 334. (NOTE: ZC 1 and ZBC 1 denote the right foot, and ZC2 and ZBC 2 denote the left foot).

The indirectly measured current flow $I_{Cb1}^{S3}*$ which is channeled through the human body stray capacitance $C_{b1}$ and the current flow $I_{Cb2}^{S3}*$ which is channeled through the human body stray capacitance $C_{b2}$ are calculated as in Eq. 335 and Eq. 336, respectively.

The current flowing through the measured part of body between C1 and C2 is $I*_i$ and it is calculated as in Eq. 337. The unknown impedance between measurement electrodes C1 and C2 is $Z*_i$ at frequency $f_i$ and it is calculated as in Eq. 338.

Part Two: Fitting a Parametric Model of Human Impedance

The primary goal of this measurement is to determine the unknown resistance at an estimated zero frequency $R_0$ and resistance at an extrapolated infinite frequency $R_\infty$ with the help of a parametric model of the human impedance. The secondary goal is to arrive at an individual impedance model that is in strong agreement with the subject's impedance values during serial measurements. These goals are achieved in two stages. In stage one, the measured impedance values are fitted to the traditional Cole model. In stage two, the result of the fitting procedure is examined for statistical validity. If the traditional Cole model does not explain well the measured impedance values, then the traditional Cole model will be discarded and replaced by an extended version of the traditional Cole model which introduces more model parameters. At the end of part two, the unknown resistance at an estimated zero frequency $R_0$ and the resistance at an extrapolated infinite frequency $R_\infty$ are calculated from the accepted model of the human impedance.

Part Two, Stage 1, 708.

The weight factors $w_i$ are calculated as in Eq. 339 which is the reciprocal value of the variance $\sigma_i^2$ of the measured impedance values $Z*_i$ at frequency $f_i$ by repeating these measurements multiple times. The Unconstrained Nonlinear Least Square Programing procedure will determine the following parameters:

1. Resistance at an estimated zero frequency $R_0$, resistance at an extrapolated infinite frequency $R_\infty$.
2. Time constant $\tau$.
3. Exponent symbol $\alpha$ of the equivalent mathematical circuit model at frequency $f_i$ of the traditional Cole model as in Eq. 340 by using the measured impedance values $Z^*_i$ and minimizing the sum of error squares S as calculated in Eq. 341.

S becomes how well the parameter displays characteristics of $X^2$ distribution. Examining S with the so called $X^2$ test can result in rejection or acceptance of the traditional Cole model, 709. If the traditional Cole model in Eq. 340 is accepted as a good fit to the data, $Z^*_i$, then stage 1 ends here and the model parameter resistance at an estimated zero frequency $R_0$ and the resistance at an extrapolated infinite frequency $R_\infty$ are accepted for further calculations in Part Three. If this is not the case, then the process will proceed with part two, stage 2.

Part Two, Stage 2, 710.

An extended version of the Cole model is considered which could take the mathematical form as in Eq. 342. The Unconstrained Nonlinear Least Square Programing procedure will determine the following parameters: resistance at an estimated zero frequency $R_0$, resistance at an extrapolated infinite frequency $R_\infty$, characteristic time constant T, alpha exponential symbol of relaxation time dispersion $\alpha$, and the beta exponential symbol of relaxation time dispersion $\beta$ as in Eq. 342 by using the measured impedance values $Z_i^*$ and minimizing the sum of error squares SE as calculated in Eq. 342, 710. SE becomes how well the fit parameter displays characteristics of $X^2$ distribution. Examining SE with the $X^2$ test can result in rejection or acceptance of the extended Cole model, 711. If the extended Cole model in Eq. 340 is accepted as a good fit to the data, $Z_i^*$, then part two ends here and the model parameter resistance at an estimated zero frequency $R_0$ and the resistance at an extrapolated infinite frequency $R_\infty$ are accepted for further calculations as in part three. If this is not the case, then the process will proceed to look for an individualized model $Z_i^M (R_0, R_\infty, \tau_1, \ldots \tau_M, \alpha, \beta)$ introduces another parameter: the first-time constant of relaxation $\tau_1$ up to Mth time constant of relaxation $\tau_M$ where M is chosen to be a low integer. The process of finding the appropriate individualized model ends as soon as the SM calculated by Eq. 344 shows a good fit and using the $X^2$ test can result in acceptance of the individualized model $Z_i^M (R_0, R_\infty, \tau_1, \ldots \tau_M, \alpha, \beta)$, 712.

Part Three: Prediction of Hydration Status and Body Composition Changes

The primary goal here is to predict the hydration status i.e. extracellular water mass $ECW^*_k$ and intracellular water mass $ICW^*_k$ as well as body composition consisting of lean body mass $L'_k$, fat mass $F'_k$, and protein mass $P'_k$ for the day of measurement k. These goals are achieved in three stages. In the first stage, the ratio of the extracellular water $ECW^*_k$ to total body water mass $TBW^*_k$ for the day k is calculated, then the quasi stable extracellular water mass to total water mass is estimated. In the second stage, a constrained model fitting of the impedance values $Z^*_i$ to the chosen impedance model is used to derive the extracellular water mass $ECW^*_k$ and total water mass $TBW^*_k$ for the day k. In the third stage, a constrained model fitting of the impedance values $Z^*_i$ to the chosen impedance model is used to arrive at lean body mass $L'_k$, fat mass $F'_k$, and protein mass $P'_k$ for the day of measurement k.

Part Three, Stage 1, 713.

The results, i.e. the resistance at an estimated zero frequency $R_0$ and resistance at an extrapolated infinite frequency $R_\infty$ of the unrestrained curve fitting of part two, are used to calculate the ratio $RET^*_k$ of the extracellular $ECW^*_k$ to total body water mass $TBW^*_k$ for the day k as in Eq. 345. The reference value of the adjustable coefficient to calculate extracellular water mass $kECW^*_j$ on day j and the reference value of the adjustable coefficient to calculate intracellular water $kICW^*_j$ on day j is obtained from process equations Eq. 144 and Eq. 145 of the apparatus and method for the analysis of the change of body composition and hydration status and for dynamic indirect individualized measurements of the human energy metabolism as in FIG. 1 to FIG. 5V. The statistical estimation of the value of the quasi stationary ratio $\overline{RET}_k$ of the extracellular water to total body water is performed with the Kalman filter as in Eq. 346 where the Kalman gain $KRET_k$ is calculated as a scalar process.[49] $\overline{RET}_{k-1}$ represents the estimated ratio on the previous day.

[49] Grewal et al, "Kalman filtering theory and practice using MATLAB". Third Edition, John Wiley & Sons, New Jersey, 2008.

Part Three, Stage 2, 713.

A Nonlinear Least Square Programing procedure using Lagrange multiplier is used for constrained model fitting to the chosen individualized impedance model $Z_i^M$ to the impedance values $Z^*_i$ in order to derive the extracellular water mass $ECW'_k$ and intracellular water mass $ICW'_k$ for the day k. The sum of error squares of the constrained individualized model fitting for hydration status is represented in Eq. 347. The weight factors $w_i$ are calculated as in Eq. 339, which are the reciprocal value of the variance $\sigma_i^2$ of the measured impedance values $Z^*_i$ at frequency $f_i$ by repeated measurements. $\lambda_1$ represents the Lagrange multiplier. $h_1$ is the equation Eq. 348 for the constraint set by the quasi stationary ratio $\overline{RET}_k$ of the extracellular water mass to total body water mass on day k. The result of the constrained Nonlinear Least Square Programing procedure using Lagrange multiplier provides the resistance of the human body at an estimated zero frequency $R_0^{HSt}$ and an extrapolated infinite frequency $R_\infty^{HSt}$ satisfying the constraint in $h_1$. The extracellular water mass $ECW_k^{HSt}$ and intracellular water mass $ICW_k^{HSt}$ are determined by Eq. 349 and Eq. 350, respectively. H represents body height in cm and $W_k$ the body weight in kg on day k.

Part Three, Stage 3, 714, 715, 716.

First Embodiment of Part Three Stage Three

The first embodiment of part three, stage 3 is the combined use of the high frequency four electrode excitation apparatus for the analysis of the human body's foot-to-foot electrical impedance and the analysis errors as shown in FIG. 7A-7I and the method for the analysis of the change of body composition and hydration status and for dynamic indirect individualized measurements of the human energy metabolism as shown in FIG. 5A with bidirectional data flow. The error of estimation can be minimized with the a priori knowledge of the previous changes of the glycogen store $\Delta G_k$, and the previous changes of the protein mass $\Delta P_k$. The previous changes of the glycogen store change $\Delta G_k$ can be obtained by Eq. 111, replacing the less accurate calculation of Eq. 359. The previous changes of the protein store change $\Delta P_k$ can be obtained by Eq. 113, replacing the less accurate calculation of Eq. 358.

Second Embodiment of Part Three Stage Three

An alternative embodiment of part three, stage 3 is the standalone use of the high frequency four electrode excitation apparatus for the analysis of the human body's foot-to-foot electrical impedance and the analysis errors as shown in FIG. 6 and FIG. 7A to 7I without using the apparatus and method for the analysis of the change of body composition and hydration status and for dynamic indirect individualized measurements of the human energy metabolism as shown in FIG. 1 to FIG. 5V.

A Nonlinear Least Square Programing procedure using Lagrange multiplier is used for constrained model fitting of the chosen individualized impedance model $Z_i^M$ to the impedance values $Z^*_i$ to derive the lean body mass $L'_k$, the fat mass $F'_k$, and the protein mass $P'_k$ for the day of measurement k. The sum of error squares of the constrained individualized model fitting for body composition is represented in Eq. 351. The weight factors $w_i$ are calculated as in Eq. 339 which is the reciprocal value of the variance $\sigma_i^2$ of the measured impedance values $Z^*_i$ at frequency $f_i$ by repeated measurements. $\lambda_2$ represents the Lagrange multiplier. $h_2$ is the equation Eq. 369 with constraints set forth by five fixed ratios between different compartments of the human body. The fixed ratio of lean body mass to total body water[50] is in Eq. 352. The fixed ratio of lean cell mass to intracellular water[51] is in Eq. 353. The fixed ratio of protein mass to lean cell mass is in Eq. 354.

[50] Jaffrin et al, DOI: 10.1016/j.medengphy.2008.06.009
[51] Hall, DOI:10.1152/ajpendo.00559.2009

The fixed ratio of total body mass to bone mass is in Eq. 355. The fixed ratio of extracellular protein mass minus fraction of bone mass to extracellular mass is in Eq. 356. The body composition changes since last calibration day j for lean mass $\Delta L_k$ are calculated as in Eq. 357; for protein mass $\Delta P_k$ are calculated as in Eq. 358; and for glycogen mass $\Delta G_k$ are calculated as in Eq. 359. The size of the glycogen mass $G_k$ is calculated in Eq. 360. The mass of intracellular solutes ICS is calculated with Eq. 361. The size of bone mass BM is calculated with Eq. 362. The size of extracellular protein mass $ECP_k$ is calculated with Eq. 363. The size of protein mass $P_k$ is calculated with Eq. 364. The constraint $h_2$ in equation Eq. 369 is built from the two equations Eq. 365 and Eq. 366. Specifically, Eq. 366 is subtracted from Eq. 365, wherein the result is equal to zero, as shown in Eq. 367. This constrains $h_2$ because the result of the subtracting the two equations must be zero as shown in Eq. 367. Eq. 365 shows the compartmentalized lean body mass calculation, while Eq. 366 shows the calculation from the extracellular water mass $ECW^*_k$ and intracellular water mass $ICW^*_k$.

The equation Eq. 368 shows the substitutions for protein mass $P_k$, glycogen mass $G_k$, intracellular solute ICS, extracellular protein mass $ECP_k$ and bone mass BM with the expressions showing the dependency from either the extracellular water mass $ECW^*_k$ or the intracellular $ICW^*_k$ water mass. In equation Eq. 369, the extracellular water mass $ECW^*_k$ or the intracellular $ICW^*_k$ water mass is replaced with Eq. 148 and Eq. 149 from the "apparatus and method for the analysis of the change of body composition and hydration status and for dynamic indirect individualized measurements of the human energy metabolism" as shown in FIG. 1 to FIG. 5V. The result of the constrained Nonlinear Least Square Programing procedure using Lagrange multiplier provides the resistance of the human body at an estimated zero frequency $R_0^{BC_1}$ and an extrapolated infinite frequency $R_\infty^{BC_1}$ satisfying the constraint in $h_2$.

The extracellular water mass $ECW_k^{BC_1}$ and intracellular water mass $ICW_k^{BC_1}$ are determined by Eq. 370 and Eq. 371, respectively. H represents body height in cm and $W_k$ the body weight in kg on day k. The lean body mass $L'_k$ is calculated by Eq. 372, the fat mass $F'_k$ is calculated by Eq. 373, and the protein mass $P'_k$ is calculated by Eq. 374 for the day of measurement k.

Thus, it can be seen that at least one embodiment of the high frequency four electrode excitation apparatus for the analyses of the human body's foot-to-foot electrical impedance and the errors of measurements provide for a measurement and individualized modeling of the human body's electrical impedance, as well as a prediction of extracellular and intracellular water compartments changes and body composition changes.

The advantages of the present disclosure's "systems and methods for high frequency impedance spectroscopy detection of daily changes of dielectric properties of the human body to measure body composition and hydration status" over prior art include, but are not limited to:

1. Measuring the impedance of 4 excitation electrodes and 2 measuring electrodes without using input logic circuits.
2. Measuring simultaneously the body weight and complex electrical impedance of the human body at a multitude of frequencies ranging from 100 kHz to 10 MHz in standing positions between two sensing electrodes. The arrangement of the electrodes is such that they are in contact with the thinnest skin areas of the foot. Specifically, the electrodes have the best contacts through the thinnest skin areas of the foot with an arrangement forcing the user to maintain the same electrode position during repeated measurements.
3. Measuring stray capacitance of the measured body segment between the two sensing electrodes and separately the stray capacitances outside of the measured body segment which include the stray capacitances of both feet and the measuring instrumentation itself
4. Registering environmental factors at the time of measurement including location, room temperature, local environmental electromagnetic influences and notes physiological factors such as accurate body weight, time of the measurement, duration of measurement, and skin temperature.
5. Measuring common ground potential and compensates for asymmetric arrangements of the measuring objects and varying electrode impedances.
6. Measuring electrical voltage signals at 10 measuring points, digitizing the signal, fitting it with sine wave function, and determining amplitude, phase, offset and the sum of the least square error of fitting.
7. Measuring the impedance of the human body between sensing electrodes by removing effects of stray capacitances of the measured segment of the human body and current losses outside of the measured segment of the human body.
8. Calculating the parameters of the Cole model including resistance at an extrapolated infinite frequency, resistance at an estimated zero frequency, characteristic time of relaxation, alpha exponential symbol of relaxation time dispersion, goodness of fit parameters, and giving the result of the sum of least square error of fitting.
9. Performing statistical tests for goodness of fit of the Cole model. In the case of large modelling error by the Cole model, various improved models of the human impedance will be tested for modelling error until the modelling error decreases to a satisfactory level.
10. Measuring daily changes of extracellular and intracellular water mass with the individualized model holding to and updating a quasi-stable extracellular to intracellular water mass ratio.
11. Measuring changes of lean body mass, fat mass, and protein mass with the individualized model of the human impedance. The individualized model of the human impedance is fitted to the measured impedance data at preset frequencies while using five constraints which are the ratio of lean body mass to total body water; the fixed ratio of lean cell mass to intracellular water; the fixed ratio of protein mass to lean cell mass; the fixed ratio of total body mass to bone mass; and the fixed ratio of extracellular protein mass minus fraction of bone mass to extracellular mass.

12. Providing options and taking advantage of serial measurements in the same subject. It can use a priori information regarding predictable changes of body composition which can be obtained from the method for the analysis of the change of body composition and hydration status and for dynamic indirect individualized measurements of the human energy metabolism in U.S. patent Ser. No. 14/541,033. Herewith advantage is taken from the knowledge of likely trends of changes of the body composition to improve validity, consistency, reliability, stability, and robustness for improved predictions of results. The standard deviation and confidence interval measures of results are calculated and optionally, a trend prediction of the results is given.

13. Using the apparatus to provide measurement results to the method: the measured extracellular water mass on day k $ECW'_k$ can be used in Eq. 148 and Eq. 150; the intracellular water mass on day k $ICW'_k$ can be used in Eq. 149 and Eq. 150; the resistance of the human body at an estimated zero frequency with constraints to assess body composition $R_0^{BC'}$ can be used in Eq. 144 and Eq. 148; the resistance of the human body at an extrapolated infinite frequency with constraints to assess body composition $R_\infty^{BC'}$ can be used in Eq. 145 and Eq. 149; the resistance of the human body at an estimated zero frequency with constraints to assess hydration status $R_0^{HS'}$ can be used in Eq. 159; the resistance of the human body at an extrapolated infinite frequency with constraints to assess hydration status $R_\infty^{HS'}$ can be used in Eq. 160; the lean body mass on day k $L'_k$ can be used in Eq. 150 and Eq. 248; the fat mass on day k $F'_k$ can be used in Eq. 151 and Eq. 249; the protein mass on day k $P'_k$ can be used in Eq. 250; the lean body mass change from day k−1 up to day k $\Delta L_k$ can be used in Eq. 116, Eq. 118, Eq. 152, Eq. 201, Eq. 207, and Eq. 218; the fat body mass change, $\Delta F_k$, from day k−1 up to day k can be used in Eq. 116, Eq. 118, Eq. 153, Eq. 202, Eq. 208, and Eq. 219; the lean body mass change, $\Delta P_k$, from day k−1 up to day k can be used in Eq. 116, Eq. 235, and Eq. 259.

14. Using the apparatus to accept results from the method from the parent U.S. patent Ser. No. 14/541,033: the previous changes of the glycogen store change $\Delta G_k$ can be obtained by Eq. 111, replacing the less accurate calculation of Eq. 359. The previous changes of the protein store change $\Delta P_k$ can be obtained by Eq. 113, replacing the less accurate calculation of Eq. 358.

As referred to herein, the term "computing device" should be broadly construed. It can include any type of device including hardware, software, firmware, the like, and combinations thereof. A computing device may include one or more processors and memory or other suitable non-transitory, computer readable storage medium having computer readable program code for implementing methods in accordance with embodiments of the present disclosure. In an example, a computing device may be any type of conventional computer, such as a laptop computer or a tablet computer or a desktop computer. In another example, the computing device may be a type of network device such as a router or a switch. In another example, the computing device may be a smart television or a high definition television. In another example, the computing device may be a battery powered Internet of Things (IoT) device. In another example, a computing device may be a mobile computing device such as, for example, but not limited to, a smart phone, a cell phone, a pager, a personal digital assistant (PDA), a mobile computer with a smart phone client, or the like. A typical mobile computing device is a wireless data access-enabled device (e.g., an iPHONE® smart phone, a BLACKBERRY® smart phone, a NEXUS ONE™ smart phone, an iPAD® device, or the like) that is capable of sending and receiving data in a wireless manner using protocols like the Internet Protocol, or IP, and the wireless application protocol, or WAP. This allows users to access information via wireless devices, such as smart phones, mobile phones, pagers, two-way radios, communicators, and the like. Wireless data access is supported by many wireless networks, including, but not limited to, CDPD, CDMA, GSM, PDC, PHS, TDMA, FLEX, ReFLEX, iDEN, TETRA, DECT, DataTAC, Mobitex, EDGE and other 2G, 3G, 4G and LTE technologies, and it operates with many handheld device operating systems, such as PalmOS, EPOC, Windows CE, FLEXOS, OS/9, JavaOS, iOS and Android. Typically, these devices use graphical displays and can access the Internet (or other communications network) on so-called mini- or micro-browsers, which are web browsers with small file sizes that can accommodate the reduced memory constraints of wireless networks. In a representative embodiment, the mobile device is a cellular telephone or smart phone that operates over GPRS (General Packet Radio Services), which is a data technology for GSM networks. In addition to voice communication, a given mobile device can communicate with another such device via many different types of message transfer techniques, including SMS (short message service), enhanced SMS (EMS), multi-media message (MMS), email WAP, paging, or other known or later-developed wireless data formats. Although many of the examples provided herein are implemented on servers in a datacenter, the examples may similarly be implemented on any suitable computing device or computing devices.

The present subject matter may be a system, a method, and/or a computer program product. The computer program product may include a computer readable storage medium (or media) having computer readable program instructions thereon for causing a processor to carry out aspects of the present subject matter.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present subject matter may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a standalone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present subject matter.

Aspects of the present subject matter are described herein with reference to flowchart illustrations and/or block diagrams of methods, apparatus (systems), and computer program products according to embodiments of the subject matter. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present subject matter. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While certain embodiments have been described, these embodiments have been presented by way of example only, and are not intended to limit the scope of the inventions. Indeed, the novel methods, devices, and systems described herein may be embodied in a variety of other forms. Furthermore, various omissions, substitutions, and changes in the form of the methods, devices, and systems described herein may be made without departing from the spirit of the inventions. The accompanying claims and their equivalents are intended to cover such forms or modifications as would fall within the scope and spirit of the inventions.

What is claimed:

1. A method comprising:
   at a computing device to determine a set of indirect dynamic human metabolism parameters:
   using a sensor on an individual to acquire a set of electrical measurements;
   combining a ratio technique with a canonical model form technique;
   performing a series of mathematical calculations on the acquired set of electrical measurements to determine the set of indirect dynamic human metabolism parameters for the individual based on the combined ratio technique and the canonical model form technique; and
   in response to performing the series of mathematical calculations on the acquired set of electrical measurements to determine the set of indirect dynamic human metabolism parameters for the individual, generating a trend regarding the set of indirect dynamic human metabolism parameters, whereby the generated trend provides improved predictive metabolic health information to the individual for use to manage at least one of an individual's metabolic health, fitness goals, body composition goals, hydration goals, and insulin resistance related fat versus carbohydrate burning preference goals.

2. The method of claim 1, wherein the ratio technique is the individual's daily ratio of a lean body mass change velocity to a fat mass change velocity and is called an R-ratio, where R-ratio is used to determine the insulin resistance related fat versus carbohydrate burning preference.

3. The method of claim 1, wherein the canonical model form technique comprises of at least one of a Canonical Model Form of Human Energy Metabolism and a Self-Adaptive Input Output Model of Human Energy Metabolism.

4. The method of claim 1, further comprising acquiring the following additional electrical measurements:
   a first voltage source;
   a first reference resistance;
   a first excitation electrode attached to a plantar surface metatarsophalangeal area of at least one of a first foot and a second foot wherein the foot is based on the generation step;
   an impedance segment of at least one of the first foot and the second foot wherein the foot is based on the step of generating a trend;
   a second excitation electrode at a highest elevation and medial portion of a plantar arch of one of the first foot and the second foot;
   a second reference resistance; and
   a second voltage source.

5. The method of claim 1, wherein the set of indirect dynamic human metabolism parameters comprises:
   a daily change of lean body mass; a daily change of body fat mass;
   a daily change of protein mass;
   a daily utilized carbohydrate intake; a daily utilized fat intake;
   a daily utilized protein intake;
   a daily rate of carbohydrate oxidation;
   a daily rate of fat oxidation;
   a daily rate of protein oxidation;
   a daily insulin resistance related fat versus carbohydrate burning ratio;
   a daily parameter for energy flux from carbohydrate pool to fat pool;
   a daily parameter for uncounted energy;
   a daily energy density of the lean body mass change;
   a daily energy density of the fat mass change;
   a daily ratio of lean body mass change velocity; and a daily ratio of fat mass change velocity.

* * * * *